United States Patent [19]
Hebeisen et al.

[11] Patent Number: 5,804,577
[45] Date of Patent: Sep. 8, 1998

[54] CEPHALOSPORIN DERIVATIVES

[75] Inventors: Paul Hebeisen, Basel, Switzerland; Ingrid Heinze-Krauss, Schliengen; Hans Richter, Grenzach-Wyhlen, both of Germany; Valeri Runtz, Rixheim, France; Henri Stalder, Basel; Urs Weiss, Pratteln, both of Switzerland; George Petros Yiannikouros, Westfield, N.J.

[73] Assignee: Hoffmann-La Roche Inc., Nutley, N.J.

[21] Appl. No.: 708,161

[22] Filed: Aug. 27, 1996

[30] Foreign Application Priority Data

Sep. 12, 1995 [EP] European Pat. Off. .............. 95114303
Sep. 19, 1995 [EP] European Pat. Off. .............. 95114304

[51] Int. Cl.$^6$ ...................... A61K 31/545; C07D 501/34
[52] U.S. Cl. .................. 514/202; 514/206; 514/225; 540/221; 540/222; 540/227; 540/225
[58] Field of Search ..................... 514/202, 203, 514/205, 206; 540/225, 227, 221, 222

[56] References Cited

U.S. PATENT DOCUMENTS 4,255,423 3/1981 Beattie et al. .............................. 544/16
5,523,400 6/1996 Wei et al. ................................ 514/202

FOREIGN PATENT DOCUMENTS 359 536 3/1990 European Pat. Off. .
620 225 10/1994 European Pat. Off. .

OTHER PUBLICATIONS

Heinze–Krauss, I., et al., Journal of Medicinal Chemistry, 39(9):1864–71 (1996).

Primary Examiner—Mukund J. Shah
Assistant Examiner—Pavanaram K. Sripada
Attorney, Agent, or Firm—George W. Johnston; Dennis P. Tramaloni; Alan P. Kass

[57] ABSTRACT

The present invention relates to compounds of formula I

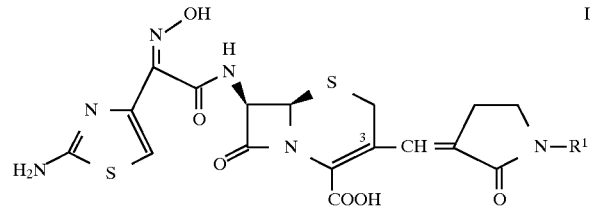

wherein $R^1$ is a group selected from 2-, 3-, and 4-hydroxyphenyl, 3-nitrophenyl, and 3-fluoro-4-hydroxyphenyl; as well as readily hydroyzable esters thereof, pharmaceutically acceptable salts of said compounds and hydrates of the compounds of formula I and of their esters and salts.

10 Claims, No Drawings

CEPHALOSPORIN DERIVATIVES

The present invention relates to compounds of formula I

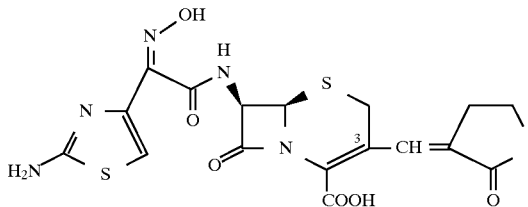

wherein $R^1$ is a group selected from 2-, 3- and 4-hydroxyphenyl, 2- and 3-methoxyphenyl, 4-carboxyphenyl, 4-carbamoylphenyl, 3-trifluoromethylphenyl, 2- and 3-fluorophenyl, 3-nitrophenyl, 3-fluoro-4-hydroxyphenyl, 2-fluoro-4-hydroxyphenyl, 3-fluoro-2-hydroxyphenyl, 3-, 4-dihydroxyphenyl, benzyl, —CHR-phenyl, 3-hydroxybenzyl, 4-aminobenzyl, 2-, 3- and 4-fluorobenzyl, 2-, 3- and 4-methoxybenzyl, 4-nitrobenzyl, 4-carboxybenzyl, 4-trifluoromethylbenzyl, 1-naphthyl and 2-naphthyl, the aforementioned hydroxy substituents being unsubstituted or substituted with tertbutyloxycarbonyl, triphenylmethyl, or tertbutyldimethylsilyl, the aforementioned amino and carbamoyl substituents each being unsubstituted or substituted with benzhydryl, allyloxycarbonyl, tertbutyloxycarbonyl, or succinyl, and the aforementioned carboxy substituents being unsubstituted or substituted with benzhydryl, tertbutyloxycarbonyl, triphenylmethyl, 4-nitrobenzyl, 4-methoxybenzyl, or allyl, or is pyridinyl monosubstituted with halogen, pyrimidyl, pyrazinyl di-substituted with lower alkyl, pyridazinyl monosubstituted with halogen, piperidinyl in which the amino group is unsubstituted or substituted by an acyl group, thiadiazolyl, oxo-tetrahydrofuranyl, thiophenyl mono-substituted with lower alkoxycarbonyl or carbamoyl, tetrazolyl-lower alkyl, tetrahydrofuranyl-lower alkyl, thiophenyl-lower alkyl or benzimidazolyl-lower alkyl; and R is carboxy or esterified carboxy;

as well as readily hydrolyzable esters thereof, pharmaceutically acceptable salts of said compounds and hydrates of the compounds of formula I and of their esters and salts.

In above compounds of formula I the substituent in position 3 can be present in the E-form, see formula Ia or in the Z-form, see formula Ib:

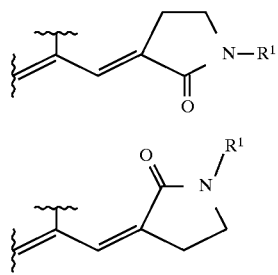

The compounds of the formula I are preferably in the E-form.

The substituent in "substituted carboxy" is a group conventionally used to replace the acidic proton of a carboxylic acid. Examples of such groups are benzhydryl, tert-butyl, triphenylmethyl, 4-nitrobenzyl, 4-methoxybenzyl and allyl.

The substituent in "substituted hydroxy" is a group conventionally used to replace the proton of a hydroxy group. Examples of such groups are tert-butyloxycarbonyl, triphenylmethyl, tert-butyldimethylsilyl, and the like.

The substituent in "substituted amino" and "substituted carbamoyl" is a group conventionally used to replace the proton of an amino group. Examples of such groups are benzhydryl, allyloxycarbonyl, tert-butyloxycarbonyl, succinyl and the like.

As used herein, the term "lower alkyl" refers to both straight and branched chain saturated hydrocarbon groups having 1 to 8 and preferably 1 to 4 carbon atoms, for example, methyl, ethyl, n-propyl, isopropyl, tertiary butyl and the like. Most preferred are methyl and ethyl.

As used herein, the term "lower alkenyl" refers to hydrocarbon chain radicals having from 2 to 8 carbon atoms, preferably from 2 to 4 carbon atoms, and having at least one olefinic double bond, e.g. allyl, vinyl etc. Most preferred is allyl.

By the term "lower alkoxycarbonyl" as utilized herein is intended a moiety of the formula $R_a$—O—CO—, wherein $R_a$ is lower alkyl, preferably ethyl.

By the term "carbamoyl" as utilized herein is intended a moiety of the formula —CO—$NR^2R^3$, wherein each of $R^2$ and $R^3$ independently signify hydrogen or lower alkyl.

The nitrogen atom in the piperidinyl-ring can be unsubstituted or substituted by an acyl group, conveniently by lower alkoxycarbonyl such as ethoxycarbonyl, by lower alkenyl-oxycarbonyl such as allyloxycarbonyl or by a carboxy-lower-alkanoyl group, such as the succinate-residue of the formula HOOC—$CH_2$—$CH_2$—CO—.

As used herein, "halogen" refers to bromine, chlorine, fluorine or iodine. Chlorine is preferred.

Preferred compounds of formula I are compounds wherein $R^1$ is a group selected from 2-, 3- and 4-hydroxyphenyl, 2- and 3-methoxyphenyl, 4-carboxyphenyl, 4-carbamoylphenyl, 3-trifluoromethylphenyl, 2- and 3-fluorophenyl, 3-nitrophenyl, 3-fluoro-4-hydroxyphenyl, 2-fluoro-4-hydroxyphenyl, 3-fluoro-2-hydroxyphenyl, 3-, 4-dihydroxyphenyl, benzyl, —CHR-phenyl, 3-hydroxybenzyl, 4-aminobenzyl, 2-, 3- and 4-fluorobenzyl, 2-, 3- and 4-methoxybenzyl, 4-nitrobenzyl, 4-carboxybenzyl, 4-trifluoromethylbenzyl, 1-naphthyl and 2-naphthyl, the aforementioned hydroxy substituents being unsubstituted or substituted with tertbutyloxycarbonyl, triphenylmethyl, or tertbutyldimethylsilyl, the aforementioned amino and carbamoyl substituents each being unsubstituted or substituted with benzhydryl, allyloxycarbonyl, tertbutyloxycarbonyl, or succinyl, and the aforementioned carboxy substituents being unsubstituted or substituted with benzhydryl, tertbutyloxycarbonyl, triphenylmethyl, 4-nitrobenzyl, 4-methoxybenzyl, or allyl, and R is as defined above.

Especially preferred compounds of formula I are compounds wherein $R^1$ is a group selected from 4-hydroxyphenyl, 3-nitrophenyl, 3-fluoro-4-hydroxyphenyl, benzyl, 3-hydroxybenzyl, 4-aminobenzyl and 4-(succinylamino)benzyl.

Preferred compounds of formula I include:

(6R,7R)-7-[(Z)-2-(2-Amino-thiazol-4-yl)-2-hydroxyimino-acetylamino]-3-[(E)-1-(4-hydroxy-phenyl)-2-oxo-pyrrolidin-3-ylidenemethyl]-8-oxo-5-thia-1-aza-bicyclo[4.2.0]oct-2-ene-2-carboxylic acid

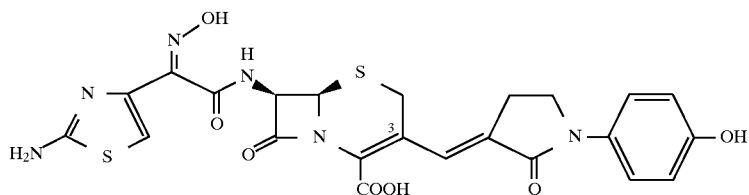

(6R,7R)-7-[(Z)-2-(2-Amino-thiazol-4-yl)-2-hydroxyimino-acetylamino]-3-[(E)-1-(3-nitro-phenyl)-2-oxo-pyrrolidin-3-ylidenemethyl]-8-oxo-5-thia-1-aza-bicyclo[4.2.0]oct-2-ene-2-carboxylic acid

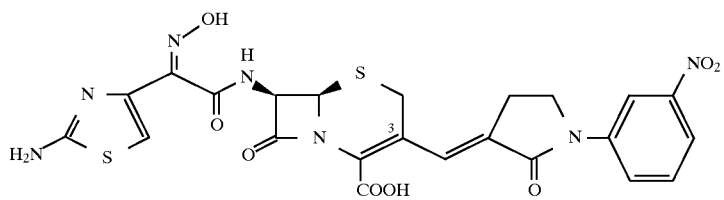

(6R,7R)-7-[(Z)-2-(2-Amino-thiazol-4-yl)-2-hydroxyimino-acetylamino]-3-[(E)-1-(3-fluoro-4-hydroxy-phenyl)-2-oxo-pyrrolidin-3-ylidenemethyl]-8-oxo-5-thia-1-aza-bicyclo[4.2.0]oct-2-ene-2-carboxylic acid

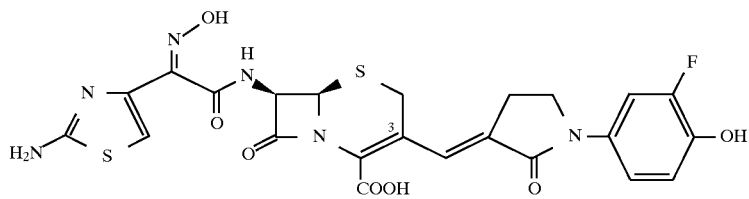

(6R,7R)-7-[(Z)-2-(2-Amino-thiazol-4-yl)-2-(hydroxyimino-acetylamino]-3-[(E)-1-(4-aminobenzyl)-2-oxo-pyrrolidin-3-ylidenemethyl]-8-oxo-5-thia-1-azabicyclo[4.2.0]oct-2-ene-2-carboxylic acid and

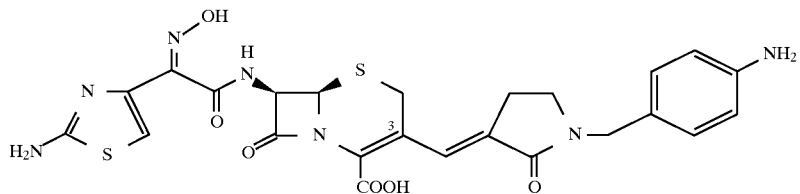

(6R,7R)-7-[(Z)-2-(2-Amino-thiazol-4-yl)-2-hydroxyimino-acetylamino]-3-[(E)-1-(3-hydroxybenzyl)-2-oxo-pyrrolidin-3-ylidenemethyl]-8-oxo-5-thia-1-azabicyclo[4.2.0]oct-2-ene-2-carboxylic acid.

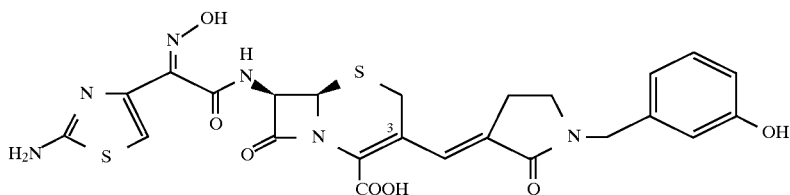

A further preferred group of compounds of formula I are compounds wherein R¹ is pyridinyl mono-substituted with halogen, pyrimidyl, pyrazinyl di-substituted with lower alkyl, pyridazinyl mono-substituted with halogen, piperidinyl in which the amino group is unsubstituted or substituted by an acyl group, thiadiazolyl, oxo-tetrahydrofuranyl, thiophenyl mono-substituted with lower alkoxycarbonyl or carbamoyl, tetrazolyl-lower alkyl, tetrahydrofuranyl-lower alkyl, thiophenyl-lower alkyl or benzimidazolyl-lower alkyl.

Especially preferred are compounds of formula I wherein R¹ is 2-chloro-pyridin-3-yl, 1-pyrimidin-2-yl, 3,5-dimethylpyrazin-2-yl, 6-chloro-pyridazin-3-yl, 1-piperidin-4-yl, 1-ethoxycarbonyl-piperidin-4-yl, 1-allyloxycarbonyl-piperidin-4-yl, 1-carboxypropionyl-piperidin-4-yl, 1,3,4-thiadiazolyl-2-yl, 2-oxo-tetrahydrofuranyl-3-yl, 3-ethoxycarbonylthiophen-2-yl, 3-carbamoyl-thiophen-2-yl, 1H-tetrazol-5-yl-methyl, tetrahydrofuran-2-yl-methyl, thiophen-2-yl-methyl or 1H-benzimidazol-2-yl-methyl.

Further preferred are compounds of formula I wherein R¹ is 1,3,4-thiadiazolyl-2-yl, 1H-benzimidazo-2-yl-methyl or 1-piperidin-4-yl.

Even further preferred compounds of formula I include:
(6R,7R)-7-[(Z)-2-(2-Amino-thiazol-4-yl)-2-hydroxyimino-acetylamino]-3-[(E)-1-(1H-benzimidazol-2-ylmethyl)-2-oxo-pyrrolidin-3-ylidenemethyl]-8-oxo-5-thia-1-aza-bicyclo[4.2.0]oct-2-ene-2-carboxylic acid

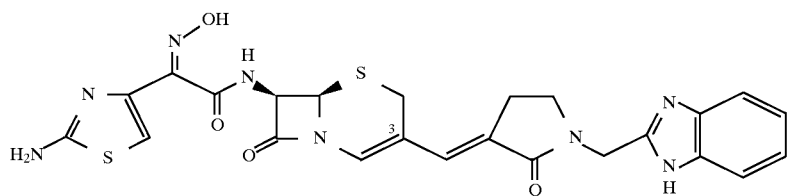

(6R,7R)-7-[(Z)-2-(2-Amino-thiazol-4-yl)-2-hydroxyimino-acetylamino]-8-oxo-3-[(E)-2-oxo-1-piperidin-4-yl-pyrrolidin-3-ylidenemethyl]-5-thia-1-aza-bicyclo[4.2.0]oct-2-ene-2-carboxylic acid

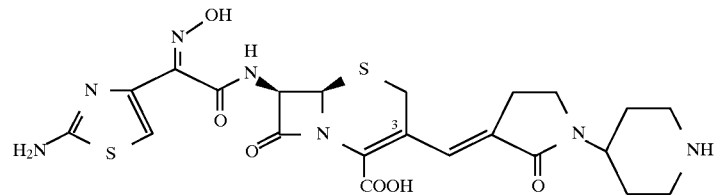

(6R,7R)-7-[(Z)-2-(2-Amino-thiazol-4-yl)-2-hydroxyimino-acetylamino]-8-oxo-3-[(E)-2-oxo-1-(1,3,4-thiadiazol-2-yl)-pyrrolidin-3-ylidenemethyl]-5-thia-1-aza-bicyclo[4.2.0]oct-2-ene-2-carboxylic acid

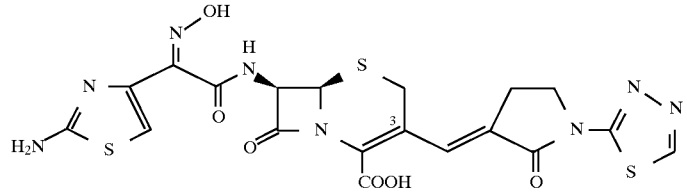

The invention also relates to pharmaceutical compositions and methods of use of the above.

As used herein pharmaceutically acceptable salts useful in this invention include salts derived from metals, the ammonium salt, quaternary ammonium salts derived from organic bases, and amines and amino acid salts. Examples of preferred metal salts are those derived from the alkali metals, for example, lithium ($Li^+$), sodium ($Na^+$) and potassium ($K^+$), and from the alkaline earth metals, for example, calcium ($Ca^{++}$) and magnesium ($Mg^{++}$), although cationic forms of other metals, such as iron ($Fe^{++}$ or $Fe^{+++}$), aluminum ($Al^{+++}$), and zinc ($Zn^{++}$) are within the scope of this invention. Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CH_2CH_3)_3$), and the like. Those salts derived from amines include salts with N-ethyl-piperidine, procaine, dibenzylamine, N,N'-dibenzylethylenediamine, alkylamines or dialkylamines and those derived from amino acids include, for example, salts with arginine or lysine.

As readily hydrolyzable esters of the compounds of formula I there are to be understood compounds of formula I, the carboxy group(s) of which is/are present in the form of readily hydrolyzable ester groups. Examples of such esters, which can be of the conventional type, are the lower alkanoyloxy-alkyl esters (e.g., the acetoxymethyl, pivaloyloxy-methyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropyloxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methylpropoxy)carbonyl]-2-pentenyl ester; 1-[[(1-methylethoxy)carbonyl]oxy] ethyl ester; 1-(acetyloxy) ethyl ester; (5-methyl-2-oxo-1,3-dioxol-4-yl) methyl ester; 1-[[(cyclohexyloxy)carbonyl]oxy] ethyl ester; and 3,3-dimethyl-2-oxobutyl ester. It will be appreciated by those of ordinary skill in the art that the readily hydrolyzable esters of the compounds of the present invention can be formed at a free carboxy group of the compound, for example, at the carboxy group in position 2.

The compounds of formula I as well as their salts and readily hydrolyzable esters can be hydrated. The hydration can be effected in the course of the manufacturing process or can occur gradually as a result of hygroscopic properties of an initially anhydrous product.

The compounds of the present invention are useful as antibiotics having potent and broad antibacterial activity. They also possess good oral absorption properties.

The products in accordance with the invention can be used as medicaments, for example, in the form of pharmaceutical preparations for enteral (oral) administration. The products in accordance with the invention can be administered, for example, perorally, such as in the form of tablets, coated tablets, dragees, hard and soft gelatine capsules, solutions, emulsions or suspensions, or rectally, such as in the form of suppositories.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral or parenteral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatine capsules there can be used, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case of soft gelatine capsules). Suitable carrier materials for the preparation of solutions and syrups are, for example, water, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorants, salts for varying the osmotic pressure, buffers, coating agents and antioxidants.

The compounds of formula I and their salts, or hydrates, can preferably be used for parenteral administration, and for this purpose are preferably made into preparations as lyophilisates or dry powders for dilution with customary agents, such as water or isotonic common salt solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds of the present invention were tested.

In vitro activity was determined by minimum inhibitory concentration in a microorganism spectrum by the agar dilution method in Mueller Hinton agar.

The following compounds were tested:

A: (6R,7R)-7-[(Z)-2-(2-Amino-thiazol-4-yl)-2-hydroxyimino-acetylamino]-3-[(E)-1-(4-hydroxy-phenyl)-2-oxo-pyrrolidin-3-ylidenemethyl]-8-oxo-5-thia-1-azabicyclo[4.2.0]oct-2-ene-2-carboxylic acid.

B: (6R,7R)-7-[(Z)-2-(2-Amino-thiazol-4-yl)-2-(hydroxyimino-acetylamino]-3-[(E)-1-(3-nitro-phenyl)-2-oxo-pyrrolidin-3-ylidenemethyl]-8-oxo-5-thia-1-azabicyclo[4.2.0]oct-2-ene-2-carboxylic acid.

C: (6R,7R)-7-[(Z)-2-(2-Amino-thiazol-4-yl)-2-(hydroxyimino-acetylamino]-3-[(E)-1-(3-fluoro-4- hydroxy-phenyl)-2-oxo-pyrrolidin-3-ylidenemethyl]-8-oxo-5-thia-1-azabicyclo[4.2.0]oct-2-ene-2-carboxylic acid trifluoroacetate.

D: (6R,7R)-7-[(Z)-2-(2-Amino-thiazol-4-yl)-2-(hydroxyimino-acetylamino]-3-[(E)-1-(4-aminobenzyl)-2-oxo-pyrrolidin-3-ylidenemethyl]-8-oxo-5-thia-1-azabicyclo[4.2.0-]oct-2-ene-2-carboxylic acid trifluoroacetate.

E: (6R,7R)-7-[(Z)-2-(2-Amino-thiazol-4-yl)-2-(hydroxyimino-acetylamino]-3-[(E)-1-(3-hydroxybenzyl)-2-oxo-pyrrolidin-3-ylidenemethyl]-8-oxo-5-thia-1-azabicyclo[4.2.0]oct-2-ene-2-carboxylic acid trifluoroacetate.

F: (6R,7R)-7-[(Z)-2-(2-Amino-thiazol-4-yl)-2-hydroxyimino-acetylamino]-8-oxo-3-[(E)-2-oxo-1-(1,3,4-thiadiazol-2-yl)-pyrrolidin-3-ylidenemethyl]-5-thia-1-aza-bicyclo[4.2.0]oct-2-ene-2-carboxylic acid trifluoracetate (1:1).

G: (6R,7R)-7-[(Z)-2-(2-Amino-thiazol-4-yl)-2-hydroxyimino-acetylamino]-8-oxo-3-[(E)-2-oxo-1-piperidin-4-yl-pyrrolidin-3-ylidenemethyl]-5-thia-1-aza-bicyclo[4.2.0-]oct-2-ene-2-carboxylic acid hydrochloride (1:2).

H: (6R,7R)-7-[(Z)-2-(2-Amino-thiazol-4-yl)-2-hydroxyimino-acetylamino]-3-[(E)-1-(1H-benzimidazol-2-ylmethyl)-2-oxo-pyrrolidin-3-ylidenemethyl]-8-oxo-5-thia-1-aza-bicyclo[4.2.0]oct-2-ene-2-carboxylic acid trifluoroacetate (1:1:1).

The antibacterial spectrum appears below:

| | Antibacterial Spectrum (MIC, μg/ml) | | | | | | | | | |
|---|---|---|---|---|---|---|---|---|---|---|
| | A | B | C | D | E | F | G | H | I | II |
| S. aureus 6538 | 0.25 | 0.25 | 0.5 | 1 | 0.5 | 1 | 1 | 1 | 0.5 | 4 |
| S. aureus 734 MRSA | 4 | 4 | 4 | 8 | 16 | 16 | 8 | 8 | >32 | >32 |
| S. pyogenes B15 | ≤0.006 | ≤0.006 | ≤0.006 | ≤0.006 | ≤0.12 | £0.06 | £0.06 | £0.06 | ≤0.006 | ≤0.006 |
| S. pneumoniae Q19 | 0.12 | ≤0.006 | ≤0.006 | ≤0.006 | ≤0.006 | £0.06 | £0.12 | £0.12 | 0.25 | ≤0.006 |
| S. agalactiae QK44 | 0.25 | 0.5 | 0.06 | 0.25 | 0.12 | 0.25 | 0.25 | 0.25 | 0.25 | ≤0.006 |
| S. viridans group 016 | 0.25 | 1 | 0.12 | 0.5 | 0.5 | 0.5 | £0.12 | 0.5 | 2 | 0.25 |
| E. faecalis 6 | 0.5 | 0.25 | 1 | 1 | 0.5 | 1 | 1 | 2 | 8 | >32 |
| L. monocytogenes BK23 | 4 | 4 | 1 | 4 | 2 | 4 | 4 | 4 | 16 | >16 |
| H. influenzae 1 | 0.25 | 0.5 | nd | nd | nd | nd | nd | nd | 0.5 | <0.06 |
| M. catarrhalis RA21 | 16 | >16 | nd | 4 | 2 | >16 | 2 | 4 | 1 | 1 |
| N. meningitidis 69480 | ≤0.006 | ≤0.006 | nd | nd | nd | nd | nd | nd | ≤0.006 | <0.061 |
| E. coli 25922 | ≤0.006 | 0.12 | 0.12 | 0.25 | ≤0.12 | 0.12 | £0.06 | 0.12 | 0.25 | ≤0.006 |
| K. pneumoniae 418 | ≤0.006 | 0.25 | 0.12 | 0.25 | 0.25 | 0.25 | £0.06 | 0.12 | 0.12 | ≤0.006 |
| E. cloacae 908SSi | 0.25 | 0.25 | 0.5 | 0.5 | 0.5 | 1 | 0.25 | 0.5 | 32 | 0.25 |
| E. cloacae 908R | 16 | 2 | 32 | >32 | 8 | >32 | 4 | 4 | >32 | >32 |
| C. freundii 902 | nd | 0.12 | 0.12 | 0.25 | 0.25 | 0.12 | £0.06 | 0.12 | 16 | 0.25 |
| C. freundii 43 | 4 | 1 | 4 | 8 | 4 | 8 | 2 | 2 | >32 | 32 |
| P. mirabilis 2117 | ≤0.006 | 0.12 | ≤0.006 | 0.12 | ≤0.006 | 0.25 | £0.06 | 0.25 | 0.12 | ≤0.006 |
| P. vulgaris 1028 | 32 | 16 | 8 | >32 | 16 | >32 | >32 | 16 | 1 | 0.12 |
| M. morganii 6H-137 | ≤0.006 | ≤0.006 | ≤0.006 | 0.12 | ≤0.006 | 0.5 | £0.06 | 0.25 | 8 | ≤0.006 |
| S. marscescens 69438 | 0.5 | 1 | 1 | 1 | 0.5 | 32 | 1 | 1 | 16 | 0.25 |
| P. aeruginosa 27853 | 4 | 16 | 4 | >32 | 8 | >32 | 8 | >32 | >32 | 16 |
| X. maltophilia 1AC739 | >32 | >32 | >32 | >32 | >32 | >32 | >32 | >32 | >32 | >32 |
| Acinetobacter sp. 51–156 | 16 | 16 | 32 | 32 | 32 | >32 | 32 | >32 | >32 | 32 |
| B. fragilis ATCC25285 | 4 | 2 | nd | 8 | 8 | nd | 16 | 8 | | |
| P. asaccharolyticus 29743 | 0.25 | ≤0.12 | nd | 1 | ≤0.12 | nd | 1 | 1 | | |
| C. difficile ZH1 | 8 | 16 | nd | 16 | 4 | nd | 16 | 16 | | |

MIC: Minimum Inhibiting Concentration Values
I (Cefdinir): [6R-[6a,7b(Z)]]-7-(2-Amino-4-thiazolyl)[(hydroxyimino)]acetyl]amino]-3-ethenyl-8-oxo-5-thia-1-azabicyclo-[4.2.0]oct-2-ene-2-carboxylic acid
II (Ceftriaxone): [6R-[6a,7b(Z)]]-7-([[2-Amino-4-thiazolyl)(methoxyimino)acetyl] amino]-8-oxo-3-[[(1,2,5,6-tetrahydro-2-methyl-5,6-dioxo-1,2,4-triazin-3-yl)thio]methyl]-5-thia-1-azabicyclo[4.2.0]oct-2-ene-2-carboxylic acid
nd: not determined The compounds of the formula I in accordance with the invention as well as their pharmaceutical acceptable salts, hydrates, or readily hydrolyzable esters can be made in accordance with the invention by (a) treating a compound having the formula II

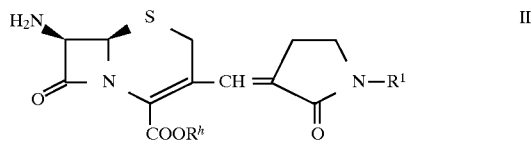

II in which R¹ is as defined for formula I, and $R^h$ is hydrogen or a carboxy protecting group or an ester or salt thereof, with an acylating agent of the general formula III

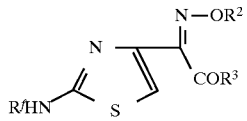

in which

R² is hydrogen or a hydroxy protecting group; and

R³ is hydroxy or an activating group such as 1-hydroxybenzotriazole or 2-benzothiazolylthio, $R^f$ is hydrogen or an amino protecting group or (b) cleaving off the amino, hydroxy and/or carboxy protecting group in a compound having the formula IV

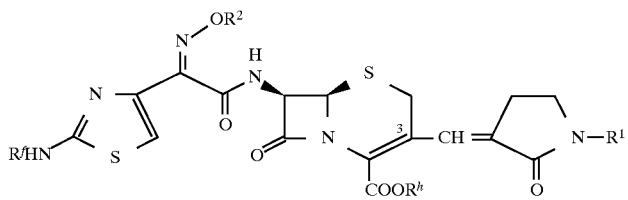

in which R¹ is defined as above, $R^f$ is hydrogen or an amino protecting group, R² is hydrogen or a hydroxy protecting group, $R^h$ is hydrogen or a carboxy protecting group, provided that at least one of $R^f$, R² and $R^h$ is a corresponding protecting group or a salt thereof, or (c) for making of a readily hydrolyzable ester of a compound of formula I subjecting a carboxylic acid of formula I to a corresponding esterification, or (d) for making of salts or hydrates of a compound of formula I or hydrates of said salts converting a compound of formula I into a salt or hydrate or into a hydrate of said salts.

The carboxy group in the compounds of formulae II and IV can be protected; for example, by esterification to form a readily cleavable ester such as a silyl ester (e.g. the trimethylsilyl ester) or benzhydryl ester. The carboxy group can also be protected in the form of one of the aforementioned readily hydrolyzable esters. Furthermore, the carboxy group can be protected by salt formation with an inorganic or tertiary organic base such as triethylamine.

Possible carboxy protecting groups $R^h$ are e.g. benzhydryl, t-butyl, p-nitrobenzyl, p-methoxybenzyl, allyl.

The 7-amino group in the compounds of formula II can be protected, for example, by a silyl protecting group such as the trimethylsilyl group.

The amino group present in the acylating agent of formula III can be protected.

Possible amino protecting groups $R^f$ are, for example, protecting groups which are cleavable by acid hydrolysis (e.g. the tert.butoxycarbonyl or trityl group) or by hydrazinolysis (e.g. the phthalimido group). Other protecting groups are the phenylacetyl group, the chloroacetyl, bromoacetyl and iodoacetyl group.

The carboxy group in the compounds of formula III can be activated with known reagents, preferably thionyl chloride, oxalyl chloride, dicyclohexylcarbodiimide, bis-[benzthiazolyl-(2)]disulfide, N-hydroxy benzotriazole or a 2-halo N-methylpyridinium salt.

Possible activating groups R³ are, for example, benzothiazolyl-2-thio, or 1-hydroxybenzotriazolyl.

Possible hydroxy protecting groups R² are, for example, acetyl, tetrahydropyranyl, or trityl.

The reaction of compounds of the formulae II and III according to embodiment (a) can be carried out in a manner known per se.

For example, an activated carboxylic acid of the formula III can be reacted with a salt of an acid of the formula II (e.g. trifluoracetate). The reaction is carried out with or without a base (inorganic or organic bases) depending on the method of activation and a wide range of solvents, from water and water-miscible solvent to inert solvents such as chloroform, dimethylformamide (DMF) or dimethylsulfoxide (DMSO) can be used.

The reaction of a 7-amino compound of formula II with the activated carboxylic acid of formula III can conveniently be carried out at a temperature between about −40° C. and +60° C., e.g. at room temperature.

Embodiment (b) of the process of the present invention involves deprotection (removal of protecting groups) of protected amino, hydroxy or carboxylic groups present in a compound of formula IV and can be carried and as follows:

Removal of amino protecting groups

Possible amino-protecting groups are those employed in peptide chemistry, such as an alkoxycarbonyl group, e.g., tert-butoxycarbonyl, etc., a substituted alkoxycarbonyl group, e.g., trichloroethoxycarbonyl etc., an optionally substituted aralkyloxycarbonyl group, e.g., 4-nitrobenzyloxycarbonyl or benzyloxycarbonyl, an aralkyl group such as trityl or benzhydryl or a halogen-alkanoyl group such as chloroacetyl, bromoacetyl, iodoacetyl, trifluoroacetyl or phenylacetyl.

Preferred protecting groups are tert-butoxycarbonyl (t-BOC) and trityl.

The amino protecting groups may be cleaved off by acid hydrolysis (e.g. the tert-butoxycarbonyl or trityl group), e.g. aqueous formic acid. The chloroacetyl, bromoacetyl and iodoacetyl groups are cleaved off by treatment with thiourea and the phenylacetyl group by treatment with $PCl_5$ or by enzymatic catalysis.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to +40° C.). The chloroacetyl, bromoacetyl and iodoacetyl protecting groups can be cleaved off using thiourea in acidic, neutral or alkaline medium at about 0° C.–30° C., phenylacetyl by treatment with $PCl_5$.

Removal of hydroxy protecting groups

Possible hydroxy protecting groups are such as are commonly known in the art, e.g. for protection of hydroxy groups (R²=protecting group in compounds of formula IV), usually trityl, lower alkanoyl, preferably acetyl, tetrahydropyranyl protecting groups are employed.

These protecting groups are e.g. removed as follows:

trityl in acidic solvents like 90% formic acid at about 0° to 50° C. or triethylsilane in trifluoroacetic acid at about −20° to 25° C.;

in organic solutions of hydrochloric acid at about −50° to 25° C.;

acetyl with weak inorganic bases like sodium bicarbonate in methanol/water at about 0° to 50° C.;

tetrahydropyranyl with weak organic acids like 4-toluenesulfonic acid in an alcohol, e.g. methanol or ethanol, at about 0° C. to the boiling point of the mixture.

Removal of protecting groups at the carboxy function

As ester protecting groups one may utilize an ester form which can be easily converted into a free carboxyl group under mild conditions, the ester protecting group being exemplified by, for example, tert-butyl, 4-nitrobenzyl, p-methoxybenzyl, benzhydryl, allyl, etc.

These protecting groups may be removed as follows:

benzhydryl trifluoroacetic acid with anisol, phenol, cresol or triethylsilane at about −40° C. to room temperature;

hydrogen with Pd/C in an alcohol such as ethanol or in tetrahydrofuran; $BF_3$-etherate in acetic acid at about 0° to 50° C.;

tert-butyl formic acid or trifluoroacetic acid with or without anisol, phenol, cresol or triethylsilane and a solvent such as dichloromethane at about −10° C. to room temperature;

4-nitrobenzyl sodium sulfide in acetone/water at about 0 to room temperature; or hydrogen with Pd/C in an alcohol such as ethanol or in tetrahydrofuran;

4-methoxybenzyl formic acid at about 0° to 50° C.; or trifluoroacetic acid and anisol, phenol or triethylsilane at about −40° C. to room temperature;

allyl palladium(O) catalyzed transalkylation reaction in the presence of e.g. sodium or potassium salt of 2-ethyl hexanoic acid, see for example J. Org. Chem. 1982, 47, 587 or with tributyl-stannous hydride [$(C_4H_9)_3SnH$].

In order to make a readily hydrolyzable ester of the carboxylic acids of formula I in accordance with embodiment (c) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0°–40° C.

The making of the salts and hydrates of the compounds of formula I or the hydrates of said salts in accordance with embodiment (d) of the process provided by the present invention can be carried out in a manner known per se; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic salt. The temperature at which the salt formation is carried out is not critical. The salt formation is generally carried out at room temperature, but it can be carried out at a temperature slightly above or below room temperature, for example in the range of 0° C. to +50° C.

The making of the hydrates usually takes place automatically in the course of the process or as a result of the hygroscopic properties of an initially anhydrous product. For the controlled making of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction schemes 1 and 2 below.

Scheme 1

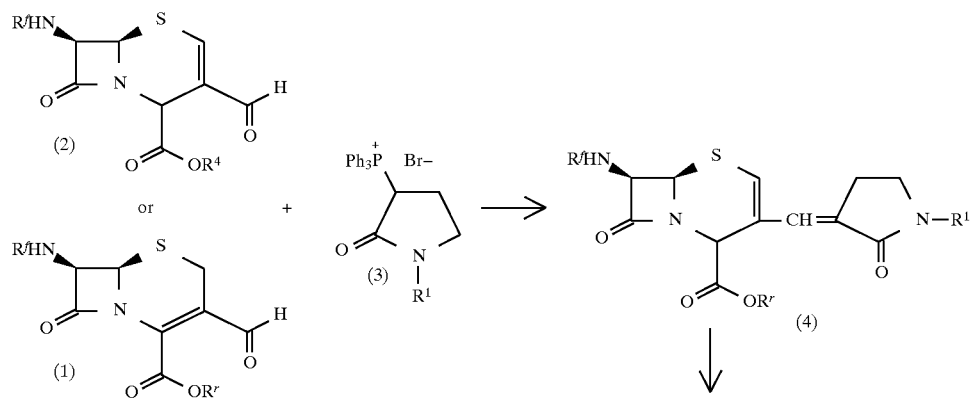

-continued
Scheme 1

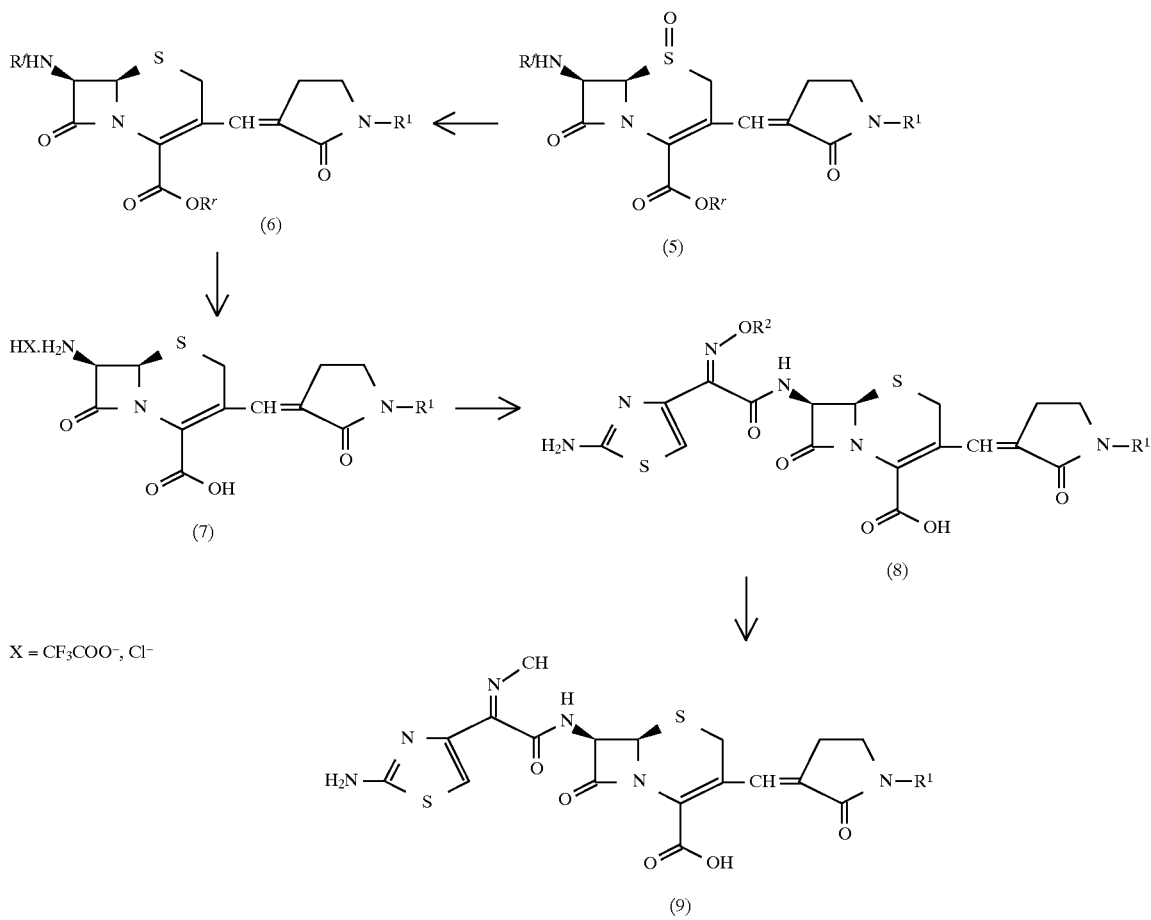

X = CF$_3$COO$^-$, Cl$^-$ 1 or 2+3→4

The reaction of known 2-cephem aldehyde (1) or 3-cephem aldehyde (2) where R$^r$ is a carboxy protecting group as defined above, e.g. benzhydryl ester, and R$^f$ is an amino protecting group as defined above, e.g. tert.butylcarbonyl, with a Wittig reagent, exemplified by structure 3, yields the coupling product 4. The reaction is carried out in the presence of a base which is either an inorganic base (sodium or potassium hydroxide, sodium or potassium carbonate etc.), an organic base (tertiary amines), an organolithium such as butyl lithium or phenyllithium or an epoxide such as 1,2-butyleneoxide. The reaction in presence of an epoxide is preferred. The preferred solvents, in the case of inorganic base being used, are water and water-miscible solvent (acetone, tetrahydrofuran, or alcohols etc.); in the case of organic base being used, an inert solvent such as methylene chloride, chloroform, benzene, tetrahydrofuran; in the case of organolithium being used, benzene or tetrahydrofuran; and in the case an epoxide being used, the epoxide itself (e.g. 1,2-butyleneoxide). The temperature for the reaction ranges from −20° C. to 80° C. The preferred conditions are exemplified in the examples.

In the normal Wittig Reaction according to scheme 1, the E isomer is the predominant product. Invariably, less than 10% Z-isomer is formed, the amount depending on the reagents and conditions.

4→5

Compound 4 is converted to the sulfoxide 5 with an oxidizing agent which can be hydrogen peroxide or a peracid, preferably 3-chloroperbenzoic acid. The temperature ranges from −20° C. to room temperature and any suitable solvent, preferably chlorinated hydrocarbon or benzene can be used.

5→6

The de-oxygenation of the sulfoxide 5 is carried out in the presence of phosphorus tribromide in dimethylformamide or in the mixed solvent of dimethylformamide and N-methylacetamide. The reaction temperature for the reaction is from about −78° C. to about 0° C.

6→7

The protecting groups R$^r$ and R$^f$ are removed and the reaction conditions used are depending on the nature of the protecting groups. In the case of R$^f$ being tert-butoxycarbonyl and R$^r$ being benzhydryl, trifluoroacetic acid and anisole or triethylsilane is employed, at temperature of about −20° C. to about room temperature (about 22° C.).

7→8

The acylation of compound 7 can be carried out with an organic acid which is activated with known reagents, preferably thionyl chloride, oxalyl chloride, dicyclohexylcarbodiimide, bis-[benzthiazolyl-(2)]disulfide, N-hydroxy-benzotriazole or a 2-halo N-methylpyridinium salt. The reaction is carried out with or without the base (inorganic or organic bases) depending on the method of activation and a wide range of solvents, from water and water-miscible solvent to inert solvents such as chloroform, dimethylformamide (DMF) or dimethylsulfoxide (DMSO) can be used. The substituents in the R$^1$ group, if necessary, can be further deprotected with a reaction condition suitable for the removal of the protecting group.

8→9

The hydroxy protecting group $R^2$ group is removed with trifluoroacetic acid and triethylsilane or 90% formic acid.

The Wittig reagent is prepared according to scheme 2

Scheme 2

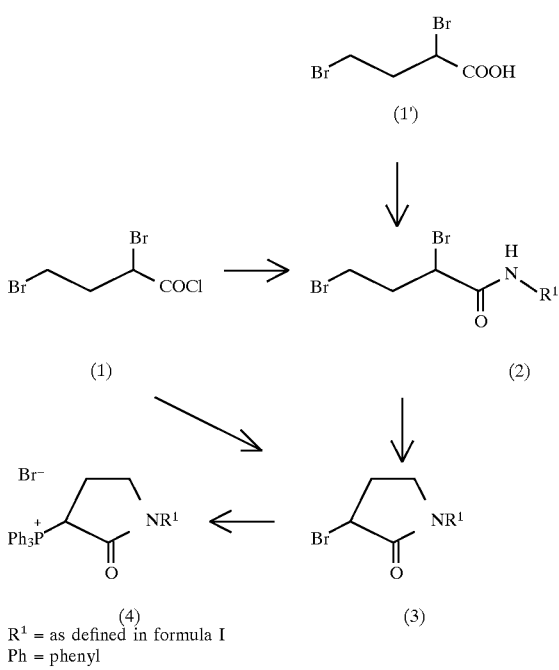

$R^1$ = as defined in formula I
Ph = phenyl

The processes in scheme 2 are carried out as follows:

1→2

The known dibromo acid chloride (1) can be converted to the amides (2) using the appropriate amines or aminehydrohalides and inorganic bases such as sodium or potassium hydroxide, sodium or potassium carbonate etc., organic bases such as sodium methoxide, pyridines or tertiary amines such as triethylamine, diisopropylethylamine etc. The reaction is carried out in biphasic solvent mixtures like water/dichloromethane or water/chloroform etc., when inorganic bases are used. In case of organic bases or tertiary amines being used, an inert solvent such as methylene chloride, chloroform, benzene, tetrahydrofuran etc. is preferred. The reaction-temperatures range from −10° C. to 100° C.

1'→2

The known dibromo acid (1') which is activated with known reagents, e.g. with dicyclohexylcarbodiimide can be converted to the amides (2) using the appropriate amines and organic bases such as dimethylaminopyridine. The reaction is carried out in an inert solvent such as dimethylformamide, dichloromethane or acetonitrile.

2→3

Cyclization of the N-substituted dibromoamides (2) can be accomplished under the usual phase transfer catalytic conditions using catalysts like Dowex 2×10, tetraalkylammonium salts, tetraalkylarylammonium salts, crown ethers etc. with bases like aqueous sodium or potassium hydroxide, sodium or potassium carbonate etc.

Alternatively, strong bases like sodium hydride, lithium diisopropylamide, potassium tert-butoxide can be used in solvents like tetrahydrofuran, dichloromethane, dimethoxyethane or diethylether at reaction temperatures between −78° C. and +80° C.

1→3

The direct conversion of the acid chlorides into the bromolactams is possible when the first step (1 Æ 2) is carried out in biphasic solvent mixtures like water/dichloromethane or water/chloroform etc. together with sodium or potassium hydroxide as base. A catalyst like Dowex 2×10, tetralkylammonium salts, tetraalkylarylammonium salts, crown ethers etc. is added when the amide (2) has formed according to TLC or HPLC analysis. The temperatures range between 0° C. and 50° C.

Alternatively, the direct conversion of the acid chlorides into the bromolactams can be carried out without catalyst using the appropriate amino-compound in an organic base such as pyridine, dimethylamino-pyridine, triethylamine or in aqueous potassium carbonate.

3→4

The triphenylphosphonium salts (4) can be prepared by treating the bromolactams with triphenylphosphine in solvents like tetrahydrofuran, toluene, benzene, ethylacetate, dichloromethane, dichloroethane, chloroform, acetone etc. at temperatures between 0° and 150° C.

EXAMPLES

1. Conversion of a Dibromo acid chlorides to the amides (Scheme 2, 1→2)
1.1. Using an organic base
1.1.1. Preparation of carbonic acid (RS)-4-(2,4-dibromo-butyrylamino)-phenyl ester tert-butyl ester

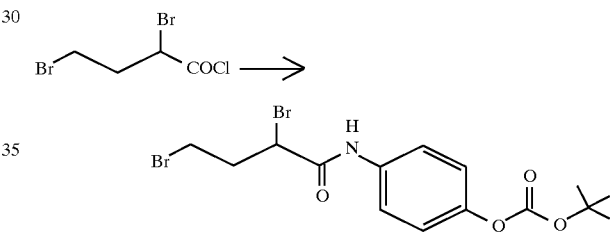

To a solution of 15.7 g (75 mmol) carbonic acid-(4-amino-phenyl)-ester tert-butyl ester (prepared according to Can. J. Chem. 63, 153 (1985)) in 200 ml dichloromethane and 11.13 ml (80 mmol) triethylamine was added a solution of 21.15 g (80 mmol) 2,4-dibromobutanoic acid chloride[1]) in 100 ml dichloromethane at −20° to −10° C. After 30 min the reaction mixture was extracted with water, the organic phase was dried over magnesium sulfate. After evaporation of the solvent, a colorless oil was obtained which was crystallized with diethylether/hexane to yield 21.24 g (66.8%) colorless crystals.

[1]) H. Ikuta et al., J. Med. Chem., 30, 1995 (1987)

m.p. 105°–106° C.; IR (KBr): 1758, 1682 cm$^{-1}$ 1.1.2. (RS)-4-(2,4-Dibromo-butyrylamino)-piperidine-1-carboxylic acid ethyl ester

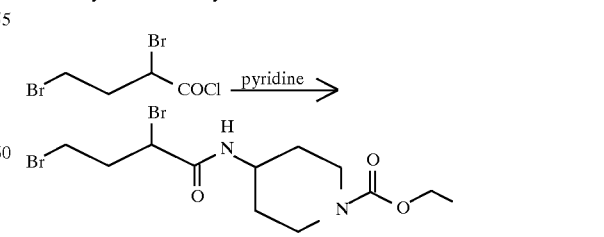

To a solution of 23.3 g (141 mmol) ethyl 4-aminopiperidine-1-carboxylate in 400 ml dichloromethane and 11.1 g (141 mmol) pyridine cooled to −10°

C. was added within 30 min dropwise a solution of 33.5 g (128 mmol) 2,4-dibromobutanoic acid chloride[1] in 130 ml dichloromethane. After 40 min at 0° C., 350 ml of water were added, the organic solution was separated and washed with water, sodium bicarbonate solution and brine and dried over sodium sulfate. After evaporation of the solvent, a red oil was obtained which was crystallized from diethyl ether.

[1] H. Ikuta et al., J. Med. Chem., 30, 1995 (1987)

yield 39.5 g (73%) yellowish crystals
m.p. 124°–126° C.
IR (KBr): 1695, 1656, 1553 cm$^{-1}$, MS(EI): 318 (M–HBr)$^+$ According to the procedure set forth in the preceding example, the following additional compounds were prepared:

1.1.3. (RS)-2,4-Dibromo-N-(3-nitro-phenyl)-butyramide
m.p. 75°–76° C., IR (KBr): 1677 cm$^{-1}$, MS (EI) 366 (M)$^+$ 1.1.4. (RS)-4-(2,4-Dibromo-butyrylamino)-piperidine-1-carboxylic acid allyl ester
IR (KBr): 1687, 1650, 1557 cm$^{-1}$, MS (ISP): 412.9 (M+H)$^+$ 1.2. using an organic base
1.2.1. Preparation of (RS)-2,4-Dibromo-N-(4-nitro-benzyl)-butyramide

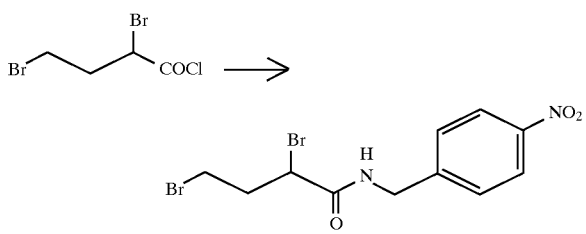

To a solution of 15.7 g (83.2 mmol) 4-nitrobenzylamine-hydrochloride in 9 ml water was added 46 ml dichloromethane and the mixture was vigorously stirred. At 0° C., a solution of 20 g (75.7 mmol) 2.4-dibromobutanoic acid chloride[1] in 11 ml dichloromethane was added, followed by a solution of 7 g sodium hydroxide in 11 ml water. After 5 h, the phases were separated and the aqueous phase was extracted with dichloromethane. The combined organic solutions were washed with 10% sodium bicarbonate solution and brine and were dried over magnesium sulfate. Evaporation of the solvent yielded an oil which was purified by silica gel chromatography (ethyl acetate:hexane=1:1); yield: 22.1 g (70%) colorless crystals; IR(KBr): 1655, 1515 cm$^{-1}$; MS(EI): 299 (M–Br)

[1] H. Ikuta et al., J. Med. Chem., 30, 1995 (1987)

1.2.2. (RS)-2,4-Dibromo-N-(1H-benzimidazol-2-ylmethyl)-butyramide

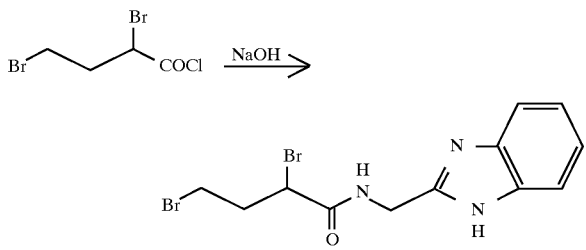

To a solution of 10.8 g (45.4 mmol) 2-(aminomethyl)-benzimidazol-dihydrochloride in 5 ml water was added 25 ml dichloromethane and the mixture was vigorously stirred. At 0° C., a solution of 10.9 g (41.2 mmol) 2,4-dibromobutanoic acid chlorides) in 10 ml dichloromethane was added, followed by a solution of 5.45 g sodium hydroxide in 10 ml water. After 1.5 h, the mixture was poured on water. Ethyl acetate was added and the phases were separated. The aqueous phase was extracted with ethyl acetate and the combined organic phases were washed with water and brine and were dried over magnesium sulfate. Upon concentration the product started to crystallize from the solution. It was collected by filtration, washed with ethyl acetate and dried.

[1] H. Ikuta et al., J. Med. Chem., 30, 1995 (1987)

yield: 11.52 g (75%) colorless crystals
IR(KBr): 1660, 1625, 1533 cm$^{-1}$, MS(EI): 375 (M$^+$)

According to the procedure set forth in the preceding examples, the following additional compounds were prepared:

1.2.3. (RS)-2,4-Dibromo-N-naphthalen-2-yl-butyramide
IR (KBr): 1659, 1560 cm$^{-1}$, MS (EI): 371 (M)$^+$ 1.2.4. (RS)-4-(2,4-Dibromo-butyrylamino)-N-trityl-benzamide
IR (KBr): 1656, 1486 cm$^{-1}$, MS (EI): 606 (M)$^+$ 1.2.5. Mixture of (RS)- and (SR)—[(RS)-2,4-dibromo-butyrylamino]-phenyl-acetic acid tert-butyl ester
IR (KBr): 1724, 1665, 1520 cm$^{-1}$, MS (EI): 334 (M—COOtBu)

1.2.6. (RS)-2,4-Dibromo-N-(2-fluoro-benzyl)-butyramide
IR (KBr): 3273, 1649, 1550 cm$^{-1}$, MS (EI): 272 (M–Br)

1.2.7. (RS)-2,4-Dibromo-N-(2-methoxy-benzyl)-butyramide
IR (KBr): 3282, 1643, 1545 cm$^{-1}$, MS (EI): 284 (M–Br)

1.2.8. (RS)-2,4-Dibromo-N-(3-fluoro-benzyl)-butyramide
IR (KBr): 3289, 1658, 1551 cm$^{-1}$, MS (EI): 272 (M–Br)

1.2.9. (RS)-2,4-Dibromo-N-(3-methoxy-benzyl)-butyramide
IR (KBr): 3287, 1658, 1601 cm$^{-1}$, MS (ISP): 366.2 (M–H)$^+$ 1.2.10. (RS)-[4-[(2,4-Dibromo-butyrylamino)-methyl]-phenyl]-carbamic acid tert-butyl ester
IR (KBr): 1700, 1663, 1529 cm$^{-1}$, MS (ISP): 468 (M+NH$_4$)$^+$ 1.2.11. (RS)-4-[(2,4-Dibromo-butyrylamino)-methyl]-benzoic acid tert-butyl ester
IR (KBr): 3300, 1712, 1661 cm$^{-1}$, MS (EI): 354 (M–Br)

1.2.12. (RS)-2,4-Dibromo-N-(4-methoxy-benzyl)-butyramide
IR (KBr): 3279, 1647, 1549 cm$^{-1}$, MS (EI): 284 (M–Br)

1.2.13. (RS)-2,4-Dibromo-N-(4-fluoro-benzyl)-butyramide
IR (KBr): 3284, 1676, 1644, 1611 cm$^{-1}$, MS (EI): 272 (M–Br)

1.2.14. (RS)-2,4-Dibromo-N-(4-trifluoromethyl-benzyl)-butyramide
IR (KBr): 3294, 1655, 1568 cm$^{-1}$, MS (EI): 322 (M–Br)

1.2.15. (RS)-N-Benzyl-2,4-dibromo-butyramide
m.p. 76.2°–77.0° C.
IR (KBr): 3277, 1647, 1545 cm$^{-1}$, MS (EI): 256 (M–Br)

1.2.16. (RS)-2,4-Dibromo-N-thiophen-2-ylmethyl-butyramide
IR(KBr): 3269, 1645, 1542 cm$^{-1}$, MS(EI): 260 (M–Br)$^+$ 1.2.17. Mixture of (RS)- and (SR)-2,4-Dibromo-N-[(RS)-tetrahydro-furan-2-ylmethyl]-butyramide
IR(KBr): 3298, 1662, 1549 cm$^{-1}$, MS(ISP): 330.1 (M+H)$^+$ 1.2.18. (RS)-2,4-Dibromo-N-(1-trityl-1H-tetrazol-5-ylmethyl)-butyramide
MS(ISP): 570.3 (M+H)$^+$ 2. Conversion of a Dibromo acid to the amides (Scheme 2, 1'→2)

2.1. (RS)-2,4-Dibromo-N-(6-chloro-pyridazin-3-yl)-butyramide

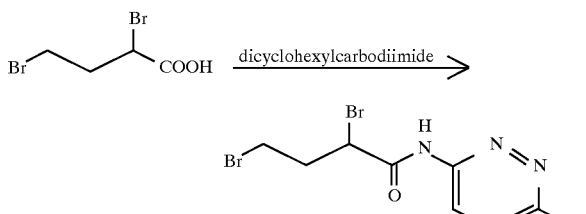

42.4 g (207 mmol) N,N'-dicyclohexylcarbodiimid was added at room temperature to a stirred solution of 24.5 g (189 mmol) 3-amino-6-chloropyridazine, 46.3 g (189 mmol) 2,4-dibromobutanoic acid and 0.5 g (4 mmol) 4-dimethylamino-pyridine in 550 ml dimethylformamide. After 2.5 h the slurry was filtered and the residue washed thoroughly with ethyl acetate. The filtrate was diluted with 1 l ethyl acetate, washed with water and brine, dried over sodium sulfate and evaporated. The crude product was purified by silica gel chromatography (hexane:ethyl acetate 4:1).

Yield: 57.0 g (85%)
mp: 126°–127.5° C. (sample recrystallized from ethyl acetate).
IR(KBr): 1706, 1584, 1519 cm$^{-1}$, MS(EI): 357 (M$^+$)

According to the procedure set forth in the preceding example, the following additional compounds were prepared:

2.2. (RS)-2,4-Dibromo-N-(3,5-dimethyl-pyrazin-2-yl)-butyramide
IR(KBr): 1668 cm$^{-1}$, MS(EI): 351 (M$^+$)

2.3. Mixture of (RS)- and (SR)-2,4-dibromo-N-[(RS)-2-oxo-tetrahydro-furan-3-yl]-butyramide
IR(KBr): 1768, 1653, 1554 cm$^{-1}$, MS(EI): 221 (M−CH$_2$=CHBr)$^+$ 2.4. (RS)-2,4-Dibromo-N-(2-chloro-pyridin-3-yl)-butyramide
IR(neat): 1683 cm$^{-1}$, MS(EI): 356 (M$^+$)

3. Cyclization of the N-substituted dibromoamides (Scheme 2, 2→3)

3.1. Preparation of carbonic acid (RS)-4-(3-bromo-2-oxo-pyrrolidin-1-yl)-phenyl ester tert-butyl ester

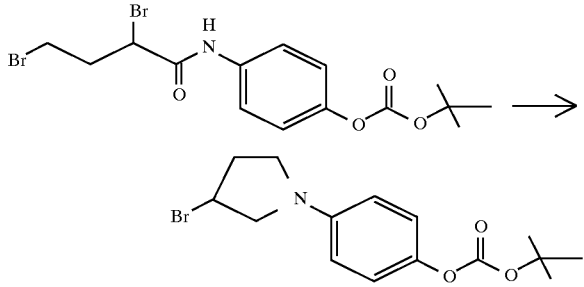

1.8 g Dowex 2×10 was added to a vigorously stirred mixture of 18.39 g (42.86 mmol) carbonic acid (R,S)-4-(2,4-dibromo-butyrilamino)-phenylester tert-butyl ester in 200 ml dichloromethane and 15 g 50% sodium hydroxide solution. After 4 h at rt (room temperature) the mixture was washed twice with water and the organic phase dried over magnesium sulfate. Evaporation of the solvent yielded 14.6 g (97%) of the product as colorless crystals.
mp. 148°–150° C.; IR (KBr): 1751, 1697 cm$^{-1}$ 3.2. (RS)-3-Bromo-1-(1H-benzimidazol-2-ylmethyl)-pyrrolidin-2-one

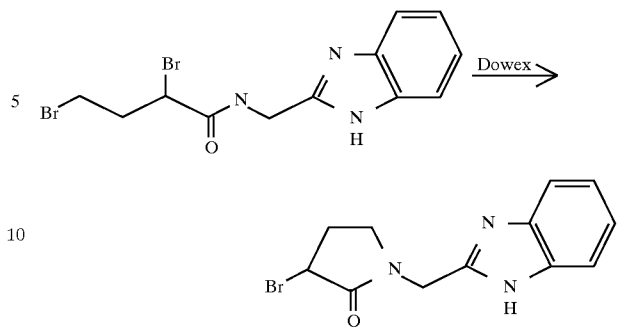

0.98 g Dowex 2×10 was added to a vigorously stirred mixture of 11.52 g (31 mmol) (RS)-2,4-dibromo-N-(1H-benzimidazol-2-ylmethyl)-butyramide in 175 ml ethyl acetate and 36 ml 50% sodium hydroxide solution. After 15 min at room temperature the suspension was poured on a mixture of ice and ethyl acetate and the phases were separated. The aqueous phase was extracted with ethyl acetate and the combined organic phases were washed with water and brine and dried over magnesium sulfate. Upon concentration the product separated from the solution. It was collected by filtration and yielded 7.11 g (79%) of a yellow powder.
IR(KBr): 1698, 1622, 1490 cm$^{-1}$, MS(EI): 293 (M$^+$)

According to the procedure set forth in the preceding examples, the following additional compounds were prepared:

3.3. (RS)-3-Bromo-1-(3-nitro-phenyl)-pyrrolidin-2-one
m.p. 100°–102° C.; IR (KBr): 1703 cm$^{-1}$ 3.4. (RS)-4-(3-Bromo-2-oxo-pyrrolidin-1-yl)-N-tritylbenzamide
IR (KBr): 1730, 1688, 1487 cm$^{-1}$, MS (EI): 524 (M)$^+$ 3.5. (RS)-3-Bromo-1-naphthalen-2-yl-pyrrolidin-2-one
IR (KBr): 1702 cm$^{-1}$, MS (EI): 289 (M)$^+$ 3.6. (RS)-3-Bromo-1-(2-fluoro-benzyl)-pyrrolidin-2-one
IR (KBr): 1703, 1586, 1490 cm$^{-1}$, MS (EI): 192 (M−Br)

3.7. (RS)-3-Bromo-1-(2-methoxy-benzyl)-pyrrolidin-2-one
IR (KBr): 1700, 1602 cm$^{-1}$, MS (EI): 283 (M)$^+$ 3.8. (RS)-3-Bromo-1-(3-methoxy-benzyl)-pyrrolidin-2-one
IR (neat): 1700, 1600 cm$^{-1}$, MS (EI): 283 (M)$^+$ 3.9. (RS)-4-(3-Bromo-2-oxo-pyrrolidin-1-ylmethyl)-benzoic acid tert-butyl ester
IR (neat): 1705, 1612 cm$^{-1}$, MS (EI): 274 (M−Br)

3.10. (RS)-3-Bromo-1-(4-nitro-benzyl)-pyrrolidin-2-one
IR (KBr): 1685, 1604, 1517 cm$^{-1}$, MS (EI): 219 (M−Br)

3.11. (RS)-3-Bromo-1-(4-trifluoromethyl-benzyl)-pyrrolidin-2-one
IR (neat): 1703, 1620 cm$^{-1}$, MS (EI): 242 (M−Br)

3.12. (RS)-1-Benzyl-3-bromo-pyrrolidin-2-one
IR (neat): 1701, 1426 cm$^{-1}$, MS (ISP): 256.3 (M+H)$^+$ 3.13. (3-Bromo-2-oxo-pyrrolidin-1-yl)-phenyl-acetic acid tert-butyl ester (1 config. isomer)
IR (KBr): 1743, 1686 cm$^{-1}$, MS (EI): 252 (M−COOtBu)

3.14. (RS)-[4-(3-Bromo-2-oxo-pyrrolidin-1-ylmethyl)-phenyl]-carbamic acid tert-butyl ester
IR (KBr): 3425, 1692, 1527 cm$^{-1}$, MS (ISP): 289 (M−HBr)

3.15. (RS)-[4-(3-Bromo-2-oxo-pyrrolidin-1-ylmethyl)-phenyl]-carbamic allyl ester
IR (KBr): 3288, 1686, 1536 cm$^{-1}$, MS (CI): 370 (M+NH$_4$)$^+$ 3.16. Mixture of (RS)- and (SR)-3-bromo-1-[(RS)-tetrahydro-furan-2-ylmethyl]-pyrrolidin-2-one
IR(neat): 1698 cm$^{-1}$, MS(ISP): 250.2 (M$^+$H)$^+$ 3.17. (RS)-3-Bromo-1-thiophen-2-ylmethyl-pyrrolidin-2-one IR(neat): 3105, 1699 cm$^{-1}$, MS(EI): 180 (M–Br)$^+$ 3.18. (RS)-3-Bromo-1-(3,5-dimethyl-pyrazin-2-yl)-pyrrolidin-2-one IR(KBr): 1704 cm$^{-1}$, MS(EI): 269 (M$^+$)

3.19. (RS)-3-Bromo-1-(6-Chloro-pyridazin-3-yl)-pyrrolidin-2-one

IR(KBr): 1717 cm$^{-1}$, MS(EI): 275 (M$^+$)

3.20. (RS)- or (SR)-3-Bromo-1-[(RS)-2-oxo-tetrahydro-furan-3-yl]-pyrrolidin-2-one IR(KBr): 1775, 1707 cm$^{-1}$, MS(EI): 168 (M–Br)$^+$ 3.21. (RS)-3-Bromo-1-(1-trityl-1H-tetrazol-5-ylmethyl)-pyrrolidin-2-one IR(KBr): 1704, 1632, 1492 cm$^{-1}$ 3.22. (RS)-4-(3-Bromo-2-oxo-pyrrolidin-1-yl)-piperidine-1-carboxylic acid allyl ester IR(neat): 1697, 1648 cm$^{-1}$, MS(ISP): 331.1 (M$^+$H)$^+$ 3.23. (RS)-4-(3-Bromo-2-oxo-pyrrolidin-1-yl)-piperidine-1-carboxylic acid ethyl ester IR(KBr): 1698, 1670 cm$^{-1}$, MS(ISP): 319.3 (M$^+$H)$^+$ 4. Direct conversion of the acid chlorides into the bromolactams (Scheme 2, 1→3)

4.1. Using Dowex catalyst 4.1.1. Preparation of (RS)-3-bromo-1-(3-fluoro-phenyl)-pyrrolidin-2-one.

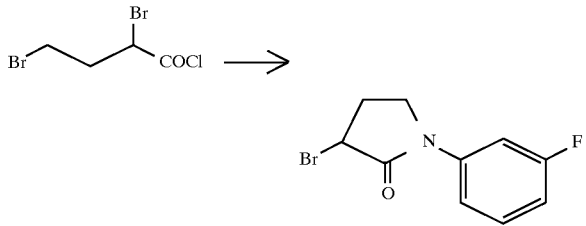

To a solution of 7 ml (72.8 mmol) m-fluoroaniline in 175 ml dichloromethane was added 35 ml water and the biphasic mixture was cooled to 0° C. and stirred vigorously. A solution of 17.5 g (66.2 mmol) 2,4-dibromobutanoic acid chloride[1]) in 35 ml dichloromethane was added dropwise during 10 min, followed by 3.18 g (79.4 mmol) NaOH dissolved in 6 ml water. After 2.5 h at 0°–10° C. another 170 ml 50% sodium hydroxide solution and 3 g Dowex 2×10 were added. After 2.5 h at rt the mixture was poured on 300 ml ice-water, the phases were separated and the aqueous phase extracted twice with 250 ml dichloromethane. The combined organic phases were washed with each 300 ml water and brine and dried over magnesium sulfate. Evaporation of the solvent gave a beige powder which was digerated in diethylether to yield 10.9 g (63%) colorless material.

[1]) H. Ikuta et al., J. Med. Chem., 30, 1995 (1987)

IR(KBr): 1703 cm$^{-1}$; MS(EI): 257 (M$^+$)

4.1.2. (RS)-3-Bromo-1-(2-chloro-pyridin-3-yl)-pyrrolidin-2-one

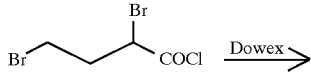

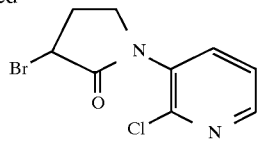

A vigorously stirred solution of 7.1 ml (55 mmol) 3-amino-2-chloropyridine in 25 ml 2N NaOH and 1.25 ml THF was cooled to 10° C. and 2,4-dibromobutanoic acid chloride[1]) (13.2 g, 50 mmol) were added dropwise during 40 min, followed by 50 ml dichloromethane. After 2 h at room temperature 70 ml dichloromethane, 38 ml 50% sodium hydroxide solution and 1.6 g Dowex 2×10 were added. After additional 18 h the mixture was poured on 120 ml ice-water, the phases were separated and the aqueous phase extracted twice with 100 ml dichloromethane. The combined organic phases were washed with each 200 ml water and brine and dried over magnesium sulfate. Evaporation of the solvent gave a beige solid which was purified by silica gel flash-chromatography (ethyl acetate).

[1]) H. Ikuta et al., J. Med. Chem., 30, 1995 (1987)

yield 7.61 g (56%) yellowish oil

IR(neat): 1712, 1563 cm$^{-1}$, MS(EI): 274 (M$^+$)

According to the procedure set forth in the preceding examples, the following additional compounds were prepared:

4.1.3. (RS)-3-Bromo-1-naphthalen-1-yl-pyrrolidin-2-one

IR (KBr): 1702 cm$^{-1}$, MS (EI): 289 (M)$^+$ 4.1.4. (RS)-3-Bromo-1-(3-trifluoromethyl-phenyl)-pyrrolidin-2-one IR (KBr): 1700 cm$^{-1}$, MS (EI): 307 (M)$^+$ 4.1.5. (RS)-3-Bromo-1-(3-methoxy-phenyl)-pyrrolidin-2-one IR (KBr): 1689 cm$^{-1}$, MS (EI): 269 (M)$^+$ 4.1.6. (RS)-3-Bromo-1-(2,2-diphenyl-1,3-benzodioxal-5-yl)-pyrrolidin-2-one IR (KBr): 1688 cm$^{-1}$, MS (EI): 435 (M$^+$)

4.1.7. Carbonic acid (RS)-3-(3-bromo-2-oxo-pyrrolidin-1-yl)-phenyl ester tert-butyl ester IR (KBr): 1754, 1701 cm$^{-1}$, MS (EI): 298 (M–t-Bu)

4.1.8. Carbonic acid (RS)-4-[3-bromo-2-oxo-pyrrolidin-1-yl]-2-fluoro-phenyl ester tert-butyl ester IR (KBr): 1765, 1703 cm$^{-1}$, MS (EI): 358 (M–CH$_3$)

4.1.9. (RS)-3-Bromo-1-(2-methoxy-phenyl)-pyrrolidin-2-one

IR (KBr): 1707 cm$^{-1}$, MS (EI): 269 (M$^+$)

4.1.10. (RS)—N-[4-(3-Bromo-2-oxo-pyrrolidin-1-ylmethyl)-phenyl]-succinamic acid tert-butyl ester IR (KBr): 1723, 1681, 1602, 1536 cm$^{-1}$, MS (ISP): 427.4 (M+H)$^+$ 4.1.11. Carbonic acid (RS)-3-(3-bromo-2-oxo-pyrrolidin-1-ylmethyl)-phenyl ester tert-butyl ester IR (KBr): 1757, 1703, 1610 cm$^{-1}$, MS (ISP): 387.2 (M+NH$_4$)$^+$ 4.1.12. (RS)-3-Bromo-1-(3-fluoro-benzyl)-pyrrolidin-2-one IR (Film): 1701, 1616, 1591 cm$^{-1}$, MS (EI): 192 (M–Br)

4.1.13. (RS)-3-Bromo-1-(4-methoxy-benzyl)-pyrrolidin-2-one

IR (KBr): 1682, 1610 cm$^{-1}$, MS (EI): 204 (M–HBr)

4.1.14. (RS)-3-Bromo-1-(4-fluoro-benzyl)-pyrrolidin-2-one

IR (Film): 1699, 1510 cm$^{-1}$, MS (EI): 192 (M–Br)

4.1.15. 5-Bromo-6-(2,2-dimethoxy-propyl)-1,3-benzodioxole $^1$H-NMR (CDCl$_3$, 250 MHz): 8.8 (sb,1H), 7.8 (m,2H), 7.6 (dd,1H), 4.8 (q,1H), 3.7 (m,2H), 2.5 (m,2H)

4.1.16. Carbonic acid 4-(3-bromo-2-oxo-pyrrolidin-1-yl)-3-fluoro-phenyl ester tert-butyl ester $^1$H-NMR (CDCl$_3$, 250 MHz): 7.4 (t,1H), 7.0 (m,2H), 4.6 (q,1H), 4.0 (m,1H), 3.8 (m,1H), 2.8 (m,1H), 2.5 (m,1H), 1.5 (s,9H)

4.1.17. (RS)-3-Bromo-1-(2-fluoro-phenyl)-pyrrolidin-2-one
IR (KBr): 1710, 1610 cm$^{-1}$, MS (EI): 259 (M)$^+$ 4.1.18. Carbonic acid (RS)-2-(3-bromo-2-oxo-pyrrolidin-1-yl)-phenyl ester tert-butyl ester
IR (KBr): 1752, 1699, 1604 cm$^{-1}$, MS (ISP): 356.3 (M+H)$^+$ 4.1.19. (RS)-2-(3-Bromo-2-oxo-pyrrolidin-1-yl)-thiophene-3-carboxylic acid ethyl ester
IR(KBr): 1710, 1534 cm$^{-1}$, MS(EI): 317 (M)$^+$ 4.1.20 (RS)-2-(3-Bromo-2-oxo-pyrrolidin-1-yl)-thiophene-3-carboxylic acid allyl ester
IR(KBr): 1717, 1534 cm$^{-1}$, MS(EI): 329 (M)$^+$ 4.2. Without catalyst using an organic base
4.2.1. (RS)-3-Bromo-1.(1,3,4-thiadiazol-2-yl)-pyrrolidin-2-one

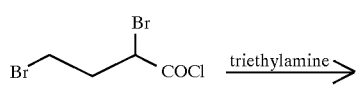

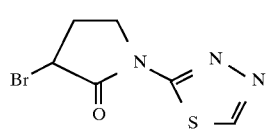

A solution of 36.7 g (363 mmol) 2-amino-1,3,4-thiadiazole and 3.5 g (29 mmol) 4-dimethylaminopyridine in 500 ml 1,3-dimethylimidazolidin-2-one and 145 ml triethylamine was cooled to 0° C. and 104.8 g (400 mmol) 2,4-dibromo-butanoic acid chloride$^1$) were added the temperature being kept below 5° C. After 2 h water was added, the mixture was extracted with ethyl acetate and the combined organic phases washed with water and brine, dried over sodium sulfate and evaporated. The residue was purified by silica gel chromatography (hexane:ethyl acetate=1:1) yielding 19.45 g (21.5%) yellow product.
$^{1)}$ H. Ikuta et al., J. Med. Chem., 30, 1995 (1987)
IR(KBr): 1723, 1685 cm$^{-1}$, MS(EI): 249 (M$^+$)

4.3. Without catalyst using an inorganic base
4.3.1. (RS)-3-Bromo-1-pyrimidin-2-yl-pyrrolidin-2-one

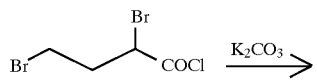

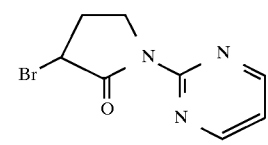

A solution of 4.3 g (45.5 mmol) 2-aminopyrimidine and 3.67 ml (45.5 mmol) pyridine in 22 ml dichloromethane was cooled to 0° C. A solution of 13.22 g (50 mmol) 2,4-dibromobutanoic acid chlorides) in 22 ml dichloromethane was added dropwise within 1 h and the mixture was warmed to room temperature within 30 min. After evaporation of the solvent, 300 ml water and 6.3 g (45.5 mmol) potassium carbonate were added and the solution was refluxed for 1.5 h. It was subsequently extracted with dichloromethane, the combined organic phases were washed with water and brine and dried over magnesium sulfate. The solvent was evaporated and the residue purified by silica gel chromatography (ethyl acetate:methanol=9:1) yielding 2.3 g (21%) beige crystals.

$^{1)}$ H. Ikuta et al., J. Med. Chem., 30, 1995 (1987)
mp: 94°–97° C., IR (KBr): 1723, 1685 cm$^{-1}$, MS (EI): 241 (M$^+$)

5. Preparation of the triphenylphosphonium salts, Wittig reagent (Scheme 2, 3→4)

5.1. Preparation of (RS)-[1-(4-tert-butoxycarbonyloxy-phenyl)-2-oxo-pyrrolidin-3-yl]-triphenyl-phosphonium bromide

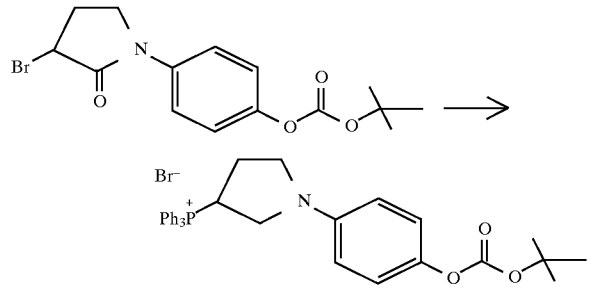

A solution of 14.6 g (41 mmol) carbonic acid (RS)-4-(3-bromo-2-oxo-pyrrolidin-1-yl)-phenyl ester tert-butyl ester and 14 g (53.4 mmol) triphenylphosphine was refluxed in 250 ml benzene for 48 h. The solid material was collected by filtration, washed with benzene and n-hexane and dried i.vac (14.72 g). The mother liquor was refluxed for another 72 h, yielding additional 4.4 g of the product. Total yield: 19.12 g (75.5%) colorless crystals.
mp. 147°–150° C.; IR(KBr): 1756, 1690 cm$^{-1}$; MS (ISP): 538.5 (M)$^+$ 5.2. (RS)-[1-(1H-Benzimidazol-2-ylmethyl)-2-oxo-pyrrolidin-3-yl]-triphenylphosphonium bromide

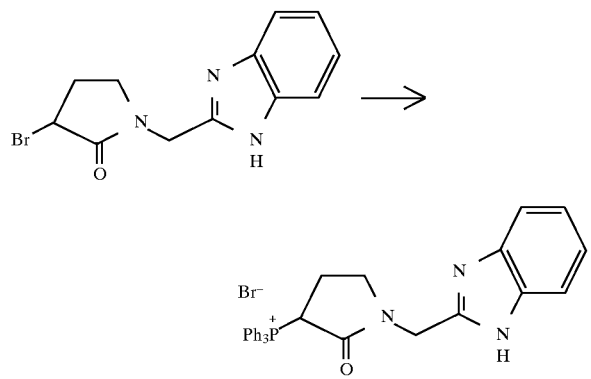

A solution of 7.11 g (24.1 mmol) (RS)-3-bromo-1-(1H-benzimidazol-2-ylmethyl)-pyrrolidin-2-one and 6.7 g (25.5 mmol) triphenylphosphine was refluxed in 110 ml THF for 7 d. The solid material was collected by filtration, washed with THF and dried.
yield: 11.63 g (87%) colorless powder
IR(KBr): 1695, 1485, 1437 cm$^{-1}$, MS(ISP): 476.3 (M$^+$)

According to the procedure set forth in the preceding examples, the following additional compounds were prepared:

5.3. (RS)-[1-(3-Nitro-phenyl)-2-oxo-pyrrolidin-3-yl]-triphenyl-phosphonium bromide
m.p. 135°–137° C.; IR (KBr): 1695 cm$^{-1}$, MS (ISP): 467.4 (M)$^+$ 5.4. (RS)-(1-Naphthalen-1-yl-2-oxo-pyrrolidin-3-yl)-triphenyl-phosphonium bromide
IR (KBr): 1691 cm$^{-1}$, MS (ISP): 472.6 (M)$^+$ 5.5. (RS)-[1-(4-tert-Butoxycarbonyl-phenyl)-2-oxo-pyrrolidin-3-yl]-triphenyl-phosphonium bromide IR (KBr): 1700 cm$^{-1}$, MS (ISP): 522.5 (M)$^+$ 5.6. (RS)-(1-Naphthalen-2-yl-2-oxo-pyrrolidin-3-yl)-triphenyl-phosphonium bromide IR (KBr): 1691 cm$^{-1}$, MS (ISP): 472.4 (M)$^+$ 5.7. (RS)-[1-(3-Methoxy-phenyl)-2-oxo-pyrrolidin-3-yl] triphenyl-phosphonium bromide IR (KBr): 1685 cm$^{-1}$, MS (ISP): 452.5 (M)$^+$ 5.8. (RS)-[1-(3-Trifluoromethyl-phenyl)-2-oxo-pyrrolidin-3-yl]-triphenyl-phosphonium bromide IR (KBr): 1697 cm$^{-1}$, MS (ISP): 490.4 (M)$^+$ 5.9. (RS)-[1-(3-Fluoro-phenyl)-2-oxo-pyrrolidin-3-yl]-triphenyl-phosphonium bromide IR (KBr): 1695 cm$^{-1}$, MS (ISP): 440.4 (M)$^+$ 5.10. (RS)-[1-(2,2-Diphenyl-1,3-benzodioxol-5-yl)-2-oxo-pyrrolidin-3-yl]-triphenyl-phosphonium bromide IR (KBr): 1688 cm$^{-1}$, MS (ISP): 618.3 (M)$^+$ 5.11. (RS)-[1-(3-tert-Butoxycarbonyloxy-phenyl)-2-oxo-pyrrolidin-3-yl]-triphenyl-phosphonium bromide IR (KBr): 1694 cm$^{-1}$, MS (ISP): 538.4 (M)$^+$ 5.12. (RS)-[1-(4-tert-Butoxycarbonyloxy-3-fluoro-phenyl)-2-oxo-pyrrolidin-3-yl]-triphenyl-phosphonium bromide IR (KBr): 1764, 1693 cm$^{-1}$, MS (ISP): 556.3 (M)$^+$ 5.13. (RS)-[2-Oxo-1-(4-tritylcarbamoyl-phenyl)-pyrrolidin-3-yl]-triphenyl-phosphonium bromide IR (KBr): 1692 cm$^{-1}$, MS (ISP): 707.4 (M)$^+$ 5.14. (RS)-[1-(2-Methoxy-phenyl)-2-oxo-pyrrolidin-3-yl]-triphenyl-phosphonium bromide IR (KBr): 1684 cm$^{-1}$, MS (ISP): 452.4 (M)$^+$ 5.15. (RS)-[1-(3-Fluoro-2-hydroxy-phenyl)-2-oxo-pyrrolidin-3-yl]-triphenyl-phosphonium bromide $^1$H-NMR (DMSO, 250 MHz): 10.2 (sb,1H), 7.9 (m,15H), 7.2 (dd,1H), 6.8 (m,1H), 6.5 (d,1H), 5.7 (m,1H), 3.9 (m,1H), 3.5 (m,1H), 2.8 (m,1H), 2.5 (m,1H)

5.16. (RS)-[1-(4-tert-Butoxycarbonyloxy-2-fluoro-phenyl)-2-oxo-pyrrolidin-3-yl]-triphenyl-phosphonium bromide $^1$H-NMR (DMSO, 250 MHz): 7.7–8.0 (m,15H), 7.1–7.4 (m,3H), 5.9 (m,1H), 4.0 (m,1H), 3.6 (m,1H), 2.8 (m,1H), 2.5 (m,1H), 1.5 (s,9H)

5.17. (RS)-[1-(2-Fluoro-phenyl)-2-oxo-pyrrolidin-3-yl]-triphenyl-phosphonium bromide IR (KBr): 1707, 1502 cm$^{-1}$, MS (ISP): 440.4 (M)$^+$ 5.18. (RS)-[1-(2-tert-Butoxycarbonyloxy-phenyl)-2-oxo-pyrrolidin-3-yl]-triphenyl-phosphonium bromide $^1$H-NMR (DMSO, 250 MHz): 7.7–8.0 (m,15H), 7.3 (m,1H), 7.1 (m,1H), 6.9 (dd,1H), 6.7 (m,1H), 5.8 (m,1H), 3.9 (m,1H), 3.5 (m,1H), 2.8 (m,1H), 2.5 (m,1H), 1.4 (s,9H)

5.19. Mixture of (RS)- and (SR)-[1-[(RS)-tert-butoxycarbonyl-phenyl-methyl]-2-oxo-pyrrolidin-3-yl]-triphenyl-phosphonium bromide IR (KBr): 1733, 1688, 1438 cm$^{-1}$, MS (ISP): 536.5 (M)$^+$ 5.20. (RS)-[1-(2-Fluoro-benzyl)-2-oxo-pyrrolidin-3-yl]-triphenyl-phosphonium bromide IR (KBr): 1684, 1586, 1438 cm$^{-1}$, MS (ISP): 454.4 (M)$^+$ 5.21. (RS)-[1-(2-Methoxy-benzyl)-2-oxo-pyrrolidin-3-yl]-triphenyl-phosphonium bromide IR (KBr): 1685, 1436 cm$^{-1}$, MS (ISP): 466.4 (M)$^+$ 5.22. (RS)-[1-(3-tert-Butoxycarbonyloxy-benzyl)-2-oxo-pyrrolidin-3-yl]-triphenyl-phosphonium bromide IR (KBr): 1756, 1687, 1438 cm$^{-1}$, MS (ISP): 552.1 (M)$^+$ 5.23. (RS)-[1-(3-Fluoro-benzyl)-2-oxo-pyrrolidin-3-y]-triphenyl-phosphonium bromide IR (KBr): 2748, 1691, 1588 cm$^{-1}$, MS (ISP): 454.3 (M)$^+$ 5.24. (RS)-[1-(3-Methoxy-benzyl)-2-oxo-pyrrolidin-3-yl]-triphenyl-phosphonium bromide IR (KBr): 1683, 1436 cm$^{-1}$, MS (ISP): 466.4 (M)$^+$ 5.25. (RS)-[1-[4-(3-tert-Butoxycarbonyl-propionylamino)-benzyl]-2-oxo-pyrrolidin-3-yl]-triphenyl-phosphonium bromide IR (KBr): 1724, 1688, 1602 cm$^{-1}$, MS (ISP): 607 (M)$^+$ 5.26. (RS)-[1-(4-Allyloxycarbonylamino-benzyl)-2-oxo-pyrrolidin-3-yl]-triphenyl-phosphonium bromide IR (KBr): 3427, 1720, 1687 cm$^{-1}$, MS (ISP): 535 (M)$^+$ 5.27. (RS)-[1-(4-tert-Butoxycarbonyl-benzyl)-2-oxo-pyrrolidin-3-yl]-triphenylphosphonium bromide IR (KBr): 1690, 1611, 1438 cm$^{-1}$, MS (ISP): 536.4 (M)$^+$ 5.28. (RS)-[2-Oxo-1-(4-nitro-benzyl)-pyrrolidin-3-yl]-triphenyl-phosphonium bromide IR (KBr): 1688, 1603, 1518 cm$^{-1}$, MS (ISP): 481.3 (M)$^+$ 5.29. (RS)-[1-(4-Methoxy-benzyl)-2-oxo-pyrrolidin-3-yl]-triphenyl-phosphonium bromide IR (KBr): 1684, 1615, 1512 cm$^{-1}$, MS (ISP): 466.3 (M)$^+$ 5.30. (RS)-[1-(4-Fluoro-benzyl)-2-oxo-pyrrolidin-3-yl]-triphenyl-phosphonium bromide IR (KBr): 1685, 1602, 1509 cm$^{-1}$, MS (ISP): 454.4 (M)$^+$ 5.31. (RS)-[2-Oxo-1-(4-trifluoromethyl-benzyl)-pyrrolidin-3-yl]-triphenyl-phosphonium bromide IR (KBr): 1686, 1617, 1438 cm$^{-1}$, MS (ISP): 504.4 (M)$^+$ 5.32. (RS)-(1-Benzyl-2-oxo-pyrrolidin-3-yl)-triphenyl-phosphonium bromide IR (KBr): 2796, 1682, 1438 cm$^{-1}$, MS (ISP): 436.8 (M)$^+$ 5.33. (RS)-Triphenyl-(1-thiophen-2-ylmethyl-2-oxo-pyrrolidin-3-yl)-phosphonium bromide IR(KBr): 2784, 1685, 1480 cm$^{-1}$, MS(ISP): 442.5 (M$^+$)

5.34. (RS)-[2-Oxo-1-(1-trityl-1H-tetrazol-5-ylmethyl)-pyrrolidin-3-yl]-triphenyl-phosphonium bromide IR(KBr): 3432, 1695, 1439 cm$^{-1}$, MS(ISP): 670.2 (M$^+$)

5.35. Mixture of [(RS)- and [(SR)-2-oxo-1-[(RS)-tetrahydro-furan-2-ylmethyl]-pyrrolidin-3-yl]-triphenyl-phosphonium bromide IR(neat): 1684, 1590, 1437 cm$^{-1}$, MS(ISP): 430.5 (M$^+$)

5.36. (RS)-[1-(3,5-Dimethyl-pyrazin-2-yl)-2-oxo-pyrrolidin-3-yl]-triphenyl-phosphonium bromide IR(KBr): 1699, 1438 cm$^{-1}$, MS(ISP): 452.4 (M$^+$)

5.37. (RS)-(2-Oxo-1-pyrimidin-2-yl-pyrrolidin-3-yl)-triphenyl-phosphonium bromide IR(KBr): 1717, 1658, 1566 cm$^{-1}$, MS(LDP): 424.2 (M+H)$^+$ 5.38. (RS)-[1-(6-Chloro-pyridazin-3-yl )-2-oxo-pyrrolidin-3-yl]-triphenyl-phosphonium bromide IR(KBr): 1708 cm$^{-1}$, MS(ISP): 458.3 (M$^+$)

5.39. (RS)-[1-(2-Chloro-pyridin-3-yl)-2-oxo-pyrrolidin-3-yl]-triphenyl-phosphonium bromide IR(KBr): 1695 cm$^{-1}$, MS(ISP): 457.4 (M$^+$)

5.40. [1-(1-Ethoxycarbonyl-piperidin-4-yl)-2-oxo-pyrrolidin-3-yl]-triphenyl-phosphonium bromide IR(KBr): 1683, 1436 cm$^{-1}$, MS(ISP): 501.5 (M$^+$)

5.41. (RS)-[1-(1-Allyloxycarbonyl-piperidin-4-yl)-2-oxo-pyrrolidine-3-yl]-triphenyl-phosphonium bromide IR(KBr): 1684, 1437 cm$^{-1}$, MS(ISP): 513 (M$^+$)

5.42. Mixture of [(RS)- and [(SR)-2-oxo-1-[(RS)-2-oxo-tetrahydro-furan-3-yl]-pyrrolidin-3-yl]-triphenyl-phosphonium bromide IR(KBr): 1776, 1689 cm$^{-1}$, MS(ISP): 430.4 (M$^+$)

5.43. (RS)-[2-Oxo-1-(1,3,4-thiadiazol-2-yl)-pyrrolidin-3-yl]-triphenyl-phosphonium bromide IR(KBr): 1698, 1685, 1471 cm$^{-1}$, MS(ISP): 430.3 (M$^+$)

5.44. (RS)-[1-(3-Ethyloxycarbonyl-thiophene-2-yl)-2-oxo-pyrrolidin-3-yl]-triphenyl-phosphonium bromide IR(KBr): 1703, 1435 cm$^{-1}$, MS(ISP): 500 (M$^+$)

5.45. (RS)-[1-(3-Allylcarbonyl-thiophene-2-yl)-2-oxo-pyrrolidin-3-yl]-triphenyl-phosphonium bromide IR(KBr): 1705, 1437 cm$^{-1}$, MS(ISP): 512 (M$^+$)

6. Reaction of a 2-cephem aldehyde (1) or 3-cephem aldehyde (2) with a Wittig reagent (3) Scheme 1.

6.1. Preparation of (E)-(2R,6R,7R)-7-tert-Butoxycarbonylamino-3-[1-(4-tert-butoxycarbonyloxyphenyl)-2-oxo-pyrrolidin-3-ylidenemethyl]-8-oxo-5-thia-1-aza-bicyclo[4.2.0]oct-3-ene-2-carboxylic acid benzhydryl ester ml 1,2-butyleneoxide and 85 ml DMSO was refluxed for 2.5 h. The solution was concentrated and the residue purified by

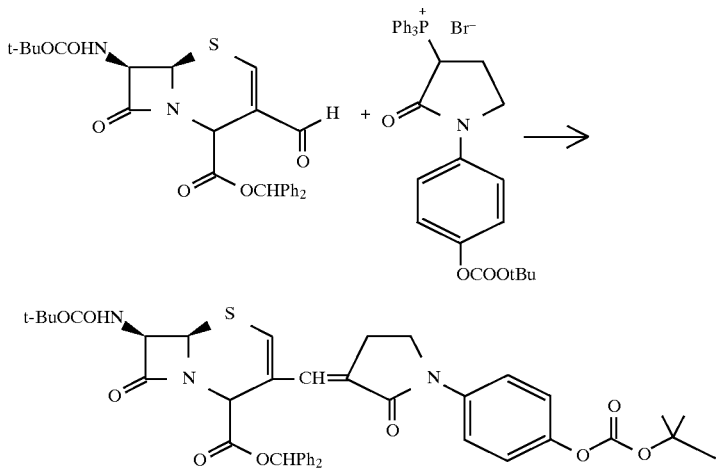

A mixture of 12.11 g (24.49 mmol) (2R,6R,7R)-7-tert-butoxycarbonylamino-3-formyl-8-oxo-5-thia-1-azabicyclo[4.2.0]oct-3-ene-2-carboxylic acid benzhydryl ester and 17.17 g (27.77 mmol) (RS)-[1-(4-tert-butoxycarbonyloxy-phenyl)-2-oxo-pyrrolidin-3-yl]-triphenyl-phosphonium bromide in 250 ml 1,2-dichloroethane/1,2 butyleneoxide (1:1) was refluxed for 3.5 h. The solution was evaporated and the residue purified by chromatography over silicagel (25 g, Merck, 40–63 mm, 230 bis 400 mesh, dichloromethane:ethylacetate=9:1) yielding 9.81 g (53%) colorless crystals.

IR(KBr): 1781, 1750, 1691 cm$^{-1}$; MS(ISP): 754.5 (M+H)$^+$ 6.2. (E)-(2R,6R,7R)-3-[1-(1H-Benzimidazol-2-ylmethyl)-2-oxo-pyrrolidin-3-ylidenemethyl]-7-tert-butoxycarbonylamino-8-oxo-5-thia-1-aza-bicylco[4.2.0]oct-3-ene-2-carboxylic acid benzhydryl ester chromatography over silica gel (dichloromethane ethyl acetate=9:1) yielding 9.81 g (53%) colorless crystals.

IR(KBr): 1782, 1719, 1684 cm$^{-1}$, MS(ISP): 692.5 (M+H$^+$)

According to the procedure set forth in the preceding examples, the following additional compounds were prepared:

6.3. (E)-(2R,6R,7R)-7-tert-Butoxycarbonylamino-3-[1-(3-nitro-phenyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1782, 1726, 1696 cm$^{-1}$, MS (ISP): 683.4 (M+H)$^+$ 6.4. (E)-(2R,6R,7R)-7-tert-Butoxycarbonylamino-(1-naphthalen-1-yl-2-oxo-pyrrolidin-3-ylidenemethyl)-8-oxo-5-thia-1-aza-bicyclo[4.2.0]oct-3-ene-2-carboxylic acid benzhydryl ester

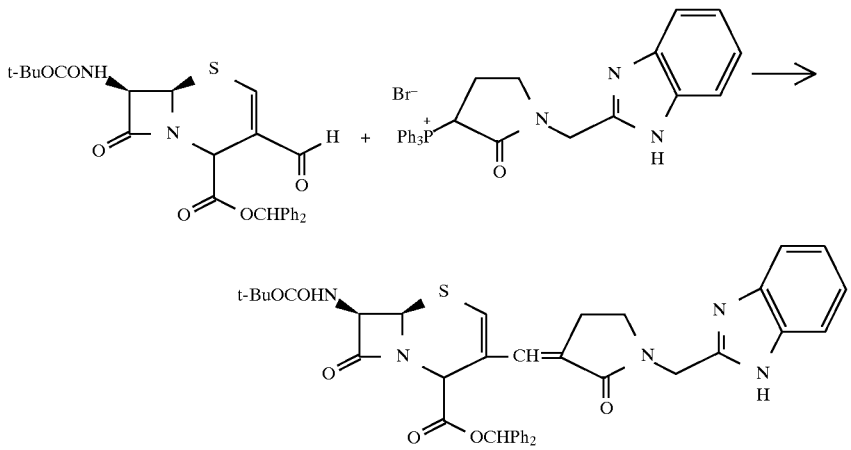

A mixture of 5.25 g (10.6 mmol) (2R,6R,7R)-7-tert-butoxycarbonylamino-3-formyl-8-oxo-5-thia-1-azabicyclo[4.2.0]oct-3-ene-2-carboxylic acid benzhydryl ester and 6.5 g (11.7 mmol) (RS)-[1-(1H-benzimidazol-2-ylmethyl)-2-oxo-pyrrolidin-3-yl]-triphenylphosphonium bromide in 175

IR (KBr): 1782, 1719 cm$^{-1}$, MS (ISP): 688.5 (M+H)$^+$ 6.5. (E)-(2R,6R,7R)-7-tert-Butoxycarbonylamino-3-[1-(4-tert-butoxycarbonyl-phenyl)-2-oxo-pyrrolidin-3-ylidenemethyl]-8-oxo-5-thia-1-aza-bicyclo[4.2.0]oct-3-ene-2-carboxylic acid benzylhydryl ester IR (KBr): 1783, 1708 cm$^{-1}$, MS (ISP): 738.5 (M+H)$^+$ 6.6. (E)-(2R,6R,7R)-7-tert-Butoxycarbonylamino-3-[1-(3-tert-butoxycarbonyloxy-phenyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1782, 1754, 1692 cm$^{-1}$, MS (ISP): 754.3 (M+H)$^+$ 6.7. (E)-(2R,6R,7R)-7-tert-Butoxycarbonylamino-3-[1-(2-diphenyl-1,3-benzodioxol-5-yl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1783, 1718, 1686 cm$^{-1}$, MS (ISP): 834.2 (M+H)$^+$ 6.8. (E)-(2R,6R,7R)-7-tert-Butoxycarbonylamino-3-[1-(4-tert-butoxycarbonyloxy-3-fluoro-phenyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1783, 1695 cm$^{-1}$, MS (ISP): 772.2 (M+H)$^+$ 6.9. (E)-(2R,6R,7R)-7-tert-Butoxycarbonylamino-8-oxo-3-[2-oxo-1-(4-tritylcarbamoyl-phenyl)-pyrrolidin-3-ylidenemethyl]-5-thia-1-aza-bicyclo[4.2.0]oct-3-ene-2-carboxylic acid benzhydryl ester IR (KBr): 1783, 1726, 1683 cm$^{-1}$, MS (ISP): 923.4 (M+H)$^+$ 6.10. (E)-(2R,6R,7R)-7-tert-Butoxycarbonylamino-3-[1-(2-methoxy-phenyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1782, 1741, 1716, 1691 cm$^{-1}$, MS (ISP): 668.3 (M+H)$^+$ 6.11. (E)-(2R,6R,7R)-7-tert-Butoxycarbonylamino-3-[1-(3-fluoro-2-hydroxy-phenyl)-2-oxo-pyrrolidin-3-ylidenemethyl]-8-oxo-5-thia-1-aza-bicyclo[4.2.0]oct-3-ene-2-carboxylic acid benzhydryl ester $^1$H-NMR (CDCl$_3$, 250 MHz): 9.1 (s,1H), 7.3 (m,10H), 6.8–7.1 (m,5H), 6.7 (s,1H), 5.2–5.5 (m,4H), 3.6–3.9 (m,2H), 2.8–3.1 (m,2H), 1.5 (s.9H)

6.12. (E)-(2R,6R,7R)-7-tert-Butoxycarbonylamino-3-[1-(4-tert-butoxycarbonyloxy-2-fluoro-phenyl)-2-oxo-pyrrolidin-3-ylidenemethyl]-8-oxo-5-thia-1-aza-bicyclo[4.2.0]oct-3-ene-2-carboxylic acid benzhydryl ester $^1$H-NMR (CDCl$_3$, 250 MHz): 7.5 (t,1H), 7.3 (m,10H), 7.1 (m,5H), 6.9 (s,1H), 6.6 (s,1H), 5.2–5.5 (m,4H), 3.7 (m,2H), 2.9 (m,2H), 1.6 (s,9H), 1.5 (s,9H)

6.13. (E)-(2R,6R,7R)-7-tert-Butoxycarbonylamino-3-[1-(2-fluoro-phenyl)-2-oxo-pyrrolidin-3-ylidenemethyl]-8-oxo-5-thia-1-aza-bicyclo[4.2.0]oct-3-ene-2-carboxylic acid benzylhydryl ester IR (KBr): 1781, 1701 cm$^{-1}$, MS (ISP): 656.2 (M+H)$^+$ 6.14. (E)-(2R,6R,7R)-7-tert-Butoxycarbonylamino-3-[1-(2-tert-butoxycarbonyloxy-phenyl)-2-oxo-pyrrolidin-3-ylidenemethyl]-8-oxo-5-thia-1-aza-bicyclo[4.2.0]oct-3-ene-2-carboxylic acid benzhydryl ester $^1$H-NMR (CDCl$_3$, 250 MHz): 6.9–7.4 (m,15H), 6.9 (s,1H), 6.6 (s,1H), 5.2–5.5 (m,4H), 3.5–3.8 (m,2H), 3.7–3.0 (m,2H), 1.5 (s,9H)

6.15. Mixture of (E)-(2R,6R,7R)-7-tert-butoxycarbonylamino-3-[1-[(R)- and -[(S)-tert-butoxycarbonyl-8-oxo-5-thia-1-aza-bicyclo[4.2.0]oct-3-ene-2-carboxylic acid benzhydryl ester IR (KBr): 1784, 1737, 1687, 1641 cm$^{-1}$, MS (ISP): 751.9 (M+H)$^+$ 6.16. (E)-(2R,6R,7R)-7-tert-Butoxycarbonylamino-3-[1-(2-fluoro-benzyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1782, 1743, 1716, 1682 cm$^{-1}$, MS (ISP): 670.3 (M+H)$^+$ 6.17. (E)-(2R,6R,7R)-7-tert-Butoxycarbonylamino-3-[1-(2-methoxy-benzyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1782, 1742, 1715, 1682 cm$^{-1}$, MS (ISP): 682.3 (M+H)$^+$ 6.18. (E)-(2R,6R,7R)-7-tert-Butoxycarbonylamino-3-[1-(3-tert-butoxycarbonyloxy-benzyl)-2-oxo-pyrrolidin-3-ylidenemethyl]-8-oxo-5-thia-1-azabicyclo[4.2.0]oct-3-ene-2-carboxylic acid benzhydryl ester IR (KBr): 1783, 1756, 1718, 1684 cm$^{-1}$, MS (ISP): 768.1 (M+H)$^+$ 6.19. (E)-(2R,6R,7R)-7-tert-Butoxycarbonylamino-3-[1-(3-fluoro-benzyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1780, 1744, 1715, 1680 cm$^{-1}$, MS (ISP): 669.9 (M+H)$^+$ 6.20. (E)-(2R,6R,7R)-7-tert-Butoxycarbonylamino-3-[1-(3-methoxy-benzyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1781, 1743, 1716, 1680 cm$^{-1}$, MS (ISP): 682.2 (M+H)$^+$ 6.21. (E)-(2R,6R,7R)-7-tert-Butoxycarbonylamino-3-[1-[4-(3-tert-butoxycarbonyl-propionylamino)-benzyl]- 2-oxo-pyrrolidin-3-ylidenemethyl]-8-oxo-5-thia-1-aza-bicyclo[4.2.0]oct-3-ene-2-carboxylic acid benzhydryl ester IR (KBr): 1783, 1723, 1686 cm$^{-1}$, MS (ISP): 840.5 (M+NH$_4$)$^+$ 6.22. (E)-(2R,6R,7R)-3-[1-(4-Allyloxycarbonylamino-benzyl)-2-oxo-pyrrolidin-3-ylidenemethyl]-7-tert-butoxycarbonylamino-8-oxo-5-thia-1-aza-bicyclo[4.2.0]oct-3-ene-2-carboxylic acid benzhydryl ester IR (KBr): 1781, 1727, 1679 cm$^{-1}$, MS (ISP): 751.7 (M+H)$^+$ 6.23. (E)-(2R,6R,7R)-7-tert-Butoxycarbonylamino-3-[1-(4-tert-butoxycarbonyl-benzyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1783, 1712, 1638 cm$^{-1}$, MS (ISP): 752.4 (M+H)$^+$ 6.24. (E)-(2R,6R,7R)-7-tert-Butoxycarbonylamino-3-[1-(4-nitro-benzyl-2-oxo-pyrrolidin-3-ylidenemethyl]-8-oxo-5-thia-1-aza-bicyclo[4.2.0]oct-3-ene-2-carboxylic acid benzhydryl ester IR (KBr): 1781, 1742, 1716, 1682 cm$^{-1}$, MS (ISP): 697.3 (M+H)$^+$ 6.25. (E)-(2R,6R,7R)-7-tert-Butoxycarbonylamino-3-[1-(4-methoxy-benzyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1782, 1742, 1715, 1680 cm$^{-1}$, MS (ISP): 682.3 (M)$^+$ 6.26. (E)-(2R,6R,7R)-7-tert-Butoxycarbonylamino-3-[1-(4-fluoro-benzyl)-2-oxo-pyrrolidin-3-ylidenemethyl]-8-oxo-5-thia-1-aza-bicyclo[4.2.0]oct-3-ene-2-carboxylic acid benzhydryl ester IR (KBr): 1782, 1743, 1717, 1681 cm$^{-1}$, MS (ISP): 670.3 (M+H)$^+$ 6.27. (E)-(2R,6R,7R)-7-tert-Butoxycarbonylamino-8-oxo-3-[2-oxo-1-(4-trifluoromethylbenzyl)-pyrrolidin-3-ylidenemethyl]-5-thia-1-aza-bicyclo[4.2.0]oct-3-ene-2-carboxylic acid benzhydryl ester IR (KBr): 1781, 1718, 1684 cm$^{-1}$, MS (ISP): 720.3 (M+H)$^+$ 6.28. (E)-(2R,6R,7R)-3-(1-Benzyl-2-oxo-pyrrolidin-3-ylidenemethyl)-7-tert-butoxycarbonylamino-8-oxo-5-thia-1-aza-bicyclo[4.2.0]oct-3-ene-2-carboxylic acid benzhydryl ester IR (KBr): 1782, 1743, 1717, 1682 cm$^{-1}$, MS (ISP): 652.3 (M+H)$^+$ 6.29. (E)-(2R,6R,7R)-7-tert-Butoxycarbonylamino-8-oxo-3-(2-oxo-1-thiophen-2-ylmethyl-pyrrolidin-3-ylidenemethyl)-5-thia-1-aza-bicyclo[4.2.0]oct-3-ene-2-carboxylic acid benzhydryl ester IR(KBr): 1781, 1741, 1716, 1682 cm$^{-1}$, MS(ISP): 658.4 (M+H)$^+$ 6.30. (E)-(2R,6R,7R)-7-tert-Butoxycarbonylamino-8-oxo-3-[2-oxo-1-(1-trityl-1H-tetrazol-5-ylmethyl)-pyrrolidin-3-ylidenemethyl]-5-thia-1-aza-bicyclo[4.2.0]oct-3-ene-2-carboxylic acid benzhydryl ester IR(KBr): 1783, 1741, 1717, 1690 cm$^{-1}$, MS(ISP): 903.4 (M+NH$_4$)$^+$ 6.31. 1:1 Mixture of (E)-(2R,6R,7R)-7-tert-Butoxycarbonylamino-8-oxo-3-[2-oxo-1-[(R)- and -[(S)-tetrahydro-furan-2-ylmethyl]-pyrrolidin-3-ylidenemethyl]-5-thia-1-aza-bicyclo[4.2.0]oct-3-ene-2-carboxylic acid benzhydryl ester IR(KBr): 1781, 1743, 1716, 1680 cm$^{-1}$, MS(ISP): 646.2 (M+H)$^+$ 6.32. (E)-(2R,6R,7R)-7-tert-Butoxycarbonylamino-3-[1-(1-ethoxycarbonyl-piperidin-4-yl)-2-oxo-pyrrolidin-3-ylidenemethyl]-8-oxo-5-thia-1-aza-bicyclo[4.2.0]oct-3-ene-2-carboxylic acid benzhydryl ester IR(KBr): 1784, 1744, 1689 cm$^{-1}$, MS(ISP): 717.5 (M+H)$^+$ 6.33. (E)-(2R,6R,7R)-3-[1-(1-Allyloxycarbonyl-piperidin-4-yl)-2-oxo-pyrrolidin-3-ylidenemethyl]-7-tert-butoxycarbonylamino-8-oxo-5-thia-1-aza-bicyclo [4.2.0]oct-3-ene-2-carboxylic acid benzhydryl ester IR(KBr): 1783, 1701, 1645 cm$^{-1}$, MS(ISP): 729.4 (M+H)$^+$ 6.34. (E)-(2R,6R,7R)-7-tert-Butoxycarbonylamino-3-[1-(2-chloro-pyridin-3-yl)-2-oxo-pyrrolidin-3-ylidenemethyl]-8-oxo-5-thia-1-aza-bicyclo[4.2.0]oct-3-ene-2-carboxylic acid benzhydryl ester IR(KBr): 1782, 1743, 1700, 1635 cm$^{-1}$, MS(ISP): 673.4 (M+H)$^+$ 6.35. 1:1 Mixture of (E)-(2R,6R,7R)-7-tert-Butoxycarbonylamino-8-oxo-3-[2-oxo-1-[(R)- and -[(S)-2-oxo-tetrahydrofuran-3-yl]-pyrrolidin-3-ylidenemethyl]-5-thia-1-aza-bicyclo[4.2.0]oct-3-ene-2-carboxylic acid benzhydryl ester IR(KBr): 1781, 1741, 1716, 1686, 1639 cm$^{-1}$, MS(ISP): 646.3 (M+H)$^+$ 6.36. (E)-(2R,6R,7R)-7-tert-Butoxycarbonylamino-8-oxo-3-[1-(3-ethoxycarbonyl-thiophen-2yl)-2-oxo-pyrrolidin-3-ylidenemethyl]-5-thia-1-aza-bicyclo[4.2.0]oct-3-ene-2-carboxylic acid benzhydryl ester IR(KBr): 1773, 1703 cm$^{-1}$, MS(ISP): 716.4 (M+H)$^+$ 6.37. (E)-(2R,6R,7R)-7-tert-Butoxycarbonylamino-8-oxo-3-[1-(3-allyloxycarbonyl-thiophen-2yl)-2-oxo-pyrrolidin-3-ylidenemethyl]-5-thia-1-aza-bicyclo[4.2.0]oct-3-ene-2-carboxylic acid benzhydryl ester IR(KBr): 1782, 1713 cm$^{-1}$, MS(ISP): 750 (M+Na)$^+$ 6.38. (E)-(2R,6R,7R)-7-tert-Butoxycarbonylamino-8-oxo-3-[1-(3-carbamoyl-thiophen-2yl)-2-oxo-pyrrolidin-3-ylidenemethyl]-5-thia-1-aza-bicyclo[4.2.0]oct-3-ene-2-carboxylic acid benzhydryl ester IR(KBr): 1779, 1664 cm$^{-1}$, MS(ISP): 687.3 (M+H)$^+$ 6.39. (E6.30.)-(2R,6R,7R)-7-tert-Butoxycarbonylamino-8-oxo-3-[1-(3-carboxy-thiophen-2yl)-2-oxo-pyrrolidin-3-ylidenemethyl]-5-thia-1-aza-bicyclo[4.2.0]oct-3-ene-2-carboxylic acid benzhydryl ester IR(KBr): 1782, 1712 cm$^{-1}$, MS(ISP): 688.2 (M+H)$^+$ 7. Conversion of compound (4) to the sulfoxide (5) Scheme 1

7.1. Preparation of Mixture of (E)-(5R,6R,7R)- and -(5S,6R,7R)-7-tert-butoxycarbonylamino-3-[1-(4-tert-butoxycarbonyloxy-phenyl)-2-oxo-pyrrolidin-3-ylidenemethyl]-5,8-dioxo-5-thia-1-aza-bicyclo[4.2.0]oct-2-ene-2-carboxylic acid benzhydryl ester

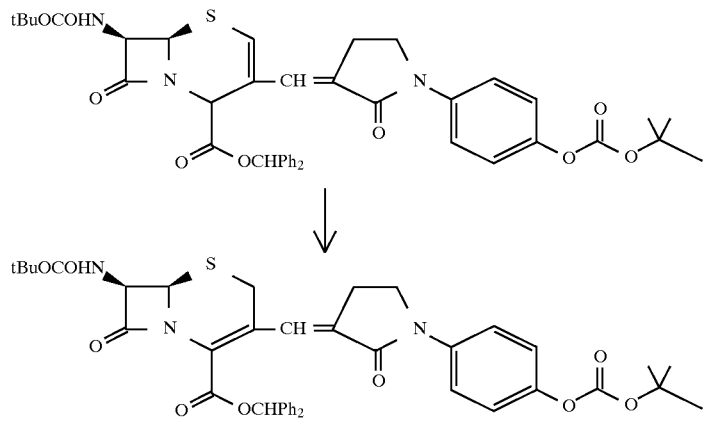

To a solution of 11.3 g (15 mmol) (E)-(2R,6R,7R)-7-tert-Butoxycarbonylamino-3-[1-(4-tert-butoxycarbonyloxy-phenyl)-2-oxo-pyrrolidin-3-ylidenemethyl]-8-oxo-5-thia-1-aza-bicyclo[4.2.0]oct-3-ene-2 carboxylic acid benzhydryl ester in 120 ml dichloromethane was added a solution of 3.27 g (15 mmol) 80–90% m-chloroperoxybenzoic acid in 60 ml dichloromethane at 4° C. After 1 hour, the reaction mixture was washed successively with cold solutions of 10% aqueous sodium thiosulfate, 5% aqueous sodium bicarbonate, and water. After drying over magnesium sulfate, the solvent was removed, and the residue was purified by flash silica gel column chromatography (3:2 ethylacetate/hexane), yielding 10.59 g (91.7%) of the product as a yellow foam.

IR(KBr): 1799, 1757, 1723 cm$^{-1}$; MS(ISP): 770.5 (M+H)$^+$ 7.2. 1:1 Mixture of (E)-(5R,6R,7R)- and -(5S,6R,7R)-3-[1-(1H-Benzimidazol-2-ylmethyl)-2-oxo-pyrrolidin-3-ylidenemethyl]-7-tert-butoxycarbonylamino-5,8-dioxo-5-thia-1-aza-bicylco[4.2.0]oct-2-ene-2-carboxylic acid benzhydryl ester

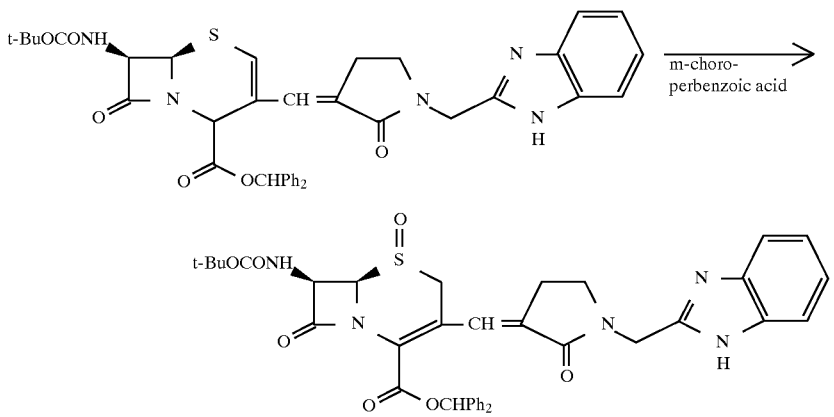

To a solution of 5.27 g (7.62 mmol) (E)-(2R,6R,7R)-3-[1-(1H-benzimidazol-2-ylmethyl)-2-oxo-pyrrolidin-3-ylidenemethyl]-7-tert-butoxycarbonylamino-8-oxo-5-thia-1-aza-bicylco[4.2.0]oct-3-ene-2-carboxylic acid benzhydryl ester in 45 ml dichloromethane was added a solution of 1.73 g (7.62 mmol) 70–75% m-chloroperoxybenzoic acid in 25 ml dichloromethane at 4° C. After 2 h, the reaction mixture was washed successively with cold solutions of 10% aqueous sodium thiosulfate, 5% aqueous sodium bicarbonate, and water. After drying over magnesium sulfate, the solvent was removed, and the residue was purified by flash silica gel column chromatography (acetone:hexane=2:1), yielding 4.85 g (90%) of the product as a yellow foam.

IR(KBr): 1797, 1721, 1496 cm$^{-1}$, MS(ISP): 708 (M+H)$^+$

According to the procedure set forth in the preceding examples, the following additional compounds were prepared:

7.3. Mixture of (E)-(5R,6R,7R)- and -(5S,6R,7R)-7-tert-butoxycarbonylamino-3-[1-(3-nitro-phenyl)-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1797, 1721 cm$^{-1}$, MS (ISP): 716.4 (M+NH$_4$)$^+$ 7.4. Mixture of (E)-(5R,6R,7R)- and -(5S,6R,7R)-7-tert-butoxycarbonylamino-3-(1-naphthalen-1-yl-2-oxo-pyrrolidin-3-ylidenemethyl)-5,8-dioxo-5-thia-bicyclo[4.2.0]oct-2-ene-2-carboxylic acid benzhydryl ester IR (KBr): 1797, 1722, 1049 cm$^{-1}$, MS (ISP): 704.5 (M+H)$^+$ 7.5. Mixture of (E)-(5R,6R,7R)- and -(5S,6R,7R)-7-tert-butoxycarbonylamino-3-[1-(4-tert-butoxycarbonyl-phenyl)-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1799, 1710 cm$^{-1}$, MS (ISP): 754.3 (M+H)$^+$ 7.6. Mixture of (E)-(5R,6R,7R)- and -(5S,6R,7R)-7-tert-butoxycarbonylamino-3-[1-(3-tert-butoxycarbonyloxy-phenyl)- 2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1798, 1758, 1723 cm$^{-1}$, MS (ISP): 770.2 (M+H)$^+$ 7.7. Mixture of (E)-(5R,6R,7R)- and -(5S,6R,7R)-7-tert-butoxycarbonylamino-3-[1-(2-diphenyl-1,3-benzodioxol-5-yl)-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1798, 1723 cm$^{-1}$, MS (ISP): 850.2 (M+H)$^+$ 7.8. Mixture of (E)-(5R,6R,7R)- and -(5S,6R,7R)-7-tert-butoxycarbonylamino-3-[1-(4-tert-butoxycarbonyloxy-3-fluoro-phenyl)-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1789, 1767, 1723 cm$^{-1}$, MS (ISP): 788.3 (M+H)$^+$ 7.9. Mixture of (E)-(5R,6R,7R)- and -(5S,6R,7R)-7-tert-butoxycarbonylamino-5,8-dioxo-3-[2-oxo-1-(4-tritylcarbamoyl-phenyl)-pyrrolidin-3-ylidenemethyl]-5-thia-1-aza-bicyclo[4.2.0]oct-2-ene-2-carboxylic acid benzhydryl ester IR (KBr): 1795, 1718, 1671 cm$^{-1}$, MS (ISP): 939.4 (M+H)$^+$ 7.10. Mixture of (E)-(5R,6R,7R)- and -(5S,6R,7R)-7-tert-butoxycarbonylamino-3-[1-(2-methoxy-phenyl)- 2-oxo-pyrrolidin-3-ylidenemethyl]-5,8-dioxo-5-thia-1-aza-bicyclo[4.2.0]oct-2-ene-2-carboxylic acid benzhydryl ester.

IR (KBr): 1797, 1719 cm$^{-1}$, MS (ISP): 684.3 (M+H)$^+$ 7.11. Mixture of (E)-(5R,6R,7R)- and -(5S,6R,7R)-7-tert-butoxycarbonylamino-3-[1-(tert-butoxycarbonyl-phenyl-methyl)-2-oxo-pyrrolidin-3-ylidenemethyl]-5,8-dioxo-5-thia-1-aza-bicyclo[4.2.0]oct-2-ene-2-carboxylic acid benzhydryl ester (config. in -phenyl-methyl-moiety R:S= 1:1)

IR (KBr): 1798, 1727, 1695 cm$^{-1}$, MS (ISP): 768.1 (M+H)$^+$ 7.12. Mixture of (E)-(5R,6R,7R)- and -(5S,6R,7R)-7-tert-butoxycarbonylamino-3-[1-(2-fluoro-benzyl)-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1796, 1721, 1689 cm$^{-1}$, MS (ISP): 686.3 (M+H)$^+$ 7.13. Mixture of (E)-(5R,6R,7R)- and -(5S,6R,7R)-7-tert-butoxycarbonylamino-3-[1-(2-methoxy-benzyl)-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1795, 1721, 1687 cm$^{-1}$, MS (ISP): 698.3 (M+H)$^+$ 7.14. Mixture of (E)-(5R,6R,7R)- and -(5S,6R,7R)-7-tert-butoxycarbonylamino-3-[1-(3-tert-butoxycarbonyloxy-benzyl)-2-oxo-pyrrolidin-3-ylidenemethyl]-5,8-dioxo-5-thia-1-azabicyclo[4.2.0]oct-2-ene-2-carboxylic acid benzhydryl ester IR (KBr): 1797, 1758, 1723, 1690 cm$^{-1}$ 7.15. Mixture of (E)-(5R,6R,7R)- and -(5S,6R,7R)-7-tert-butoxycarbonylamino-3-[1-(3-fluoro-benzyl)-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 1795, 1721, 1690 cm$^{-1}$, MS (ISP): 686 (M+H)$^+$ 7.16. Mixture of (E)-(5R,6R,7R)- and -(5S,6R,7R)-7-tert-butoxycarbonylamino-3-[1-(3-methoxy-benzyl)-2-oxopyrrolidin-3-ylidenemethyl]-5,8-dioxo-5-thia-1-aza-bicyclo [4.2.0]oct-2-ene-2-carboxylic acid benzhydryl ester IR (KBr): 1795, 1721, 1685 cm$^{-1}$, MS (ISP): 698.2 (M+H)$^+$ 7.17. Mixture of (E)-(5R,6R,7R)- and -(5S,6R,7R)-7-tert-butoxycarbonylamino-3-[1-[4-(3-tert-butoxycarbonyl-propionylamino)-benzyl]-2-oxo-pyrrolidin-3-ylidenemethyl]-5,8-dioxo-5-thia-1-aza-bicyclo[4.2.0]oct-2-ene-2-carboxylic acid benzhydryl ester IR (KBr): 3425, 1796, 1723 cm$^{-1}$, MS (ISP): 856.8 (M+NH$_4$)$^+$ 7.18. Mixture of (E)-(5R,6R,7R)- and -(5S,6R,7R)-3-[1-(4-allyloxycarbonylamino-benzyl)-2-oxo-pyrrolidin-3-ylidenemethyl]-7-tert-butoxycarbonylamino-5,8-dioxo-5-thia-1-aza-bicyclo[4.2.0]oct-2-ene-2-carboxylic acid benzhydryl ester IR (KBr): 1796, 1723, 1525 cm$^{-1}$, MS (ISP): 789.9 (M+Na)$^+$ 7.19. Mixture of (E)-(5R,6R,7R)- and -(5S,6R,7R)-7-tert-butoxycarbonylamino-3-[1-(4-tert-butoxycarbonyl-benzyl)-2-oxo-pyrrolidin-3-ylidenemethyl)-5,8-dioxo-5-thia-1-aza-bicyclo[4.2.0]oct-2-ene-2-carboxylic acid benzhydryl ester IR (KBr): 1798, 1715 cm$^{-1}$, MS (ISP): 768.5 (M+H)$^+$ 7.20. Mixture of (E)-(5R,6R,7R)- and (5S,6R,7R)-7-tert-butoxycarbonylamino-3-[1-(4-nitro-benzyl)-2-oxo-pyrrolidin-3-ylidenemethyl]-5,8-dioxo-5-thia-1-aza-bicyclo [4.2.0]oct-2-ene-2-carboxylic acid benzhydryl ester IR (KBr): 1795, 1721, 1688 cm$^{-1}$, MS (ISP): 713.3 (M+H)$^+$ 7.21. Mixture of (E)-(5R,6R,7R)- and -(5S,6R,7R)-7-tert-butoxycarbonylamino-3-[1-(4-methoxy-benzyl)-2-oxo-pyrrolidin-3-ylidenemethyl]-5,8-dioxo-5-thia-1-aza-bicyclo [4.2.0]oct-2-ene-2-carboxylic acid benzhydryl ester IR (KBr): 1796, 1722, 1684 cm$^{-1}$, MS (ISP): 698.2 (M+H)$^+$ 7.22. Mixture of (E)-(5R,6R,7R)- and -(5S,6R,7R)-7-tert-butoxycarbonylamino-3-[1-(4-fluoro-benzyl)-2-oxo-pyrrolidin-3-ylidenemethyl]-5,8-dioxo-5-thia-1-aza-bicyclo [4.2.0]oct-2-ene-2-carboxylic acid benzhydryl ester IR (KBr): 1795, 1721, 1686 cm$^{-1}$, MS (ISP): 686.2 (M+H)$^+$ 7.23. Mixture of (E)-(5R,6R,7R)- and (5S,6R,7R)-7-tert-butoxycarbonylamino-5,8-dioxo-3-[2-oxo-1-(4-trifluoromethyl-benzyl)-pyrrolidin-3-ylidenemethyl]-5-thia-1-aza-bicyclo[4.2.0]oct-2-ene-2-carboxylic acid benzhydryl ester IR (KBr): 1797, 1722, 1498 cm$^{-1}$, MS (ISP): 736.3 (M+H)$^+$ 7.24. Mixture of (E)-(5R,6R,7R)- and (5S,6R,7R)-3-(1-benzyl-2-oxo-pyrrolidin-3-ylidenemethyl)-7-tert-butoxycarbonylamino-5,8-dioxo-5-thia-1-aza-bicyclo [4.2.0]oct-2-ene-2-carboxylic acid benzhydryl ester IR (KBr): 1796, 1722, 1686 cm$^{-1}$, MS (ISP): 668.3 (M+H)$^+$ 7.25. (E)-(5S,6R,7R)-7-tert-Butoxycarbonylamino-3-[1-(2-tert-butoxycarbonyloxy-phenyl)-2-oxo-pyrrolidin-3-ylidenemethyl]-5,8-dioxo-thia-1-aza-bicyclo[4.2.0]oct-2-ene-2-carboxylic acid benzhydryl ester IR (KBr): 1798, 1723 cm$^{-1}$, MS (ISP): 770.0 (M+H)$^+$ 7.26. Mixture of (E)-(5R,6R,7R)- and -(5S,6R,7R)-7-tert-butoxycarbonylamino-3-[1-(3-fluoro-2-hydroxy-phenyl)-2-oxo-pyrrolidin-3-ylidenemethyl]-5,8-dioxo-5-thia-1-aza-bicyclo[4.2.0]oct-2-ene-2-carboxylic acid benzhydryl ester $^1$H-NMR (CDCl$_3$, 250 MHz): 8.9 (s,1H), 6.7–7.5 (m,15H), 5.7–5.9 (m,2H), 4.5 (d,1H), 4.0 (d,1H), 3.6–3.8 (m,2H), 3.2 (d,1H), 2.6–3.0 (m,2H)

7.27. Mixture of (E)-(5R,6R,7R)- and -(5S,6R,7R)-7-tert-butoxycarbonylamino-3-[1-(4-tert-butoxycarbonyloxy-2-fluoro-phenyl)-2-oxo-pyrrolidin-3-ylidenemethyl]-5,8-dioxo-5-thia-1-aza-bicyclo[4.2.0]oct-2-ene-2-carboxylic acid benzhydryl ester $^1$H-NMR (CDCl$_3$, 250 MHz): 7.2–7.5 (m,11H), 7.0 (m,4H), 5.7–5.9 (m,2H), 4.5 (d,1H), 4.0 (d,1H), 3.5–3.8 (m,2H), 3.2 (d,1H), 2.5–2.9 (m,2H), 1.6 (s,9H), 1.5 (s,9H)

7.28. Mixture of (E)-(5R,6R,7R)- and -(5S,6R,7R)-7-tert-butoxycarbonylamino-3-[1-(2-fluoro-phenyl)-2-oxo-pyrrolidin-3-ylidenemethyl]-5,8-dioxo-5-thia-1-aza-bicyclo [4.2.0]oct-2-ene-2-carboxylic acid benzhydryl ester $^1$H-NMR (CDCl$_3$, 250 MHz): 6.9–7.5 (m,16H), 5.7–5.9 (m,2H), 4.5 (d,1H), 4.0 (d,1H), 3.6–3.9 (m,2H), 3.2 (d,1H), 2.5–3.0 (m,2H), 1.5 (s,9H)

7.29. Mixture of (E)-(5R,6R,7R)- and (5S,6R,7R)-7-tert-Butoxycarbonylamino-5,8-dioxo-3-(2-oxo-1-thiophen-2-ylmethyl-pyrrolidin-3-ylidenemethyl)-5-thia-1-aza-bicyclo [4.2.0]oct-2-ene-2-carboxylic acid benzhydryl ester IR(KBr): 1796, 1721, 1687, 1633 cm$^{-1}$, MS(ISP): 674.3 (M+H)$^+$ 7.30. Mixture of (E)-(5R,6R,7R)- and -(5S,6R,7R)-7-tert-Butoxycarbonylamino-5,8-dioxo-3-[2-oxo-1-(1-trityl-1H-tetrazol-5-ylmethyl)-pyrrolidin-3-ylidenemethyl]-5-thia-1-aza-bicyclo[4.2.0]oct-2-ene-2-carboxylic acid benzhydryl ester IR(KBr): 1797, 1722, 1495 cm$^{-1}$, MS(ISP): 919.4 (M+NH$_4$)$^+$ 7.31. Mixture of (E)-(5R,6R,7R)- and -(5S,6R,7R)-7-tert-Butoxycarbonylamino-5,8-dioxo-3-[2-oxo-1-(tetrahydro-furan-2-ylmethyl)-pyrrolidin-3-ylidenemethyl]-5-thia-1-aza-bicyclo[4.2.0]oct-2-ene-2-carboxylic acid benzhydryl ester (config. in furan-moiety R:S=1:1)

IR(KBr): 1795, 1721, 1684 cm$^{-1}$, MS(ISP): 662.2 (M+H)$^+$ 7.32. Mixture of (E)-(5S,6R,7R)- and -(5R,6R,7R)-7-tert-Butoxycarbonylamino-3-[1-(1-ethoxycarbonyl-piperidin-4-yl)-2-oxo-pyrrolidin-3-ylidenemethyl]-5,8-dioxo-5-thia-1-aza-bicyclo[4.2.0]oct-2-ene-2-carboxylicacid benzhydryl ester IR(KBr): 1797, 1723, 1691 cm$^{-1}$, MS(ISP): 733.5 (M+H)$^+$ 7.33. Mixture of (E)-(5R,6R,7R)- and -(5S,6R,7R)-3-[1-(1-Allyloxycarbonyl-piperidin-4-yl)-2-oxo-pyrrolidin-3-ylidenemethyl]-7-tert-butoxycarbonyl-amino-5,8-dioxo-5-thia-1-aza-bicyclo[4.2.0]oct-2-ene-2-carboxylic acid benzhydryl ester IR(KBr): 1797, 1720, 1699, 1499 cm$^{-1}$, MS(ISP): 745.1 (M+H)$^+$ 7.34. Mixture of (E)-(5R,6R,7R)- and (5S,6R,7R)-7-tert-Butoxycarbonylamino-3-[1-(2-chloro-pyridin-3-yl)-2-oxo-pyrrolidin-3-ylidenemethyl]-5,8-dioxo-5-thia-1-aza-bicyclo [4.2.0]oct-2-ene-2-carboxylic acid benzhydryl ester IR(KBr): 1797, 1720 cm$^{-1}$, MS(ISP): 689.4 (M+H)$^+$ 7.35. Mixture of (E)-(5R,6R,7R)- and -(5S,6R,7R)-7-tert-Butoxycarbonylamino-5,8-dioxo-3-[2-oxo-1-(2-oxo-tetrahydro-furan-3-yl)-pyrrolidin-3-ylidenemethyl]-5-thia-1-aza-bicyclo[4.2.0]oct-2-ene-2-carboxylic acid benzhydryl ester (config. in furan-moiety R:S=1:1)

IR(KBr): 1790, 1722, 1695 cm$^{-1}$, MS(ISP): 662.3 (M+H)$^+$ 7.36. (E)-(5R,6R,7R)- or -(5S,6R,7R)-7-tert-Butoxycarbonylamino-5,8-dioxo-3-[2-oxo-1-(3-carbamoyl-thiophen-2yl)-pyrrolidin-3-ylidenemethyl]-5-thia-1-aza-bicyclo[4.2.0]oct-2-ene-2-carboxylic acid benzhydryl ester (config. in furan-moiety R:S=1:1)

IR(KBr): 1793, 1716 cm$^{-1}$, MS(ISP): 703.2 (M+H)$^+$

8. De-oxygenation of the sulfoxide (5) Scheme 1

8.1. In presence of phosphorous tribromide 8.1.1. Preparation of (E)-(6R,7R)-7-tert-Butoxycarbonylamino-3-[1-(4-tert-butoxycarbonyloxy-phenyl)-2-oxo-pyrrolidin-3-ylidene]-8-oxo-5-thia-1-aza-bicyclo[4.2.0]oct-2-ene-2-carboxylic acid benzhydryl ester

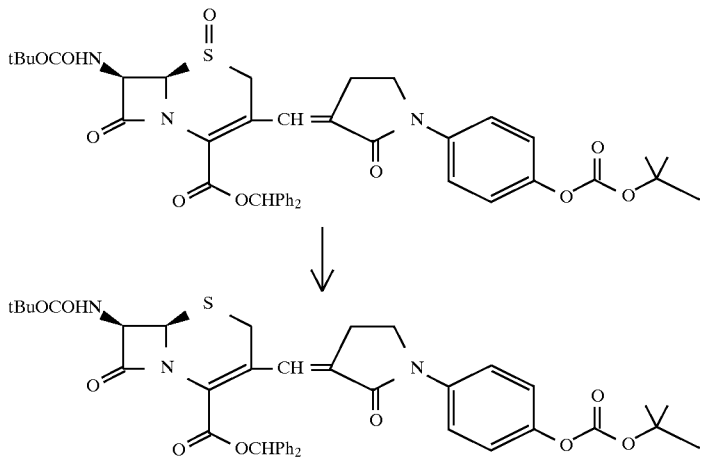

To a solution of 10.45 g (13.57 mmol) of a mixture of (E)-(5R,6R,7R)- and (5S,6R,7R)-7-tert-butoxycarbonylamino-3-[1-(4-tert-butoxycarbonyloxy-phenyl)-2-oxo-pyrrolidin-3-ylidenemethyl]- 5,8-dioxo-5-thia-1-aza-bicyclo[4.2.0]oct-2-ene-2 carboxylic acid benzhydryl ester in 120 ml dichloromethane, 12.1 ml N-methyl acetamide and 12.8 ml N,N-dimethylformamide was added at −30° C. a solution of 5.1 ml phosphorous tribromide in 15 ml dichloromethane. The mixture was stirred for 1 hour and then poured into a stirred solution of 20 g sodium bicarbonate in 250 ml ice-water. The organic phase was separated, washed with water, dried over magnesium sulfate and concentrated. The residue was digerated with n-hexane and the solid material collected by filtration (9.85 g, 96.3%).

IR(KBr): 1787, 1758, 1722 cm$^{-1}$; MS(ISP): 754.5 (M+H)$^+$ 8.1.2. (E)-(6R,7R)-3-[1-(1H-Benzimidazol-2-ylmethyl)-2-oxo-pyrrolidin-3-ylidenemethyl]-7-tert-butoxycarbonylamino-8-oxo-5-thia-1-aza-bicylco[4.2.0]oct-2-ene-2-carboxylic acid benzhydryl ester To a solution of 5.1 g (7.2 mmol) of a mixture of a mixture of (E)-(5R,6R, 7R)- and -(5S,6R,7R)-3-[1-(1H-benzimidazol-2-ylmethyl)-2-oxo-pyrrolidin-3-ylidenemethyl]-7-tert-butoxycarbonylamino-5,8-dioxo-5-thia-1-aza-bicyclo[4.2.0]oct-2-ene-2-carboxylic acid benzhydryl ester in 53 ml dichloromethane, 6.3 ml N-methyl acetamide and 6.8 ml N,N-dimethylformamide was added at −30° C. a solution of 2.7 ml (28.8 mmol) phosphorous tribromide in 13 ml dichloromethane. The mixture was stirred for 30 min and then poured on ice-water. The phases were separated and the aqueous phase was extracted twice with dichloromethane. The combined organic phases were washed with saturated sodium bicarbonate solution and water, dried over magnesium sulfate and concentrated. The residue was purified by silica gel chromatography (acetone:hexane=2:1).

yield: 3.1 g (62%) yellow powder.
IR(KBr): 1786, 1721, 1627 cm$^{-1}$, MS(ISP): 426.6 (M+H)$^+$ According to the procedure set forth in the preceding examples, the following additional compounds were prepared:

8.1.3. (E)-(6R,7R)-7-tert-Butoxycarbonylamino-3-[1-(3-nitro-phenyl)-2-oxo-pyrrolidin-3-ylidene]-8-oxo-5-thia-1-aza-bicyclo[4.2.0]oct-2-ene-2-carboxylic acid benzhydryl ester IR (KBr): 1787, 1721 cm$^{-1}$

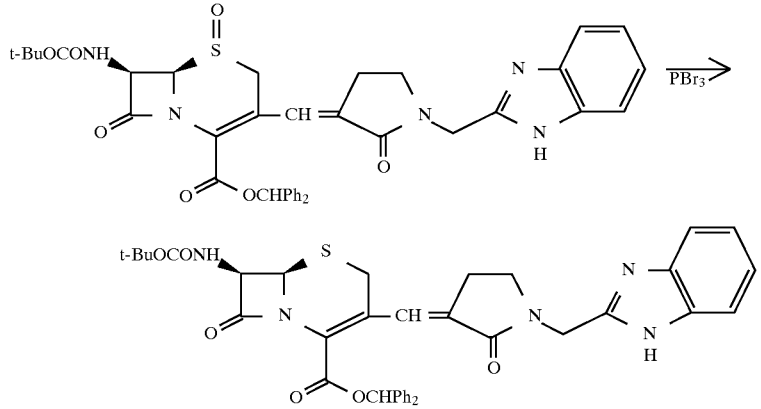

8.1.4. (E)-(6R,7R)-7-tert-Butoxycarbonylamino-3-(1-naphthalen-1-yl-2-oxo-pyrrolidin-3-ylidenemethyl)-8-oxo-5-thia-1-aza-bicyclo[4.2.0]oct-2-ene-2-carboxylic acid benzhydryl ester IR (KBr): 1785, 1720 cm$^{-1}$, MS (ISP): 688.3 (M+H)$^+$ 8.1.5. (E)-(6R,7R)-7-tert-Butoxycarbonylamino-3-[1-(2,2-diphenyl-1,3-benzodioxol-5-yl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1786, 1721, 1679 cm$^{-1}$, MS (ISP): 834.2 (M+H)$^+$ 8.1.6. (E)-(6R,7R)-7-tert-Butoxycarbonylamino-3-[1-(3-tert-butoxycarbonyloxy-phenyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1787, 1758, 1721 cm$^{-1}$, MS (ISP): 754.3 (M+H)$^+$ 8.1.7. (E)-(6R,7R)-7-tert-Butoxycarbonylamino-3-[1-(4-tert-butoxycarbonyloxy-3-fluoro-phenyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1772, 1721 cm$^{-1}$, MS (ISP): 772.3 (M+H)$^+$ 8.1.8. (E)-(6R,7R)-7-tert-Butoxycarbonylamino-8-oxo-3-[2-oxo-1-(4-tritylcarbamoyl-phenyl)-pyrrolidin-3-ylidenemethyl]-5-thia-1-aza-bicyclo[4.2.0]oct-2-ene-2-carboxylic acid benzhydryl ester IR (KBr): 1787, 1722, 1682 cm$^{-1}$, MS (ISP): 923.4 (M+H)$^+$ 8.1.9. (E)-(6R,7R)-7-tert-Butoxycarbonylamino-3-[1-(2-methoxy-phenyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1786, 1721 cm$^{-1}$, MS (ISP): 668.3 (M+H)$^+$ 8.1.10. (E)-(6R,7R)-7-tert-Butoxycarbonylamino-3-[1-(2-fluoro-benzyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1780, 1721, 1687 cm$^{-1}$, MS (ISP): 670.3 (M+H)$^+$ 8.1.11. (E)-(6R,7R)-7-tert-Butoxycarbonylamino-3-[1-(2-methoxy-benzyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1784, 1721, 1687 cm$^{-1}$, MS (ISP): 682.3 (M+H)$^+$ 8.1.12. (E)-(6R,7R)-7-tert-Butoxycarbonylamino-3-[1-(3-tert-butoxycarbonyloxy-benzyl)-2-oxo-pyrrolidin-3-ylidenemethyl]-8-oxo-5-thia-1-azabicyclo[4.2.0]oct-2-ene-2-carboxylic acid benzhydryl ester IR (KBr): 1786, 1758, 1721 cm$^{-1}$, MS (ISP): 785.1 (M+H)$^+$ 8.1.13. (E)-(6R,7R)-7-tert-Butoxycarbonylamino-3-[1-(3-fluoro-benzyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1784, 1721, 1688 cm$^{-1}$, MS (ISP): 669.8 (M+H)$^+$ 8.1.14. (E)-(6R,7R)-7-tert-Butoxycarbonylamino-3-[1-(3-methoxy-benzyl)-2-oxo-pyrrolidin-3-ylidenemethyl]-8-oxo- 5-thia-1-aza-bicyclo[4.2.0]oct-2-ene-2-carboxylic acid benzhydryl ester IR (KBr): 1785, 1720, 1686 cm$^{-1}$, MS (ISP): 682.2 (M+H)$^+$ 8.1.15. (E)-(6R,7R)-7-tert-Butoxycarbonylamino-3-[1-[4-(3-tert-butoxycarbonyl-propionylamino)-benzyl]-2-oxo-pyrrolidin-3-ylidenemethyl]-8-oxo-5-thia-1-aza-bicyclo[4.2.0]oct-2-ene-2-carboxylic acid benzhydryl ester IR (KBr): 1787, 1722, 1687 cm$^{-1}$, MS (ISP): 845.8 (M+Na)$^+$ 8.1.16. (E)-(6R,7R)-3-[1-(4-Allyloxycarbonylamino-benzyl)-2-oxo-pyrrolidin-3-ylidenemethyl]-7-tert-butoxycarbonylamino-8-oxo-5-thia-1-aza-bicyclo[4.2.0]oct-2-ene-2-carboxylic acid benzhydryl ester IR (KBr): 1784, 1722, 1529 cm$^{-1}$, MS (ISP): 773.6 (M+Na)$^+$ 8.1.17. (E)-(6R,7R)-7-tert-Butoxycarbonylamino-3-[1-(4-tert-butoxycarbonyl-benzyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1787, 1714 cm$^{-1}$, MS (ISP): 752.5 (M+H)$^+$ 8.1.18. (E)-(6R,7R)-7-tert-Butoxycarbonylamino-3-[1-(4-nitro-benzyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1785, 1720, 1688 cm$^{-1}$, MS (ISP): 697.3 (M+H)$^+$ 8.1.19. (E)-(6R,7R)-7-tert-Butoxycarbonylamino-3-[1-(4-methoxy-benzyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1784, 1722, 1685 cm$^{-1}$, MS (ISP): 682.2 (M+H)$^+$ 8.1.20. (E)-(6R,7R)-7-tert-Butoxycarbonylamino-3-[1-(4-fluoro-benzyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1783, 1722, 1685 cm$^{-1}$, MS (ISP): 670.2 (M+H)$^+$ 8.1.21. (E)-(6R,7R)-7-tert-Butoxycarbonylamino-8-oxo-3-[2-oxo-1-(4-trifluoromethyl-benzyl)-pyrrolidin-3-ylidenemethyl]-5-thia-1-aza-bicyclo[4.2.0]oct-2-ene-2-carboxylic acid benzhydryl ester IR (KBr): 1786, 1721, 1689 cm$^{-1}$, MS (ISP): 720.4 (M+H)$^+$ 8.1.22. (E)-(6R,7R)-3-(1-Benzyl-2-oxo-pyrrolidin-3-ylidenemethyl)-7-tert-butoxycarbonylamino-8-oxo-5-thia-1-aza-bicyclo[4.2.0]oct-2-ene-2-carboxylic acid benzhydryl ester IR (KBr): 1785, 1721, 1686 cm$^{-1}$, MS (ISP): 652.3 (M+H)$^+$ 8.1.23. Mixture of (E)-(6R,7R)-7-tert-butoxycarbonylamino-3-[1-[(R)- and -[(S)-tert-butoxycarbonyl-phenyl-methyl]-2-oxo-pyrrolidin-3-ylidenemethyl-8-oxo-5-thia-1-aza-bicyclo[4.2.0]oct-2-ene-2-carboxylic acid benzhydryl ester IR (KBr): 1788, 1728, 1690 cm$^{-1}$, MS (ISP): 752.1 (M+H)$^+$ 8.1.24. (E)-(6R,7R)-7-tert-Butoxycarbonylamino-3-[1-(3-methoxy-phenyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1786, 1721 cm$^{-1}$, MS (ISP): 668.4 (M+H)$^+$ 8.1.25. (E)-(6R,7R)-7-tert-Butoxycarbonylamino-3-(1-naphthalen-1-yl-2-oxo-pyrrolidin-3-ylidenemethyl)-8-oxo-5-thia-1-aza-bicyclo[4.2.0]oct-2-ene-2-carboxylic acid benzhydryl ester IR (KBr): 1785, 1721 cm$^{-1}$, MS (ISP): 688.4 (M+H)$^+$ 8.1.26. (E)-(6R,7R)-7-tert-Butoxycarbonylamino-3-[1-(3-fluoro-phenyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1787, 1721 cm$^{-1}$, MS (ISP): 656.3 (M+H)$^+$ 8.1.27. (E)-(6R,7R)-7-tert-Butoxycarbonylamino-8-oxo-3-[2-oxo-1-(3-trifluoromethyl-phenyl)-pyrrolidin-3- ylidenemethyl-phenyl)-pyrrolidin-3-ylidenemethyl]-5-thia-1-aza-bicyclo[4.2.0]oct-2-ene-2-carboxylic acid benzhydryl ester IR (KBr): 1785, 1721 cm⁻¹, MS (ISP): 706.3 (M+H)⁺

8.1.28. 1:1 Mixture of (E)-(6R,7R)-7-tert-Butoxycarbonylamino-8-oxo-3-[2-oxo-1-[(R)- and -[(S)-tetrahydro-furan-2-ylmethyl]-pyrrolidin-3-ylidenemethyl]-5-thia-1-aza-bicyclo[4.2.0]oct-2-ene-2-carboxylic acid benzhydryl ester IR(KBr): 1785, 1720, 1685 cm⁻¹, MS(ISP): 646.3 (M+H)⁺

8.1.29. (E)-(6R,7R)-7-tert-Butoxycarbonylamino-8-oxo-3-[2-oxo-1-(1-trityl-1H-tetrazol-5-ylmethyl)-pyrrolidin-3-ylidenemethyl]-5-thia-1-aza-bicyclo[4.2.0]oct-2-ene-2-carboxylic acid benzhydryl ester IR(KBr): 1785, 1720, 1640 cm⁻¹, MS(ISP): 903.4 (M+NH$_4$)⁺

8.1.30. (E)-(6R,7R)-7-tert-Butoxycarbonylamino-3-[1-(3,5-dimethyl-pyrazin-2-yl)-2-oxo-pyrrolidin-3-ylidenemethyl]-8-oxo-5-thia-1-aza-bicyclo[4.2.0]oct-2-ene-2-carboxylic acid benzhydryl ester IR(KBr): 1787, 1719, cm⁻¹, MS(ISP): 668.2 (M+H)⁺

8.1.31. (E)-(6R,7R)-3-[1-(1-Allyloxycarbonyl-piperidin-4-yl)-2-oxo-pyrrolidin-3-ylidenemethyl]-7-tert-butoxycarbonylamino-8-oxo-5-thia-1-aza-bicyclo[4.2.0]oct-2-ene-2-carboxylic acid benzhydryl ester IR(KBr): 1786, 1701 cm⁻¹, MS(ISP): 729.0 (M+H)⁺

8.1.32. (E)-(6R,7R)-7-tert-Butoxycarbonylamino-8-oxo-3-(2-oxo-1-piperidin-4-yl-pyrrolidin-3-ylidenemethyl)-5-thia-1-aza-bicyclo[4.2.0]oct-2-ene-carboxylic acid benzhydryl ester acetate IR(KBr): 1785, 1719, 1682, 1494 cm⁻¹, MS(ISP): 645.4 (M+H)⁺

8.1.33. (E)-(6R,7R)-7-tert-Butoxycarbonylamino-3-[1-(1-ethoxycarbonyl-piperidin-4-yl)-2-oxo-pyrrolidin-3-ylidenemethyl]-8-oxo-5-thia-1-aza-bicyclo[4.2.0]oct-2-ene-carboxylic acid benzhydryl ester IR(KBr): 1787, 1720, 1689 cm⁻¹, MS(ISP): 717.4 (M+H)⁺

8.1.34. (E)-(6R,7R)-7-tert-Butoxycarbonylamino-3-[1-[1-(3-tert-butoxycarbonyl-propionyl)-piperidin-4-yl]-2-oxo-pyrrolidin-3-ylidenemethyl]-8-oxo-5-thia-1-aza-bicyclo[4.2.0]oct-2-ene-2-carboxylic acid benzhydryl ester IR(KBr): 1786, 1722, 1688, 1645 cm⁻¹, MS(LPD): 823.8 (M+Na)⁺

8.1.35. (E)-(6R,7R)-7-tert-Butoxycarbonylamino-8-oxo-3-(2-oxo-1-pyrimidin-2-yl-pyrrolidin-3-ylidenemethyl)-5-thia-1-aza-bicyclo[4.2.0]oct-2-ene-2-carboxylic acid benzhydryl ester IR(KBr): 1784, 1717 cm⁻¹, MS(ISP): 640.4 (M+H)⁺

8.1.36. (E)-(6R,7R)-7-tert-Butoxycarbonylamino-8-oxo-3-[2-oxo-1-(1,3,4-thiadiazol-2-yl)-pyrrolidin-3-ylidenemethyl]-5-thia-1-aza-bicyclo[4.2.0]oct-2-ene-2-carboxylic acid benzhydryl ester IR(KBr): 1787, 1719 cm⁻¹, MS(ISP): 646.2 (M+H)⁺

8.1.37. (E)-(6R,7R)-7-tert-Butoxycarbonylamino-3-[1-(6-chloro-pyridazin-3-yl)-2-oxo-pyrrolidin-3-ylidenemethyl]-8-oxo-5-thia-1-aza-bicyclo[4.2.0]oct-2-ene-2-carboxylic acid benzhydryl ester IR(KBr): 1787, 1714, cm⁻¹, MS(ISP): 674.2 (M+H)⁺

8.1.38. (E)-(6R,7R)-7-tert-Butoxycarbonylamino-8-oxo-3-(2-oxo-1-thiophen-2-ylmethyl-pyrrolidin-3-ylidenemethyl)-5-thia-1-aza-bicyclo[4.2.0]oct-2-ene-2-carboxylic acid benzhydryl ester IR(KBr): 1783, 1720, 1686, 1633 cm⁻¹, MS(ISP): 658.3 (M+H)⁺

8.1.39. 1:1 Mixture of (E)-(6R,7R)-7-tert-Butoxycarbonylamino-8-oxo-3-[2-oxo-1-[(R)- and -[(S)-2-oxo-tetrahydro-furan-3-yl]-pyrrolidin-3-ylidenemethyl]-5-thia-1-aza-bicyclo[4.2.0]oct-2-ene-2-carboxylic acid benzhydryl ester IR(KBr): 1783, 1720, 1692 cm⁻¹, MS(ISP): 646.3 (M+H)⁺

8.1.40. (E)-(6R,7R)-7-tert-Butoxycarbonylamino-3-[1-(2-chloro-pyridin-3-yl)-2-oxo-pyrrolidin-3-ylidenemethyl]-8-oxo-5-thia-1-aza-bicyclo[4.2.0]oct-2-ene-2-carboxylic acid benzhydryl ester IR(KBr): 1785, 1718, cm⁻¹, MS(ISP): 696.1 (M+Na)⁺

8.1.41. (E)-(6R,7R)-7-tert-Butoxycarbonylamino-8-oxo-3-[2-oxo-1-(3-ethoxycarbonyl-thiophen-2yl)-pyrrolidin-3-ylidenemethyl]-5-thia-1-aza-bicyclo[4.2.0]oct-2-ene-2-carboxylic acid benzhydryl ester ¹H-NMR (CDCl3) d[ppm]=1.29 (t,3H); 1.49 (s,9H); 2.63 (m,1H); 2.82 (m,1H); 3.61 (m,3H); 3.81 (m,1H); 4.25 (q,2H); 5.03 (d, 1H); 5.29 (d, 1H); 5.67 (m,1H); 7.01 (s, 1H); 7.12 (d, 1H); 7.3–7.5 (m, 12H)

8.1.42. (E)-(6R,7R)-7-tert-Butoxycarbonylamino-8-oxo-3-[2-oxo-1-(3-cyano-thiophen-2yl)-pyrrolidin-3-ylidenemethyl]- 5-thia-1-aza-bicyclo[4.2.0]oct-2-ene-2-carboxylic acid benzhydryl ester IR(KBr): 1786, 1720 cm⁻¹, MS(ISP): 686.4 (M+NH$_4$)⁺

8.1.43. (E)-(6R,7R)-7-tert-Butoxycarbonylamino-8-oxo-3-[2-oxo-1-(3-carbamoyl-thiophen-2yl)-pyrrolidin-3-ylidenemethyl]-5-thia-1-aza-bicyclo[4.2.0]oct-2-ene-2-carboxylic acid benzhydryl ester IR(KBr): 1785, 1682 cm⁻¹, MS(ISP): 687.4 (M+H)⁺

8.2. In the presence of sodium iodide 8.2.1. Preparation of (E)-(6R,7R)-7-tert-Butoxycarbonylamino-3-[1-(3-fluoro-2-hydroxy-phenyl)-2-oxo-pyrrolidin-3-ylidenemethyl]-8-oxo-5-thia-1-aza-bicyclo[4.2.0]oct-2-ene-2-carboxylic acid benzhydryl ester

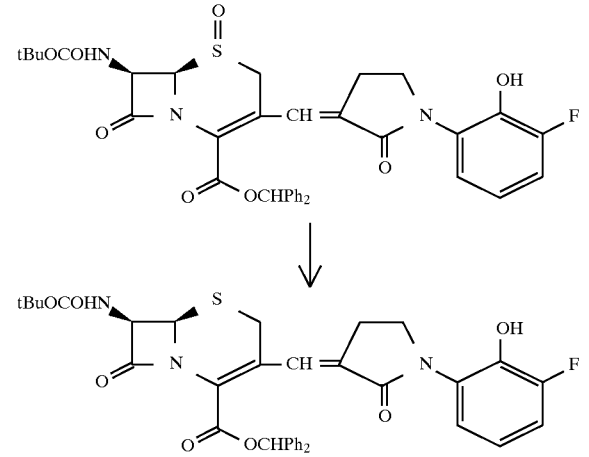

To a solution of 3.92 g (5.22 mmol) (E)-(5R,6R,7R)- and (5S,6R,7R)-7-tert-butoxycarbonylamino-3-[1-(3-fluoro-2-hydroxy-phenyl)-2-oxo-pyrrolidin-3-ylidenemethyl]-5,8-dioxo-5-thia-1-aza-bicyclo[4.2.0]oct-2-ene-2 carboxylic acid benzhydryl ester in 60 ml acetone was added 3.86 g (26.1 mmol) sodium iodide. The mixture was cooled to −20° C. and 3.6 ml (26.1 mmol) trifluoroacetic acid anhydride were added within 10 min, the temperature being kept below 0° C. After 1 h, ethylacetate was added and the mixture was washed twice with 50 ml 10% sodium bisulfite solution and brine. The organic phase was dried over sodium sulfate and evaporated. The residue was stirred with diethylether and hexane and the solid was collected by filtration and dried. yield: 3.07 g (88%).

¹H-NMR (250 MHz, CDCl$_3$): 6.8–7.5 (m, 15H); 5.7 (m, 1H); 5.4 (d, 1H); 5.0 (d, 1H), 3.5–3.9 (m, 4H); 2.5–2.9 (m, 2H); 1.5 (s, 9H).

According to the procedure set forth in the preceding example, the following additional compounds were prepared:

8.2.2. (E)-(6R,7R)-7-tert-Butoxycarbonylamino-3-[1-(2-fluoro-phenyl)-2-oxo-pyrrolidin-3-ylidenemethyl]-8-oxo-5-thia-1-aza-bicyclo[4.2.0]oct-2-ene-2-carboxylic acid benzhydryl ester $^1$H-NMR (CDCl$_3$, 250 MHz): 7.1–7.4 (m,15H), 7.0 (s,1H), 5.7 (m,1H), 5.4 (dd,1H), 3.6–3.8 (m,4H), 2.5–2.9 (m,2H), 1.5 (s,9H).

8.2.3. (E)-(6R,7R)-7-tert-Butoxycarbonylamino-3-[1-(4-tert-butoxycarbonyloxy-2-fluoro-phenyl)-2-oxo-pyrrolidin-3-ylidenemethyl]-8-oxo-5-thia-1-aza-bicyclo[4.2.0]oct-2-ene-2-carboxylic acid benzhydryl ester $^1$H-NMR (CDCl$_3$, 250 MHz): 7.2–7.5 (m,12H), 7.0 (m,3H), 5.7 (m,1H), 5.3 (d,1H), 5.0 (d,1H), 3.5–3.8 (m,4H), 2.5–2.9 (m,2H), 1.6 (s,9H), 1.5 (s,9H)

8.2.4. (E)-(6R,7R)-7-tert-Butoxycarbonylamino-3-[1-(2-tert-butoxycarbonyloxy-phenyl)-2-oxo-pyrrolidin-3-ylidenemethyl]-8-oxo-5-thia-1-aza-bicyclo[4.2.0]oct-2-ene-2-carboxylic acid benzhydryl ester IR (KBr): 1784, 1721 cm$^{-1}$, MS (ISP): 753.9 (M+H)$^+$ 9. Removing the amino and/or carboxy-protecting groups (Scheme 1 (6)→(7))

9.1. In the presence of trifluoroacetic acid and anisole 9.1.1. Preparation of (E)-(6R,7R)-7-Amino-3-[1-(4-hydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate To a solution of 9.78 g (12.97 mmol) (E)-(6R,7R)-7-tert-butoxycarbonylamino-3-[1-(4-tert-butoxycarbonyloxy-phenyl)-2-oxo-pyrrolidin-3-ylidenemethyl]-8-oxo-5-thia-1-aza-bicyclo[4.2.0]oct-2-ene-2 carboxylic acid benzhydryl ester in 100 ml dichloromethane and 10 ml anisole was added 50 ml trifluoroacetic acid at 0° C. After 2 h at rt, the mixture was concentrated and poured on diethylether. The resulting solid was collected by filtration and washed with diethylether and hexane (5.12 g, 96.2%).

IR(KBr): 1778, 1676 cm$^{-1}$, MS (ISP): 388.4 (M+H)$^+$ 9.1.2. (E)-(6R,7R)-7-Amino-3-[1-(1H-benzimidazol-2-ylmethyl)-2-oxo-pyrrolidin-3-ylidenemethyl]-8-oxo-5-thia-1-aza-bicylco[4.2.0]oct-2-ene-2-carboxylic acid trifluoroacetate

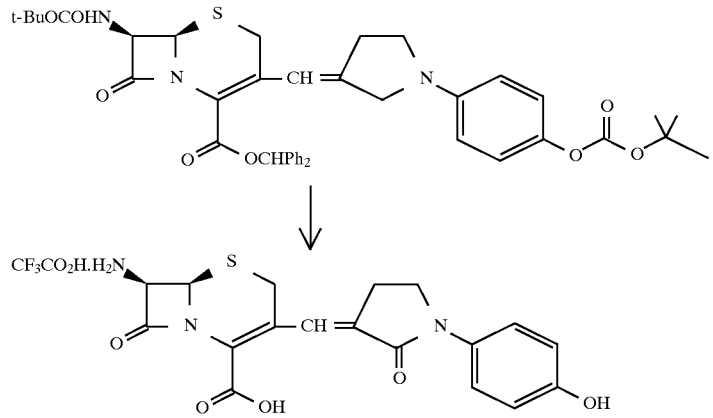

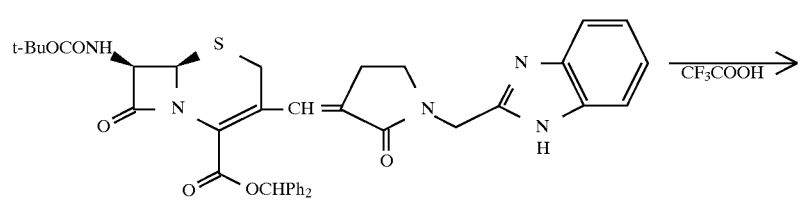

-continued

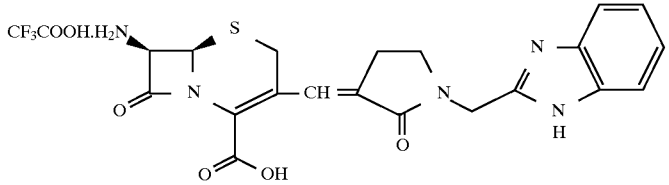

To a solution of 0.5 g (0.72 mmol) (E)-(6R,7R)-3-[1-(1H-benzimidazol-2-ylmethyl)-2-oxo-pyrrolidin-3-ylidenemethyl]-7-tert-butoxycarbonylamino-8-oxo-5-thia-1-aza-bicylco[4.2.0]oct-2-ene-2-carboxylic acid benzhydryl ester in 4.8 ml dichloromethane and 0.45 ml anisole was added 2.42 ml trifluoroacetic acid at 0° C. After 4.5 h, the mixture was concentrated and the residue dissolved in dichloromethane and treated with diethylether. The resulting solid was collected by filtration, stirred with ethyl acetate and collected by filtration.

yield: 185 mg (60%) beige powder
IR(KBr): 1777, 1677, 1625 cm$^{-1}$, MS(ISP): 692.8 (M+H)$^+$ According to the procedure set forth in the preceding examples, the following additional compounds were prepared:

9.1.3. (E)-(6R,7R)-7-Amino-3-[1-(3-nitro-phenyl)-2-oxo-pyrrolidin-3-ylidenemethyl]-8-oxo-5-thia-1-aza-bicyclo[4.2.0]oct-2-ene-carboxylic acid trifluoroacetate
IR (KBr): 1785, 1690 cm$^{-1}$, MS (ISP): 415.4 (M–H)$^-$ 9.1.4. (6R,7R)-7-Amino-3-[1-(4-carboxy-phenyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1786, 1691 cm$^{-1}$, MS (ISP): 416.3 (M+H)$^+$ 9.1.5. (E)-(6R,7R)-7-Amino-3-[1-(3-methoxy-phenyl)-2-oxo-pyrrolidin-3-ylidenemethyl]-8-oxo-5-thia-1-aza-bicyclo[4.3.0]oct-2-ene-2-carboxylic acid trifluoroacetate
IR (KBr): 1789, 1687 cm$^{-1}$, MS (ISP): 402.4 (M+H)$^+$ 9.1.6. (E)-(6R,7R)-7-Amino-3-[1-(3-fluoro-phenyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1795, 1692 cm$^{-1}$, MS (ISP): 390 (M+H)$^+$ 9.1.7. (E)-(6R,7R)-7-Amino-3-[1-(3-hydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1785 cm$^{-1}$ 9.1.8. (E)-(6R,7R)-7-Amino-3-[1-(3,4-dihydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1775, 1673 cm$^{-1}$, MS (ISP): 404.2 (M+H)$^+$ 9.1.9. (E)-(6R,7R)-7-Amino-3-[1-(3-fluoro-4-hydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1776, 1678 cm$^{-1}$, MS (ISP): 406.3 (M+H)$^+$ 9.1.10. (E)-(6R,7R)-7-Amino-3-[1-(2-methoxy-phenyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1781, 1684 cm$^{-1}$, MS (ISP): 402.3 (M+H)$^+$ 9.1.11. (E)-(6R,7R)-7-Amino-3-[1-(3-fluoro-2-hydroxy-phenyl)-2-oxo-pyrrolidin-3-ylidenemethyl-8-oxo-5-thia-1-aza-bicyclo[4.2.0]oct-2-ene-2-carboxylic acid trifluoroacetate
$^1$H-NMR (DMSO, 250 MHz): 9.8 (b,1H), 6.8–7.4 (m,6H), 5.2 (dd,2H), 4.0 (b,2H), 3.7 (m,2H), 3.1–3.3 (m,2H)

9.1.12. (E)-(6R,7R)-7-Amino-3-[1-(2-fluoro-4-hydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate
$^1$H-NMR (DMSO, 250 MHz): 10.1 (sb,1H), 7.4 (s,1H), 7.2 (m,2H), 6.9–7.2 (m,2H), 6.7 (m,2H), 5.2 (dd,2H), 4.0 (dd,2H), 3.7 (m,2H), 3.0–3.3 (m,2H)

9.1.13. (E)-(6R,7R)-7-Amino-3-[1-(2-fluoro-phenyl)-2-oxo-pyrrolidin-3-ylidenemethyl]-8-oxo-5-thia-1-aza-bicyclo[4.2.0]oct-2-ene-2-carboxylic acid trifluoroacetate
$^1$H-NMR (DMSO, 250 MHz): 6.9–7.6 (m,7H), 5.1 (d,1H), 4.9 (d,1H), 3.9 (sb,2H), 3.8 (m,2H), 3.1–3.4 (m,2H)

9.1.14. (E)-(6R,7R)-7-Amino-3-[1-(2-hydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1794, 1620 cm$^{-1}$, MS (ISN): 386.2 (M–H)$^-$ 9.1.15. Mixture of (E)-(6R,7R)-7-amino-3-[1-[(R)- and -[(S)-carboxy-phenyl-methyl]-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1786, 1743, 1681, 1623 cm$^{-1}$, MS (ISP): 430.2 (M+H)$^+$ 9.1.16. (E)-(6R,7R)-7-Amino-3-[1-(2-fluoro-benzyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 3435, 1785, 1682 cm$^{-1}$, MS (ISP): 404.3 (M+H)$^+$ 9.1.17. (E)-(6R,7R)-7-Amino-3-[1-(2-methoxy-benzyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1788, 1680, 1623 cm$^{-1}$, MS (ISP): 416.4 (M+H)$^+$ 9.1.18. (E)-(6R,7R)-7-Amino-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1788, 1677, 1617 cm$^{-1}$, MS (ISP): 402.3 (M+H)$^+$ 9.1.19. (E)-(6R,7R)-7-Amino-3-[1-(3-fluoro-benzyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1787, 1682, 1616 cm$^{-1}$, MS (ISP): 404.3 (M+H)$^+$ 9.1.20. (E)-(6R,7R)-7-Amino-3-[1-(3-methoxy-benzyl)-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1687, 1681, 1610 cm$^{-1}$, MS (ISP): 416.4 (M+H)$^+$ 9.1.21. (E)-(6R,7R)-7-Amino-3-[1-[4-(3-carboxy-propionylamino)-benzyl]-2-oxo-pyrrolidin-3-ylidenemethyl]-8-oxo-5-thia-1-aza-bicyclo[4.2.0]oct-2-ene-2-carboxylic acid trifluoroacetate
IR (KBr): 1781, 1670, 1605 cm$^{-1}$, MS (ISP): 523.5 (M+Na)$^+$ 9.1.22. (E)-(6R,7R)-3-[1-(4-Allyloxycarbonylamino-benzyl)-2-oxo-pyrrolidin-3-ylidenemethyl]-7-amino-8-oxo-5-thia-1-aza-bicyclo[4.2.0]oct-2-ene-2-carboxylic acid trifluoroacetate
IR (KBr): 3411, 1781, 1724, 1676 cm$^{-1}$, MS (ISP): 507.5 (M+Na)$^+$ 9.1.23. (E)-(6R,7R)-7-Amino-3-[1-(4-carboxy-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1784, 1682, 1614 cm$^{-1}$, MS (ISP): 430.3 (M+H)$^+$ 9.1.24. (E)-(6R,7R)-7-Amino-3-[1-(4-nitro-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1781, 1679, 1611 cm$^{-1}$, MS (ISP): 431.3 (M+H)$^+$ 9.1.25. (E)-(6R,7R)-7-Amino-(4-methoxy-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 3433, 1786, 1679, 1613 cm$^{-1}$, MS (ISP): 416.4 (M+H)$^+$ 9.1.26. (E)-(6R,7R)-7-Amino-3-[1-(4-fluoro-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1783, 1683, 1605 cm$^{-1}$, MS (ISP): 404.3 (M+H)$^+$ 9.1.27. (E)-(6R,7R)-7-Amino-8-oxo-3-[2-oxo-1-(4-trifluoromethyl-benzyl)-pyrrolidin-3-ylidenemethyl]-5-thia-1-aza-bicyclo[4.2.0]oct-2-ene-2-carboxylic acid trifluoroacetate IR (KBr): 1783, 1681, 1620 cm$^{-1}$, MS (ISP): 454.4 (M+H)$^+$ 9.1.28. (E)-(6R,7R)-7-Amino-3-(1-benzyl-2-oxo-pyrrolidin-3-ylidenemethyl)-8-oxo-5-thia-1-aza-bicyclo[4.2.0]oct-2-ene-2-carboxylic acid trifluoroacetate IR (KBr): 1786, 1682, 1619 cm$^{-1}$, MS (ISP): 386.3 (M+H)$^+$ 9.1.29. ((E)-(6R,7R)-7-Amino-8-oxo-3-[2-oxo-1-(1-tetrazol-5-ylmethyl)-pyrrolidin-3-ylidenemethyl]-5-thia-1-aza-bicyclo[4.2.0]oct-2-ene-2-carboxylic acid trifluoroacetate IR(KBr): 1781, 1679, 1630 cm$^{-1}$, MS(ISP): 378.3 (M+H)$^+$ 9.1.30. 1:1 Mixture of (E)-(6R,7R)-7-Amino-8-oxo-3-[2-oxo-1-[(R)- and -[(S)-tetrahydro-furan-2-ylmethyl]-pyrrolidin-3-ylidenemethyl]-5-thia-1-aza-bicyclo[4.2.0]oct-2-ene-2-carboxylic acid trifluoroacetate IR(KBr): 1785, 1680, 1622 cm$^{-1}$, MS(ISP): 380.3 (M+H)$^+$ 9.1.31. (E)-(6R,7R)-7-Amino-3-[1-(3,5-dimethyl-pyrazin-2-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1786, 1694, 1619 cm$^{-1}$, MS(ISP): 402.3 (M+H)$^+$ 9.1.32. (E)-(6R,7R)-7-Amino-8-oxo-3-(2-oxo-1-pyrimidin-2-yl-pyrrolidin-3-ylidenemethyl)-5-thia-1-aza-bicyclo[4.2.0]oct-2-ene-2-carboxylic acid trifluoroacetate IR(KBr): 1781, 1701, 1620 cm$^{-1}$, MS(ISP): 374.3 (M+H)$^+$ 9.1.33. (E)-(6R,7R)-7-Amino-3-[1-(6-chloro-pyridazin-3-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1782, 1699, 1625 cm$^{-1}$, MS(ISP): 408.2 (M+H)$^+$ 9.1.34. (E)-(6R,7R)-7-Amino-3-[1-(2-chloro-pyridin-3-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1782, 1694 cm$^{-1}$, MS(ISN): 422.3 (M–H+NH$_3$)$^-$ 9.1.35. (E)-(6R,7R)-7-Amino-3-[1-[1-(3-carboxy-propionyl)-piperidin-4-yl]-2-oxo-pyrrolidin-3-ylidenemethyl]-8-oxo-5-thia-1-aza-bicyclo[4.2.0]oct-2-ene-2-carboxylic acid trifluoroacetate IR(KBr): 1784, 1674, 1626 cm$^{-1}$, MS(LPD): 501.1 (M+Na)$^+$ 9.1.36. (E)-(6R,7R)-3-[1-(1-Allyloxycarbonyl-piperidin-4-yl)-2-oxo-pyrrolidin-3-ylidenemethyl]-7-amino-8-oxo-5-thia-1-aza-bicyclo[4.2.0]oct-2-ene-2-carboxylic acid trifluoroacetate IR(KBr): 1778, 1695 cm$^{-1}$, MS(ISP): 463.0 (M+H)$^+$ 9.1.37. (E)-(6R,7R)-7-Amino-3-[1-(1-ethoxycarbonyl-piperidin-4-yl)-2-oxo-pyrrolidin-3-ylidenemethyl]-8-oxo-5-thia-1-aza-bicyclo[4.2.0]oct-2-ene-carboxylic acid trifluoroacetate IR(KBr): 1789, 1685 cm$^{-1}$, MS(ISP): 451.3 (M+H)$^+$ 9.1.38. 1:1 Mixture of (E)-(6R,7R)-7-Amino-8-oxo-3-[2-oxo-1-[(R)- and -[(S)-2-oxo-tetrahydro-furan-3-yl]-pyrrolidin-3-ylidenemethyl]-5-thia-1-aza-bicyclo[4.2.0]oct-2-ene-2-carboxylic acid trifluoroacetate IR(KBr): 1777, 1678, 1632 cm$^{-1}$, MS(ISP): 380.3 (M+H)$^+$ 9.1.39. (E)-(6R,7R)-7-Amino-8-oxo-3-[2-oxo-1-(1,3,4-thiadiazol-2-yl)-pyrrolidin-3-ylidenemethyl]-5-thia-1-aza-bicyclo[4.2.0]oct-2-ene-2-carboxylic acid trifluoroacetate IR(KBr): 1783, 1694, 1621 cm$^{-1}$, MS(ISP): 380.2 (M+H)$^+$ 9.1.40. (E)-(6R,7R)-7-Amino-8-oxo-3-(2-oxo-1-thiophen-2-ylmethyl-pyrrolidin-3-ylidenemethyl)-5-thia-1-aza-bicyclo[4.2.0]oct-2-ene-2-carboxylic acid benzhydryl ester trifluoroacetate IR(KBr): 1785, 1681, 1622, 1406 cm$^{-1}$, MS(ISP): 392.3 (M+H)$^+$ 9.1.41. (E)-(6R,7R)-7-Amino-8-oxo-3-(2-oxo-1-(3-ethoxycarbonyl-thiophen-2-yl)-pyrrolidin-3-ylidenemethyl)-5-thia-1-aza-bicyclo[4.2.0]oct-2-ene-2-carboxylic acid trifluoroacetate IR(KBr): 1773, 1703 cm$^{-1}$, MS(ISP): 450 (M+H)$^+$ 9.1.42. (E)-(6R,7R)-7-Amino-8-oxo-3-(2-oxo-1-(3-carbamoyl-thiophen-2-yl)-pyrrolidin-3-ylidenemethyl)-5-thia-1-aza-bicyclo[4.2.0]oct-2-ene-2-carboxylic acid trifluoroacetate IR(KBr): 1792, 1682 cm$^{-1}$, MS(ISN): 419.2 (M–H)$^-$ 9.1.43. (E)-(6R,7R)-7-Amino-8-oxo-3-(2-oxo-1-(3-cyano-thiophen-2-yl)-pyrrolidin-3-ylidenemethyl)-5-thia 1-aza-bicyclo[4.2.0]oct-2-ene-2 carboxylic acid trifluoroacetate IR(KBr): 1785, 1685 cm$^{-1}$, MS(ISP): 403.1 (M+H)$^+$ 9.2. In the presence of trifluoroacetic acid and triethylsilane 9.2.1. Preparation of (E)-(6R,7R)-7-Amino-3-[1-(4-carbamoyl-phenyl)-2-oxo-pyrrolidin-3-ylidenemethyl]-8-oxo-5-thia-1-aza-bicyclo[4.2.0]oct-2-ene-2-carboxylic acid trifluoroacetate

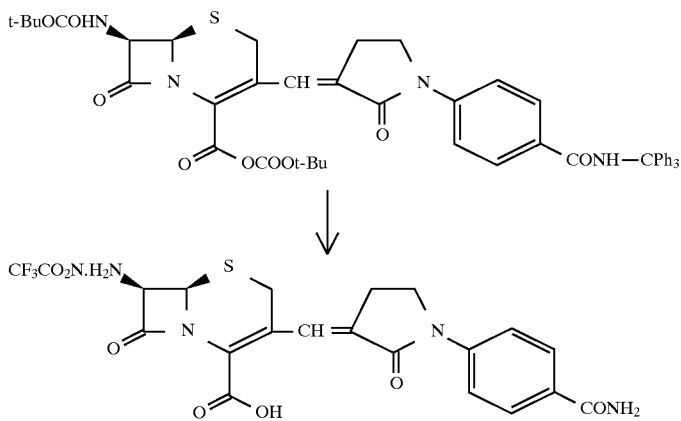

To a cooled solution of 1.39 ml (8.78 mmol) triethylsilane in 28 ml trifluoroacetic acid was added portionwise 7.72 g (8.36 mmol) (E)-(6R,7R)-7-tert-butoxycarbonylamino-8-oxo-3-[2-oxo-1-(4-tritylcarbamoyl-phenyl)-pyrrolidin-3-ylidenemethyl]-5-thia-1-aza-bicylco[4.2.0]oct-2-ene-2-carboxylic acid benzhydryl ester. After 45 min at 0° C. and 4 h at rt, the mixture was concentrated to ½ of its volume and was poured on 50 ml ice-cold diethylether and stirred for 1 h. The solid was collected by filtration and dried yielding 3.88 g (99%) of a yellow material.

IR(KBr): 1778, 1666 cm$^{-1}$, MS(ISP): 415.3 (M+H)$^+$

According to the procedure set forth in the preceding example, the following additional compounds were prepared:

9.2.2. (E)-(6R,7R)-7-Amino-8-oxo-3-[2-oxo-1-(3-trifluoromethyl-phenyl)-pyrrolidin-3-ylidenemethyl]-5-thia-1-aza-bicyclo[4.2.0]oct-2ene-2-carboxylic acid trifluoroacetate IR (KBr): 1791, 1691 cm$^{-1}$, MS (ISP): 440.4 (M+H)$^+$ 9.2.3. (E)-(6R,7R)-7-Amino-3-(1-naphthalen-2-yl-2-oxo-pyrrolidin-3-ylidenemethyl)-8-oxo-5-thia-1-aza-bicyclo[4.2.0]oct-2-ene-2-carboxylic acid trifluoroacetate IR (KBr): 1787, 1686 cm$^{-1}$, MS (ISP): 422.4 (M+H)$^+$ 9.2.4. (E)-(6R,7R)-7-Amino-2-(1-naphthalen-1-yl-2-oxo-pyrrolidin-3-ylidenemethyl)-8-oxo-5-thia-1-aza-bicyclo[4.2.0]oct-2-ene-2-carboxylic acidtrifluoroacetate IR (KBr): 1779, 1686 cm$^{-1}$, MS (ISP): 422.4 (M+H)$^+$ 10. Acylation of compound (7) (Scheme 1 (7)→(8))

10.1. Preparation of (6R,7R)-7-[(Z)-2-(2-Amino-thiazol-4-yl)-2-trityloxyimino-acetylamino]-3-[(E)-1-(4-hydroxy-phenyl)- 2-oxo-pyrrolidin-3-ylidenemethyl]-8-oxo-5-thia-1-aza-bicyclo[4.2.0]oct-2-ene-2-carboxylic acid

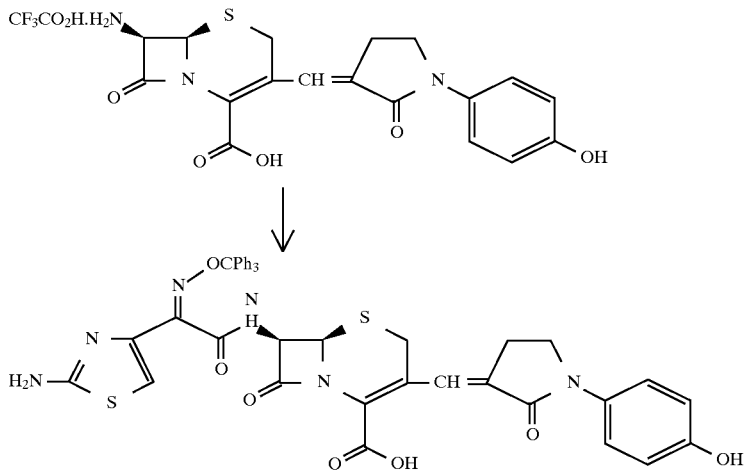

To a stirred suspension of 820 mg (2 mmol) (E)-(6R,7R)-7-amino-3-[1-(4-hydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate was added 1.4 g (2.56 mmol) 2-(2-aminothiazol-4-yl)-(Z)-2-trityloxyimino-acetic acid 1-benzotriazole ester. After 20 h at rt, the mixture was concentrated and the residue dissolved in 150 ml ethylacetate and washed twice with 25 ml water. The organic phase was concentrated to about ⅓ of its volume, upon which the product started to crystallize. It was collected by filtration, washed with ethylacetate and diethylether and dried to yield 1.12 g (70%) yellow crystals.

IR(KBr): 1784, 1679 cm$^{-1}$, MS(ISP): 799.4 (M+H)$^+$ 10.2. (6R,7R)-7-[(Z)-2-Amino-thiazol-4-yl)-2-trityloxyimino-acetylamino]-3-[(E)-1-(1H-benzimidazol-2-ylmethyl)- 2-oxo-pyrrolidin-3-ylidenemethyl]-8-oxo-5-thia-1-aza-bicylco[4.2.0]oct-2-ene-2-carboxylic acid

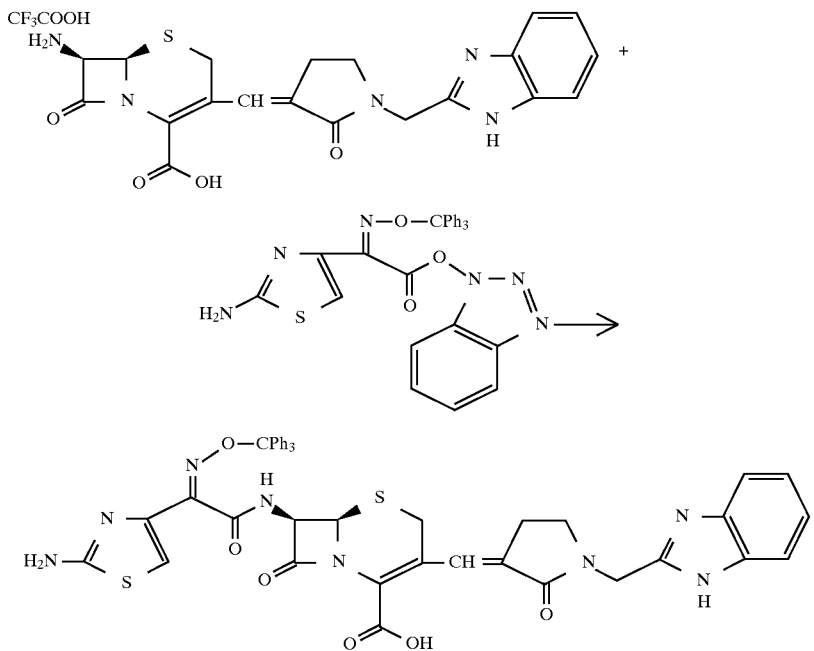

To a stirred suspension of 670 mg (1.31 mmol) (E)-(6R,7R)-7-amino-3-[1-(1H-benzimidazol-2-ylmethyl)-2-oxo-pyrrolidin-3-ylidenemethyl]-8-oxo-5-thia-1-aza-bicylco[4.2.0]oct-2-ene-2-carboxylic acid trifluoroacetate in 22 ml DMF was added 0.785 g (1.44 mmol) 2-(2-aminothiazol-4-yl)-(Z)-2-trityloxyimino-acetic acid 1-benzotriazole ester. After 21 h at room temperature, the mixture was concentrated and the residue suspended in 700 ml ethyl acetate and the solid collected by filtration. It was suspended in 10 ml water and stirred for 1.5 h, collected by filtration, washed with water, ethanol and diethylether and dried to yield 635 mg (58%) of a beige powder.

IR(KBr): 1777, 1677, 1625 cm$^{-1}$, MS(ISP): 837.2 (M+H)$^+$

According to the procedure set forth in the preceding examples, the following additional compounds were prepared:

10.3. (6R,7R)-7-[(Z)-2-(2-Amino-thiazol-4-yl)-2-trityloxyimino-acetylamino]-3-[(E)-1-(3-nitro-phenyl)-2-oxo-pyrrolidin-3-ylidenemethyl]-8-oxo-5-thia-1-aza-bicyclo[4.2.0]oct-2-ene-2-carboxylic acid IR (KBr): 1785, 1689 cm$^{-1}$, MS (ISP): 828.4 (M+H)$^+$ 10.4. (6R,7R)-7-[(Z)-2-(2-Amino-thiazol-4-yl)-2-trityloxyimino-acetylamino]-3-[(E)-1-naphthalen-1-yl-2-oxo-pyrrolidin-3-ylidenemethyl]-8-oxo-5-thia-1-aza-bicyclo[4.2.0]oct-2-ene-2-carboxylic acid IR (KBr): 1785, 1687 cm$^{-1}$, MS (ISP): 833.2 (M+H)$^+$ 10.5. (6R,7R)-7-[(Z)-2-(2-Amino-thiazol-4-yl)-2-trityloxyimino-acetylamino]-3-[(E)-1-naphthalen-2-yl-2-oxo-pyrrolidin-3-ylidenemethyl]-8-oxo-5-thia-1-aza-bicyclo[4.2.0]oct-2-ene-2-carboxylic acid IR (KBr): 1785, 1686 cm$^{-1}$, MS (ISP): 848.2 (M–H+NH$_3$)$^+$ 10.6. (6R,7R)-7-[(Z)-2-(2-Amino-thiazol-4-yl)-2-trityloxyimino-acetylamino]-3-[(E)-1-(3-methoxy-phenyl)-2-oxo-pyrrolidin-3-ylidenemethyl]-8-oxo-5-thia-1-aza-bicyclo[4.2.0]oct-2-ene-2-carboxylic acid IR (KBr): 1784, 1684 cm$^{-1}$, MS (ISP): 828.1 (M–H+NH$_3$)$^-$ 10.7. (6R,7R)-7-[(Z)-2-(2-Amino-thiazol-4-yl)-2-trityloxyimino-acetylamino]-3-[(E)-1-(4-carboxy-phenyl)-2-oxo-pyrrolidin-3-ylidenemethyl]-8-oxo-5-thia-1-aza-bicyclo[4.2.0]oct-2-ene-2-carboxylic acid IR (KBr): 1785, 1691 cm$^{-1}$, MS (ISP): 825.2 (M–H)$^-$ 10.8. (6R,7R)-7-[(Z)-2-(2-Amino-thiazol-4-yl)-2-trityloxyimino-acetylamino]-8-oxo-3-[(E)-2-oxo-1-(3-trifluoro-phenyl)-pyrrolidin-3-ylidenemethyl]-5-thia-1-aza-bicyclo[4.2.0]oct-2-ene-2-carboxylic acid IR (KBr): 1785, 1689 cm$^{-1}$, MS (ISP): 851.2 (M+H)$^+$ 10.9. (6R,7R)-7-[(Z)-2-(2-Amino-thiazol-4-yl)-2-trityloxyimino-acetylamino]-3-[(E)-1-(3-hydroxy-phenyl)-2-oxo-pyrrolidin-3-ylidenemethyl]-8-oxo-5-thia-1-aza-bicyclo[4.2.0]oct-2-ene-2-carboxylic acid IR (KBr): 1783, 1679 cm$^{-1}$, MS (ISP): 799.2 (M+H)$^+$ 10.10. (6R,7R)-7-[(Z)-2-(2-Amino-thiazol-4-yl)-2-trityloxyimino-acetylamino]-8-oxo-3-[(E)-1-(3,4-dihydroxy-phenyl)-2-oxo-pyrrolidin-3-ylidenemethyl]-5-thia-1-aza-bicyclo[4.2.0]oct-2-ene-2-carboxylic acid IR (KBr): 1777, 1671 cm$^{-1}$, MS (ISP): 815.2 (M+H)$^+$ 10.11. (6R,7R)-7-[(Z)-2-(2-Amino-thiazol-4-yl)-2-trityloxyimino-acetylamino]-3-[(E)-1-(3-fluoro-4-hydroxy-phenyl)-2-oxo-pyrrolidin-3-ylidenemethyl]-8-oxo-5-thia-1-aza-bicyclo[4.2.0]oct-2-ene-2-carboxylic acid IR (KBr): 1782, 1678 cm$^{-1}$, MS (ISP): 817.0 (M+H)$^+$ 10.12. (6R,7R)-7-[(Z)-2-(2-Amino-thiazol-4-yl)-2-trityloxyimino-acetylamino]-3-[(E)-1-(4-methoxy-phenyl)-2-oxo-pyrrolidin-3-ylidenemethyl]-8-oxo-5-thia-1-aza-bicyclo[4.2.0]oct-2-ene-carboxylic acid IR (KBr): 1782, 1680 cm$^{-1}$, MS (ISP): 813.3 (M+H)$^+$ 10.13. (6R,7R)-7-[(Z)-2-(2-Amino-thiazol-4-yl)-2-trityloxyimino-acetylamino]-3-[(E)-1-(4-carbamoyl-phenyl)-2-oxo-pyrrolidin-3-ylidenemethyl]-8-oxo-5-thia-1-aza-bicyclo[4.2.0]oct-2-ene-2-carboxylic acid IR (KBr): 1766, 1666 cm$^{-1}$, MS (ISP): 848.2 (M+H)$^+$ 10.14. (6R,7R)-7-[(Z)-2-(2-Amino-thiazol-4-yl)-2-trityloxyimino-acetylamino]-3-[(E)-1-(3-fluoro-2-hydroxy-phenyl)-2-oxo-pyrrolidin-3-ylidenemethyl]-8-oxo-5-thia-1-aza-bicyclo[4.2.0]oct-2-ene-2-carboxylic acid $^1$H-NMR (DMSO, 250 MHz): 10 (d,1H), 9.8 (s,1H), 6.8–7.4 (m,20H), 6.6 (s,1H), 6.05 (q,1H), 5.3 (d,1H), 4.0 (b,2H), 3.8 (m,2H), 3.1–3.4 (m,2H)

10.15. (6R,7R)-7-[(Z)-2-(2-Amino-thiazol-4-yl)-2-trityloxyimino-acetylamino]-3-[(E)-1-(2-fluoro-4-hydroxy-phenyl)-2-oxo-pyrrolidin-3-ylidenemethyl]-8-oxo-5-thia-1-aza-bicyclo[4.2.0]oct-2-ene-2-carboxylic acid $^1$H-NMR (DMSO, 250 MHz): 10.1 (s,1H), 10.0 (d,1H), 7.3 (m,17H), 6.7 (m,4H), 6.1 (m,1H), 5.3 (d,1H), 4.0 (m,2H), 3.7 (m,2H), 3.0–3.3 (m,2H)

10.16. (6R,7R)-7-[(Z)-2-(2-Amino-thiazol-4-yl)-2-trityloxyimino-acetylamino]-3-[(E)-1-(2-fluoro-phenyl)-2-oxo-pyrrolidin-3-ylidenemethyl]-8-oxo-5-thia-1-aza-bicyclo[4.2.0]oct-2-ene-2-carboxylic acid $^1$H-NMR (DMSO, 250 MHz): 14.0 (b,1H), 10.0 (d,1H), 7.9 (s,1H), 7.4–8.0 (m,3H), 7.2–7.4 (m,17H), 6.6 (s,1H), 6.0 (dd,1H), 5.3 (d,1H), 4.0 (sb,2H), 3.8 (m,2H), 3.1–3.4 (m,2H)

10.17. Mixture of (6R,7R)-7-[(Z)-2-(2-amino-thiazol-4-yl)-2-trityloxyimino-acetylamino]-3-[(E)-1-[(R)- and -[(S)-carboxy-phenyl-methyl]-2-oxo-pyrrolidin-3-ylidenemethyl]-8-oxo-5-thia-1-aza-bicyclo[4.2.0]oct-2-ene-2-carboxylic acid IR (KBr): 1780, 1675, 1630 cm$^{-1}$, MS (ISP): 841.3 (M+H)$^+$ 10.18. (6R,7R)-3-[(E)-1-(4-Allyloxycarbonylamino-benzyl)-2-oxo-pyrrolidin-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid IR (KBr): 1781, 1725, 1678 cm$^{-1}$, MS (ISP): 911.9 (M+NH$_3$—H)$^-$ 10.19. (6R,7R)-3-[(E)-1-(4-Amino-benzyl)-2-oxo-pyrrolidin-3-ylidenemethyl]-7-[(Z)-2-(2-amino-thiazol-4-yl)-2-trityloxyimino-acetylamino]-8-oxo-5-thia-1-aza-bicyclo-[4.2.0]oct-2-ene-2-carboxylic acid IR (KBr): 3428, 1778, 1669 cm$^{-1}$, MS (ISP): 812.2 (M+H)$^+$ 10.20. (6R,7R)-7-[(Z)-2-(2-Amino-thiazol-4-yl)-2-trityloxyimino-acetylamino]-3-[(E)-1-(2-fluoro-benzyl)-2-oxo-pyrrolidin-3-ylidenemethyl]-8-oxo-5-thia-1-aza-bicyclo[4.2.0]oct-2-ene-2-carboxylic acid IR (KBr): 1782, 1680 cm$^{-1}$, MS (ISP): 815.2 (M+H)$^+$ 10.21. (6R,7R)-7-[(Z)-2-(2-Amino-thiazol-4-yl)-2-trityloxyimino-acetylamino]-3-[(E)-1-(2-methoxy-benzyl)-2-oxo-pyrrolidin-3-ylidenemethyl]-8-oxo-5-thia-1-aza-bicyclo[4.2.0]oct-2-ene-2-carboxylic acid IR (KBr): 1782, 1678, 1626 cm$^{-1}$, MS (ISP): 827.3 (M+H)$^+$ 10.22. (6R,7R)-7-[(Z)-2-(2-Amino-thiazol-4-yl)-2-trityloxyimino-acetylamino]-3-[(E)-1-(3-hydroxy-benzyl)-2-oxo-pyrrolidin-3-ylidenemethyl]-8-oxo-5-thia-1-aza-bicyclo[4.2.0]oct-2-ene-2-carboxylic acid IR (KBr): 1780, 1670, 1625 cm$^{-1}$, MS (ISN): 811.5 (M–H)$^-$ 10.23. (6R,7R)-7-[(Z)-2-(2-Amino-thiazol-4-yl)-2-trityloxyimino-acetylamino]-3-[(E)-1-(3-fluoro-benzyl)-2-oxo-pyrrolidin-3-ylidenemethyl]-8-oxo-5-thia-1-aza-bicyclo[4.2.0]oct-2-ene-2-carboxylic acid IR (KBr): 1784, 1683, 1619 cm$^{-1}$ 10.24. (6R,7R)-7-[(Z)-2-(2-Amino-thiazol-4-yl)-2-trityloxyimino-acetylamino]-3-[(E)-1-(3-methoxy-benzyl)-2-oxo-pyrrolidin-3-ylidenemethyl]-8-oxo-5-thia-1-aza-bicyclo[4.2.0]oct-2-ene-2-carboxylic acid IR (KBr): 1785, 1682, 1612 cm$^{-1}$, MS (ISP): 827.2 (M+H)$^+$ 10.25. (6R,7R)-7-[(Z)-2-(2-Amino-thiazol-4-yl)-2-trityloxyimino-acetylamino]-3-[(E)-1-[4-(3-carboxy-propionylamino)-benzyl]-2-oxo-pyrrolidin-3-ylidenemethyl]-8-oxo-5-thia-1-aza-bicyclo[4.2.0]oct-2-ene-2-carboxylic acid IR (KBr): 1784, 1666 cm$^{-1}$, MS (ISP): 693.0 (M+Na$^+$—(C$_6$H$_5$)$_3$C)

10.26. (6R,7R)-7-[(Z)-2-(2-Amino-thiazol-4-yl)-2-trityloxyimino-acetylamino]-3-[(E)-1-(4-carboxy-benzyl)-2-oxo-pyrrolidin-3-ylidenemethyl]-8-oxo-5-thia-1-aza-bicyclo[4.2.0]oct-2-ene-2-carboxylic acid IR (KBr): 1786, 1685, 1620 cm$^{-1}$, MS (ISP): 841.4 (M+H)$^+$ 10.27. (6R,7R)-7-[(Z)-2-(2-Amino-thiazol-4-yl)-2-trityloxyimino-acetylamino]-3-[(E)-1-(4-nitro-benzyl)-2-oxo-pyrrolidin-3-ylidenemethyl]-8-oxo-5-thia-1-aza-bicyclo[4.2.0]oct-2-ene-2-carboxylic acid IR (KBr): 1785, 1684, 1521 cm$^{-1}$, MS (ISP): 842.3 (M+H)$^+$ 10.28. (6R,7R)-7-[(Z)-2-(2-Amino-thiazol-4-yl)-2-trityloxyimino-acetylamino]-3-[(E)-1-(4-methoxy-benzyl)-2-oxo-pyrrolidin-3-ylidenemethyl]-8-oxo-5-thia-1-aza-bicyclo[4.2.0]oct-2-ene-2-carboxylic acid IR (KBr): 1782, 1679, 1618 cm$^{-1}$, MS (ISP): 827.3 (M+H)$^+$ 10.29. (6R,7R)-7-[(Z)-2-(2-Amino-thiazol-4-yl)-2-trityloxyimino-acetylamino]-3-[(E)-1-(4-fluoro-benzyl)-2-oxo-pyrrolidin-3-ylidenemethyl]-8-oxo-5-thia-1-aza-bicyclo[4.2.0]oct-2-ene-2-carboxylic acid IR (KBr): 1780, 1675, 1627 cm$^{-1}$, MS (ISP): 815.3 (M+H)$^+$ 10.30. (6R,7R)-7-[(Z)-2-(2-Amino-thiazol-4-yl)-2-trityloxyimino-acetylamino]-8-oxo-3-[(E)-2-oxo-1-(4-trifluoromethyl-benzyl)-pyrrolidin-3-ylidenemethyl]-5-thia-1-aza-bicyclo[4.2.0]oct-2-ene-2-carboxylic acid IR (KBr): 1786, 1683, 1620 cm$^{-1}$, MS (ISP): 865.2 (M+H)$^+$ 10.31. (6R,7R)-7-[(Z)-2-(2-Amino-thiazol-4-yl)-2-trityloxyimino-acetylamino]-3-[(E)-1-benzyl-2-oxo-pyrroldin-3-ylidenemethyl]-8-oxo-5-thia-1-aza-bicyclo[4.2.0]oct-2-ene-2-carboxylic acid IR (KBr): 1784, 1682, 1625 cm$^{-1}$, MS (ISP): 797.2 (M+H)$^+$ 10.32. (6R,7R)-7-[(Z)-2-(2-Amino-thiazol-4-yl)-2-trityloxyimino-acetylamino]-8-oxo-3-[(E)-2-oxo-1-(1,3,4-thiadiazol-2-yl)-pyrrolidin-3-ylidenemethyl]-5-thia-1-aza-bicyclo[4.2.0]oct-2-ene-2-carboxylic acid trifluoroacetate IR(KBr): 1783, 1662 cm$^{-1}$, MS(ISP): 791.0 (M+H)$^+$ 10.33. 1:1 Mixture of (6R,7R)-7-[(Z)-2-(2-Amino-thiazol-4-yl)-2-trityloxyimino-acetylamino]-8-oxo-3-[(E)-2-oxo-1-[(R)- and -[(S)-2-oxo-tetrahydro-furan-3-yl]-pyrrolidin-3-ylidenemethyl]-5-thia-1-aza-bicyclo[4.2.0]oct-2-ene-2-carboxylic acid trifluoroacetate IR(KBr): 1780, 1681, 1627 cm$^{-1}$, MS(ISP): 791.1 (M+H)$^+$ 10.34. (6R,7R)-7-[(Z)-2-(2-Amino-thiazol-4-yl)-2-trityloxyimino-acetylamino]-3-[(E)-1-(2-chloro-pyridin-3-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1783, 1689, 1623 cm$^{-1}$, MS(ISP): 818.3(M+H)$^+$ 10.35. (6R,7R)-7-[(Z)-2-(2-Amino-thiazol-4-yl)-2-trityloxyimino-acetylamino]-3-[(E)-1-(6-chloro-pyridazin-3-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1786, 1695, 1621 cm$^{-1}$, MS(ISP): 819.1 (M+H)$^+$ 10.36. (6R,7R)-7-[(Z)-2-(2-Amino-thiazol-4-yl)-2-trityloxyimino-acetylamino]-8-oxo-3-[(E)-2-oxo-1-pyrimidin-2-yl-pyrrolidin-3-ylidenemethyl]-5-thia-1-aza-bicyclo[4.2.0]oct-2-ene-2-carboxylic acid trifluoroacetate IR(KBr): 1785, 1693, 1668, 1625 cm$^{-1}$, 10.37. (6R,7R)-7-[(Z)-2-(2-Amino-thiazol-4-yl)-2-trityloxyimino-acetylamino]-3-[(E)-1-(3,5-dimethylpyrazin-2-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1784, 1687, 1624 cm$^{-1}$, MS(ISP): 813.2 (M+H)$^+$ 10.38. (6R,7R)-3-[(E)-(1-Allyloxycarbonyl-piperidin-4-yl)-2-oxo-pyrrolidin-3-ylidenemethyl]-7-[(Z)-2-(2-amino-thiazol-4-yl)-2-trityloxyimino-acetylamino]-8-oxo-5-thia-1-aza-bicyclo[4.2.0]oct-2-ene-2-carboxylic acid IR(KBr): 1786, 1686, 1625 cm$^{-1}$, MS(ISP): 874.5 (M+H)$^+$ 10.39. (6R,7R)-7-[(Z)-2-(2-Amino-thiazol-4-yl)-2-trityloxyimino-acetylamino]-8-oxo-3-[(E)-2-oxo-1-piperidin-4-yl-pyrrolidin-3-ylidenemethyl]-5-thia-1-aza-bicyclo[4.2.0]oct-2-ene-2-carboxylic acid hydrochloride IR(KBr): 1781, 1659, 1630 cm$^{-1}$, MS(ISP): 790.4 (M+H)$^+$ 10.40. (6R,7R)-7-[(Z)-2-(2-Amino-thiazol-4-yl)-2-trityloxyimino-acetylamino]-3-[(E)-1-[1-(3-carboxy-propionyl)-piperidin-4-yl]-2-oxo-pyrrolidin-3-ylidenemethyl]-8-oxo-5-thia-1-aza-bicyclo[4.2.0]oct-2-ene-2-carboxylic acid trifluoroacetate IR(KBr): 1784, 1726, 1680, 1630, 1530 cm$^{-1}$, MS(ISP): 890.5 (M+H)$^+$ IR(KBr): 1775, 1674, 1631 cm$^{-1}$, MS(ISP): 789.3 (M+H)$^+$ 10.44. (6R,7R)-7-[(Z)-2-(2-Amino-thiazol-4-yl)-2-trityloxyimino-acetylamino]-8-oxo-3-[(E)-2-oxo-thiophen-2-ylidenemethyl-pyrrolidin-3-ylidenemethyl]-5-thia-1-aza-bicyclo[4.2.0]oct-2-ene-2-carboxylic acid IR(KBr): 1784, 1681, 1625, 1447 cm$^{-1}$, MS(ISP): 803.2 (M+H)$^+$ 10.45. (6R,7R)-7-[(Z)-2-(2-Amino-thiazol-4-yl)-2-trityloxyimino-acetylamino]-3-[(E)-1-(3-ethoxycarbonyl-thiophen-2-yl)-2-oxo-pyrroldin-3-ylidenemethyl]-8-oxo-5-thia-1-aza-bicyclo[4.2.0]oct-2-ene-2-carboxylic acid IR(KBr): 1786, 1704, cm$^{-1}$ 11. Removal of the protecting group (Scheme 1 (8)→(9))

11.1. Removal of the protecting group 11.1.1. Preparation of (6R,7R)-7-[(Z)-2-(2-Amino-thiazol-4-yl)-2-hydroxyimino-acetylamino]-3-[(E)-1-(4-hydroxy-phenyl)-2-oxo-pyrrolidin-3-ylidenemethyl]-8-oxo-5-thia-1-aza-bicyclo[4.2.0]oct-2-ene-2-carboxylic acid

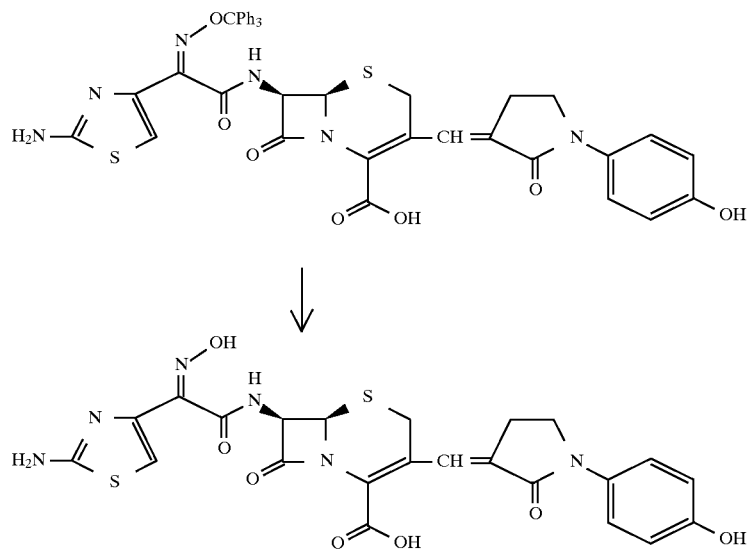

10.41. (6R,7R)-7-[(Z)-2-(2-Amino-thiazol-4-yl)-2-trityloxyimino-acetylamino]-3-[(E)-1-(1-ethoxycarbonyl-piperidin-4-yl)-2-oxo-pyrrolidin-3-ylidenemethyl]-8-oxo-5-thia-1-aza-bicyclo[4.2.0]oct-2-ene-carboxylic acid trifluoroacetate IR(KBr): 1784, 1677 cm$^{-1}$, MS(ISP): 862.5 (M+H)$^+$ 10.42. 1:1 Mixture of (6R,7R)-7-[(Z)-2-(2-Amino-thiazol-4-yl)-2-trityloxyimino-acetylamino]-8-oxo-3-[(E)-2-oxo-1-[(R)- and -[(S)-tetrahydrofuran-2-ylmethyl]-pyrrolidin-3-ylidenemethyl]-5-thia-1-aza-bicyclo[4.2.0]oct-2-ene-2-carboxylic acid IR(KBr): 1784, 1681, 1626 cm$^{-1}$, MS(ISP): 791.2 (M+H)$^+$ 10.43. (6R,7R)-7-[(Z)-2-(2-Amino-thiazol-4-yl)-2-trityloxyimino-acetylamino]-8-oxo-3-[(E)-2-oxo-1-(1H-tetrazol-5-ylmethyl)-pyrrolidin-3-ylidenemethyl]-5-thia-1-aza-bicyclo[4.2.0]oct-2-ene-2-carboxylic acid To 10 ml ice-cold trifluoroacidic acid was added portionwise 1.1 g (1.38 mmol) (6,R,7R)-7-[(Z)-2-(2-amino-thiazol-4-yl)-2-trityloxyimino-acetylamino]-3-[(E)-1-(4-hydroxy-phenyl)-2-oxo-pyrrolidin-3-ylidenemethyl]-8-oxo-5-thia-1-aza-bicyclo[4.2.0]oct-2-ene-2-carboxylic acid, the temperature being kept below 5° C. After 20 min, 0.4 ml triethylsilane was added dropwise resulting in a beige suspension which was poured on 100 ml diethylether. This mixture was stirred for 30 min and the solid was collected by filtration and crystallized from 15 ml 90% acetone.

yield: 552.5 mg yellow crystals (72%)

IR(KBr): 1774, 1667 cm$^{-1}$, MS(ISP): 557.4 (M+H)$^+$ 11.1.2. (6R,7R)-7-[(Z)-2-Amino-thiazol-4-yl)-2-hydroxyimino-acetylamino]-3-[(E)-1-(1H-benzimidazol-2-ylmethyl)-2-oxo-pyrrolidin-3-ylidenemethyl]-8-oxo-5-thia-1-aza-bicylco[4.2.0]oct-2-ene-2-carboxylic acid trifluoroacetate

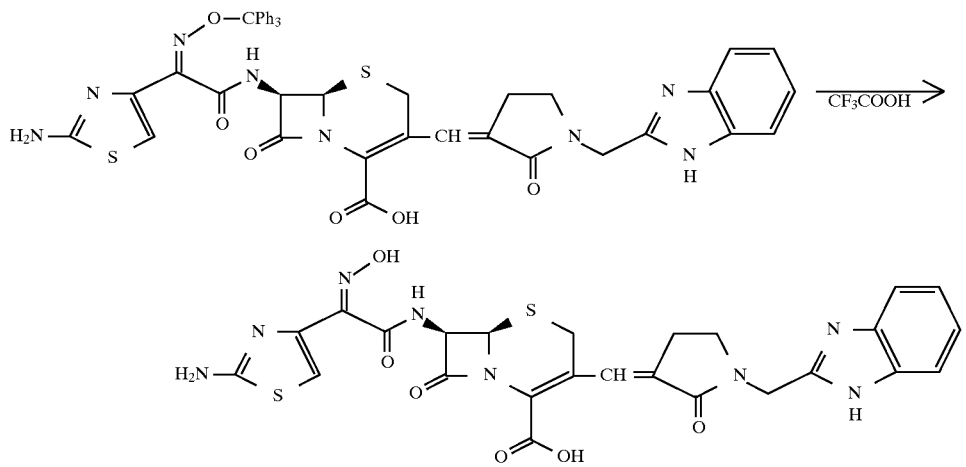

To 4 ml ice-cold trifluoroacetic acid was added portionwise 530 mg (0.63 mmol) (6R,7R)-7-[(Z)-2-amino-thiazol-4-yl)-2-trityloxyimino-acetylamino]-3-[(E)-1-(1H-benzimidazol-2-ylmethyl)-2-oxo-pyrrolidin-3-ylidenemethyl]-8-oxo-5-thia-1-aza-bicylco[4.2.0]oct-2-ene-2-carboxylic acid, the temperature being kept below 5° C. Triethylsilane (0.23 ml, 1.45 mmol) was added dropwise resulting in a beige suspension which was poured on 100 ml diethylether after 2.5 h. This mixture was stirred for 1.5 h and the solid was collected by filtration. It was resuspended in 10 ml ethyl acetate and stirred for 1 h, collected by filtration and dried. yield: 400 mg beige powder IR(KBr): 1774, 1675, 1630 cm$^{-1}$, MS(ISP): 595.2 (M+H)$^+$ According to the procedure set forth in the preceding examples, the following additional compounds were prepared:

11.1.3. (6R,7R)-7-[(Z)-2-(2-Amino-thiazol-4-yl)-2-hydroxyimino-acetylamino]-3-[(E)-1-(3-nitro-phenyl)-2-oxo-pyrrolidin-3-ylidenemethyl]-8-oxo-5-thia-1-aza-bicyclo[4.2.0]oct-2-ene-2-carboxylic acid IR (KBr): 1779, 1679 cm$^{-1}$, MS (ISP): 586.4 (M+H)$^+$ 11.1.4. (6R,7R)-7-[(Z)-2-(2-Amino-thiazol-4-yl)-2-hydroxyimino-acetylamino]-3-[(E)-1-naphthalen-1-yl-2-oxo-pyrrolidin-3-ylidenemethyl]-8-oxo-5-thia-1-aza-bicyclo[4.2.0]oct-2-ene-2-carboxylic acid trifluoroacetate IR (KBr): 1781, 1675, 1633 cm$^{-1}$, MS (ISP): 591.3 (M+H)$^+$ 11.1.5. (6R,7R)-7-[(Z)-2-(2-Amino-thiazol-4-yl)-2-hydroxyimino-acetylamino]-8-oxo-3-[(E)-2-oxo-1-naphthalen-2-yl-pyrrolidin-3-ylidenemethyl]-5-thia-1-aza-bicyclo[4.2.0]oct-2-ene-2-carboxylic acid trifluoroacetate IR (KBr): 1779, 1677, 1630 cm$^{-1}$, MS (ISP): 591.2 (M+H)$^+$ 11.1.6. (6R,7R)-7-[(Z)-2-(2-Amino-thiazol-4-yl)-2-hydroxyimino-acetylamino]-3-[(E)-1-(3-methoxy-phenyl)-2-oxo-pyrrolidin-3-ylidenemethyl]-8-oxo-5-thia-1-aza-bicyclo[4.2.0]oct-2-ene-2-carboxylic acid IR (KBr): 1778, 1675 cm$^{-1}$, MS (ISP): 639.3 (M+H)$^+$ 11.1.7. (6R,7R)-7-[(Z)-2-(2-Amino-thiazol-4-yl)-2-hydroxyimino-acetylamino]-3-[(E)-1-(4-carboxy-phenyl)-2-oxo-pyrrolidin-3-ylidenemethyl]-8-oxo-5-thia-1-aza-bicyclo[4.2.0]oct-2-ene-2-carboxylic acid IR (KBr): 1775, 1686 cm$^{-1}$, MS (ISP): 585.3 (M+H)$^+$ 11.1.8. (6R,7R)-7-[(Z)-2-(2-Amino-thiazol-4-yl)-2-hydroxyimino-acetylamino]-3-[(E)-1-(3-fluoro-phenyl)-2-oxo-pyrrolidin-3-ylidene]-8-oxo-5-thia-1-aza-bicyclo[4.2.0]oct-2-ene-2-carboxylic acid trifluoroacetate IR (KBr): 1775, 1674 cm$^{-1}$, MS (ISP): 559.2 (M+H)$^+$ 11.1.9. (6R,7R)-7-[(Z)-2-(2-Amino-thiazol-4-yl)-2-hydroxyimino-acetylamino]-8-oxo-3-{(E)-2-oxo-1-(3-trifluoromethyl-phenyl)-pyrrolidin-3-ylidenemethyl]-5-thia-1-aza-bicyclo[4.2.0]oct-2-ene-2-carboxylic acid trifluoroacetate IR (KBr): 1775, 1675, 1631 cm$^{-1}$, MS (ISP): 609.0 (M+H)$^+$ 11.1.10. (6R,7R)-7-[(Z)-2-(2-Amino-thiazol-4-yl)-2-hydroxyimino-acetylamino]-3-[(E)-1-(3-hydroxy-phenyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1770, 1765 cm$^{-1}$, MS (ISP): 557.2 (M+H)$^+$ 11.1.11. (6R,7R)-7-[(Z)-2-(2-Amino-thiazol-4-yl)-2-hydroxyimino-acetylamino]-8-oxo-3-[(E)-1-(3,4-dihydroxy-phenyl)-2-oxo-pyrrolidin-3-ylidenemethyl]-5-thia-1-aza-bicyclo[4.2.0]oct-2-ene-2-carboxylic acid IR (KBr): 1776, 1654 cm$^{-1}$, MS (ISP): 573.0 (M+H)$^+$ 11.1.12. (6R,7R)-7-[(Z)-2-(2-Amino-thiazol-4-yl)-2-hydroxyimino-acetylamino]-3-[(E)-1-(3-fluoro-4-hydroxy-phenyl)-2-oxo-pyrrolidin-3-ylidenemethyl]-8-oxo-5-thia-1-aza-bicyclo[4.2.0]oct-2-ene-2-carboxylic acid IR (KBr): 1774, 1669 cm$^{-1}$, MS (ISP): 575.2 (M+H)$^+$ 11.1.13. (6R,7R)-7-[(Z)-2-(2-Amino-thiazol-4-yl)-2-hydroxyimino-acetylamino]-3-[(E)-1-(2-methoxy-phenyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1778, 1674 cm$^{-1}$, MS (ISP): 571.2 (M+H)$^+$ 11.1.14. (6R,7R)-7-[(Z)-2-(2-Amino-thiazol-4-yl)-2-hydroxyimino-acetylamino]-3-[(E)-1-(2-fluoro-4-hydroxy-phenyl)-2-oxo-pyrrolidin-3-ylidenemethyl]-8-oxo-5-thia-1-aza-bicyclo[4.2.0]oct-2-ene-2-carboxylic acid IR (KBr): 1777, 1673 cm$^{-1}$, MS (ISP): 575.1 (M+H)$^+$ 11.1.15. (6R,7R)-7-[(Z)-2-(2-Amino-thiazol-4-yl)-2-hydroxyimino-acetylamino]-3-[(E)-1-(2-fluoro-phenyl)-2-oxo-pyrrolidin-3-ylidenemethyl]-8-oxo-5-thia-1-aza-bicyclo[4.2.0]oct-2-ene-2-carboxylic acid $^1$H-NMR (DMSO, 250 MHz): 11.8 (sb,1H), 9.7 (d,1H), 8.0 (b,1H), 7.1–7.6 (m,7H), 5.9 (dd,1H), 5.2 (d,1H), 4.0 (sb,2H), 3.8 (m,2H), 3.0–3.4 (m,2H)

11.1.16. Mixture of (6R,7R)-7-[(Z)-2-(2-amino-thiazol-4-yl)-2-hydroxyimino-acetylamino]-3-[(E)-1-[(R) and -(S)-carboxy-phenyl-methyl]-2-oxo-pyrrolidin-3-ylidenemethyl]-8-oxo-5-thia-1-aza-bicyclo[4.2.0]oct-2-ene-2-carboxylic acid trifluoroacetate IR (KBr): 1778, 1671, 1632 cm$^{-1}$, MS (ISP): 614.0 [(M+NH$_3$)—H]$^-$ 11.1.17. (6R,7R)-7-[(Z)-2-(2-Amino-thiazol-4-yl)-2-hydroxyimino-acetylamino]-3-[(E)-1-(2-fluoro-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1777, 1672, 1634 cm$^{-1}$, MS (ISP): 573.2 (M+H)$^+$ 11.1.18. (6R,7R)-7-[(Z)-2-(2-Amino-thiazol-4-yl)-2-hydroxyimino-acetylamino]-3-[(E)-1-(2-methoxy-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1784, 1674, 1634 cm$^{-1}$, MS (ISP): 585.3 (M+H)$^+$ 11.1.19. (6R,7R)-7-[(Z)-2-(2-Amino-thiazol-4-yl)-2-hydroxyimino-acetylamino]-3-[(E)-1-(3-hydroxy-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1777, 1671, 1631 cm$^{-1}$, MS (ISN): 586.2 ((M+NH$_3$)—H)$^-$ 11.1.20. (6R,7R)-7-[(Z)-2-(2-Amino-thiazol-4-yl)-2-hydroxyimino-acetylamino]-3-[(E)-1-(3-fluoro-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1779, 1675, 1632 cm$^{-1}$, MS (ISP): 596.1 (M+Na)$^+$ 11.1.21. (6R,7R)-7-[(Z)-2-(2-Amino-thiazol-4-yl)-2-hydroxyimino-acetylamino]-3-[(E)-1-(3-methoxy-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1780, 1675, 1632 cm$^{-1}$, MS (ISP): 585.3 (M+H)$^+$ 11.1.22. (6R,7R)-7-[(Z)-2-(2-Amino-thiazol-4-yl)-2-hydroxyimino-acetylamino]-3-[(E)-1-(4-carboxy-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1775, 1698, 1665, 1642 cm$^{-1}$, MS (ISP): 599.2 (M+H)$^+$ 11.1.23. (6R,7R)-7-[(Z)-2-(2-Amino-thiazol-4-yl)-2-hydroxyimino-acetylamino]-3-[(E)-1-(4-nitro-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1782, 1673, 1635 cm$^{-1}$, MS (ISP): 600.3 (M+H)$^+$ 11.1.24. (6R,7R)-7-[(Z)-2-(2-Amino-thiazol-4-yl)-hydroxyimino-acetylamino]-3-[(E)-1-(4-methoxy-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1781, 1673, 1634 cm$^{-1}$, MS (ISP): 585.3 (M+H)$^+$ 11.1.25. (6R,7R)-7-[(Z)-2-(2-Amino-thiazol-4-yl)-2-hydroxyimino-acetylamino]-3-[(E)-1-(4-fluoro-benzyl)-2-oxo-pyrrolidin-3-ylidenemethyl]-8-oxo-5-thia-1-aza-bicyclo[4.2.0]oct-2-ene-2-carboxylic acid trifluoroacetate IR (KBr): 1778, 1671, 1634 cm$^{-1}$, MS (ISP): 573.3 (M+H)$^+$ 11.1.26. (6R,7R)-7-[(Z)-2-(2-Amino-thiazol-4-yl)-2-hydroxyimino-acetylamino]-8-oxo-3-[(E)-2-oxo-1-(4-trifluoromethyl-benzyl)-pyrrolidin-3-ylidenemethyl]-5-thia-1-aza-bicyclo[4.2.0]oct-2-ene-2-carboxylic acid trifluoroacetate IR (KBr): 1780, 1675, 1633 cm$^{-1}$, MS (ISP): 623.2 (M+H)$^+$ 11.1.27. (6R,7R)-7-[(Z)-2-(2-Amino-thiazol-4-yl)-2-hydroxyimino-acetylamino]-3-[(E)-1-benzyl-2-oxo-pyrrolidin-3-ylidenemethyl]-8-oxo-5-thia-1-aza-bicyclo[4.2.0]oct-2-ene-2-carboxylic acid IR (KBr): 1779, 1671, 1634 cm$^{-1}$, MS (ISP): 555.3 (M+H)$^+$ 11.1.28. (6R,7R)-7-[(Z)-2-(2-Amino-thiazol-4-yl)-2-hydroxyimino-acetylamino]-8-oxo-3-[(E)-2-oxo-1-(1,3,4-thiadiazol-2-yl)-pyrrolidin-3-ylidenemethyl]-5-thia-1-aza-bicyclo[4.2.0]oct-2-ene-2-carboxylic acid trifluoroacetate IR(KBr): 1777, 1680, 1627 cm$^{-1}$, MS(ISP): 549.0 (M+H)$^+$ 11.1.29. 1:1 Mixture of (6R,7R)-7-[(Z)-2-(2-Amino-thiazol-4-yl)-2-hydroxyimino-acetylamino]-8-oxo-3-[(E)-2-oxo-1-[(R)- and -[(S)-2-oxo-tetrahydro-furan-3-yl]-pyrrolidin-3-ylidenemethyl]-5-thia-1-aza-bicyclo[4.2.0]oct-2-ene-2-carboxylic acid trifluoroacetate IR(KBr): 1774, 1674, 1633 cm$^{-1}$, MS(ISP): 549.2 (M+H)$^+$ 11.1.30. (6R,7R)-7-[(Z)-2-(2-Amino-thiazol-4-yl)-hydroxyimino-acetylamino]-3-[(E)-1-(2-chloro-pyridin-3-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1781, 1677, 1634 cm$^{-1}$, MS(ISP): 576.2 (M+H)$^+$ 11.1.31. (6R,7R)-7-[(Z)-2-(2-Amino-thiazol-4-yl)-2-hydroxyimino-acetylamino]-8-oxo-3-[(E)-2-oxo-1-pyrimidin-2-yl-pyrrolidin-3-ylidenemethyl]-5-thia-1-aza-bicyclo[4.2.0]oct-2-ene-2-carboxylic acid trifluoroacetate IR(KBr): 1779, 1667, 1629 cm$^{-1}$, MS(ISP): 543.2 (M+H)$^+$ 11.1.32. (6R,7R)-7-[(Z)-2-(2-Amino-thiazol-4-yl)-2-hydroxyimino-acetylamino]-3-[(E)-1-(3,5-dimethyl-pyrazin-2-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1779, 1676, 1633 cm$^{-1}$, MS(ISP): 571.3 (M+H)$^+$ 11.1.33. (6R,7R)-3-[(E)-(1-Allyloxycarbonyl-piperidin-4-yl)-2-oxo-pyrrolidin-3-ylidenemethyl]-7-[(Z)-2-(2-amino-thiazol-4-yl)-2-hydroxyimino-acetylamino]-8-oxo-5-thia-1-aza-bicyclo[4.2.0]oct-2-ene-2-carboxylic acid trifluoroacetate IR(KBr): 1782, 1677, 1530 cm$^{-1}$, MS(ISP): 632.4 (M+H)$^+$ 11.1.34. (6R,7R)-7-[(Z)-2-(2-Amino-thiazol-4-yl)-2-hydroxyimino-acetylamino]-8-oxo-3-[(E)-2-oxo-1-piperidin-4-yl-pyrrolidin-3-ylidenemethyl]-5-thia-1-aza-bicyclo[4.2.0]oct-2-ene-2-carboxylic acid hydrochloride IR(KBr): 1774, 1631 cm$^{-1}$, MS(ISP): 548.2 (M+H)$^+$ 11.1.35. (6R,7R)-7-[(Z)-2-(2-Amino-thiazol-4-yl)-2-hydroxyimino-acetylamino]-3-[(E)-1-(1-ethoxycarbonyl-piperidin-4-yl)-2-oxo-pyrrolidin-3-ylidenemethyl]-8-oxo-5-thia-1-aza-bicyclo[4.2.0]oct-2-ene-carboxylic acid trifluoroacetate IR(KBr): 1778, 1675, 1630 cm$^{-1}$, MS(ISP): 620.4 (M+H)$^+$ 11.1.36. (6R,7R)-7-[(Z)-2-(2-Amino-thiazol-4-yl)-2-hydroxyimino-acetylamino]-3-[(E)-1-[1-(3-carboxy-propionyl)-piperidin-4-yl]-2-oxo-pyrrolidin-3-ylidenemethyl]-8-oxo-5-thia-1-aza-bicyclo[4.2.0]oct-2-ene-2-carboxylic acid trifluoroacetate IR(KBr): 1779, 1672, 1632 cm$^{-1}$, MS(ISN): 663.2 (M+NH$_3$—H)$^-$ 11.1.37. 1:1 Mixture of (6R,7R)-7-[(Z)-2-(2-amino-thiazol-4-yl)-2-hydroxyimino-acetylamino]-8-oxo-3-[(E)-2-oxo-1-[(R)- and -[(S)-tetrahydro-furan-2-ylmethyl]-pyrrolidin-3-ylidenemethyl]-5-thia-1-aza-bicyclo [4.2.0]oct-2-ene-2-carboxylic acid trifluoroacetate IR(KBr): 1780, 1669 cm$^{-1}$, MS(ISP): 549.2 (M+H)$^+$ 11.1.38. (6R,7R)-7-[(Z)-2-(2-Amino-thiazol-4-yl)-2-hydroxyimino-acetylamino]-8-oxo-3-[(E)-2-oxo-1-(1H-tetrazol-5-ylmethyl)-pyrrolidin-3-ylidenemethyl]-5-thia-1-aza-bicyclo[4.2.0]oct-2-ene-2-carboxylic acid IR(KBr): 1769, 1674, 1633 cm$^{-1}$, MS(ISP): 547.0 (M+H)$^+$ 11.1.39. (6R,7R)-7-[(Z)-2-(2-Amino-thiazol-4-yl)-2-hydroxyimino-acetylamino]-8-oxo-3-[(E)-2-oxo-thiophen-2-ylidenemethyl-pyrrolidin-3-ylidenemethyl]-5-thia-1-aza-bicyclo[4.2.0]oct-2-ene-2-carboxylic acid trifluoroacetate IR(KBr): 1776, 1671, 1632 cm$^{-1}$, MS(ISP): 561.2 (M+H)$^+$ 11.1.40. (6R,7R)-7-[(Z)-2-(2-Amino-thiazol-4-yl)-2-hydroxyimino-acetylamino]-3-[(E)-1-(3-ethoxycarbonyl-thiophen-2-yl)-2-oxo-pyrrolidin-3-ylidenemethyl]-8-oxo-5-thia-1-aza-bicyclo[4.2.0]oct-2-ene-2-carboxylic acid trifluoroacetate IR(KBr): 1783, 1680 cm$^{-1}$, MS(ISP): 619.4 (M+H)$^+$ 11.1.41. (6R,7R)-7-[(Z)-2-(2-Amino-thiazol-4-yl)-2-hydroxyimino-acetylamino]-3-[(E)-1-(3-carbamoyl-thiophen-2-yl)-2-oxo-pyrrolidin-3-ylidenemethyl]-8-oxo-5-thia-1-aza-bicyclo[4.2.0]oct-2-ene-2-carboxylic acid IR(KBr): 1774, 1667 cm$^{-1}$, MS(ISP): 590.2 (M+H)$^+$ 11.2. Preparation of the sodium salt 11.2.1. Preparation of (6R,7R)-7-[(Z)-2-(2-Amino-thiazol-4-yl)-2-hydroxyimino-acetylamino]-3-[(E)-1-(4-carbamoyl-phenyl)-2-oxo-pyrrolidin-3-ylidenemethyl]-8-oxo-5-thia-1-aza-bicyclo[4.2.0]oct-2-ene-2-carboxylic acid Na salt 8-oxo-5-thia-1-aza-bicylco[4.2.0]oct-2-ene-2-carboxylic acid sodium salt The trityl group of 2.43 (2.6 mmol) (6,R,7R)-7-[(Z)-2-(2-amino-thiazol-4-yl)-2-trityloxyimino-acetylamino]-3-[(E)-1-(6-chloro-pyridizan-3-yl)-2-oxo-pyrrolidin-3-ylidenemethyl]-8-oxo-5-thia-1-aza-bicyclo[4.2.0]oct-2-ene-2-carboxylic acid was removed according to the procedure used above. The product was then converted at room temperature into the sodium salt by suspending the raw material (1.9 g) in 240 ml water and adjusting the pH to 6.5 with 1N NaOH. The dark-brown solution was purified by reversed phase chromatography (RP-18 LiChroPrep gel, water:acetonitril=98:2).

yield: 571 mg (32%)

IR(KBr): 1765, 1673, 1616 cm$^{-1}$, MS(ISP): 577.1 (M+H)$^+$

According to the procedure set forth in the preceding examples, the following additional compounds were prepared:

11.2.3. (6R,7R)-7-[(Z)-2-(2-Amino-thiazol-4-yl)-2-hydroxyimino-acetylamino]-3-[(E)-1-[4-(3-carboxy-propionylamino)-benzyl]-2-oxo-pyrrolidin-3-ylidenemethyl]- 8-oxo-5-thia-1-aza-bicyclo[4.2.0]oct-2-ene-2-carboxylic acid disodium salt

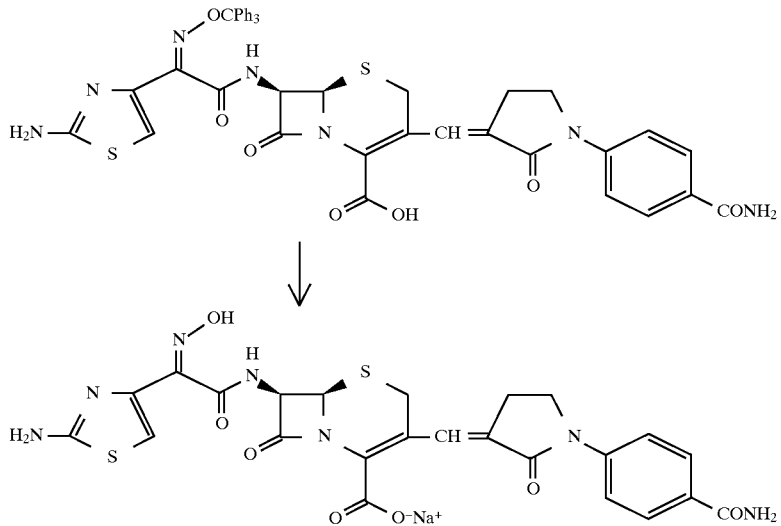

The trityl group of 1.2 g (1.45 mmol) (6,R,7R)-7-[(Z)-2-(2-amino-thiazol-4-yl)-2-trityloxyimino-acetylamino]-3-[(E)-1-(4-carbamoyl-phenyl)-2-oxo-pyrrolidin-3-ylidenemethyl]-8-oxo-5-thia-1-aza-bicyclo[4.2.0]oct-2-ene-2-carboxylic acid was removed according to the procedure used above. However, the product was converted into the sodium salt. 910 mg mmol of raw (6,R,7R)-7-[(Z)-2-(2-amino-thiazol-4-yl)-2-hydroxyimino-acetylamino]-3-[(E)-1-(4-carbamoyl-phenyl)-2-oxo-pyrrolidin-3-ylidenemethyl]-8-oxo-5-thia-1-aza-bicyclo[4.2.0]oct-2-ene-2-carboxylic acid trifluoracetic acid salt was suspended in 9 ml water and 1 ml acetonitrile. At 0° C. the pH was adjusted to 7 using 1N NaOH. The dark-brown solution was purified by reversed phase chromatography (OPTI-UP gel, water:acetonitril=1:0, 9:1, 4:1).

yield: 165 mg (19%); IR(KBr): 1763, 1664 cm$^{-1}$; MS(ISN): 599.2 (M—Na—NH$_3$)$^-$ 11.2.2. (6R,7R)-7-[(Z)-2-Amino-thiazol-4-yl-[(E)-1-(6-chloro-pyridazin-3-yl)-2-oxo-pyrrolidin-3-ylidenemethyl]-

IR (KBr): 1765, 1625, 1536 cm$^{-1}$, MS (ISP): 668.3 (M–2Na+H)$^-$ 11.2.4. (6R,7R)-7-[(Z)-2-(2-Amino-thiazol-4-yl)-2-hydroxyimino-acetylamino]-3-[(E)-1-(2-hydroxy-phenyl)-2-oxo-pyrrolidin-3-ylidenemethyl]-8-oxo-5-thia-1-aza-bicyclo[4.2.0]oct-2-ene-2-carboxylic acid Na salt IR (KBr): 1764, 1621 cm$^{-1}$, MS (ISP): 579 (M+H)$^+$ 11.2.5. (6R,7R)-3-[(E)-1-(4-Amino-benzyl)-2-oxo-pyrrolidin-3-ylidenemethyl]-7-[(Z)-2-(2-amino-thiazol-4-yl)-2-hydroxyimino-acetylamino]-8-oxo-5-thia-1-aza-bicyclo-[4.2.0]oct-2-ene-2-carboxylic acid sodium salt IR (KBr): 3427, 1763, 1619 cm$^{-1}$, MS (ISP): 570.2 (M+H)$^+$ of the acid.

We claim:

1. A compound of formula I

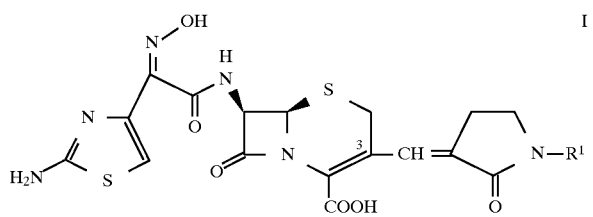

wherein
R¹ is a group selected from 2-, 3- and 4-hydroxyphenyl, 3-nitrophenyl, and 3-fluoro-4-hydroxyphenyl;
as well as readily hydrolyzable esters thereof, pharmaceutically acceptable salts of said compounds and hydrates of the compounds of formula I and of their esters and salts.

2. A compound of formula II

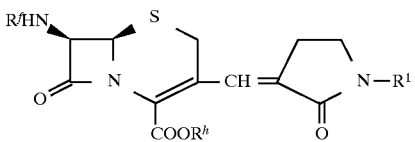

in which R¹ is a group selected from 2-, 3- and 4-hydroxyphenyl, 3-nitrophenyl, and 3-fluoro-4-hydroxyphenyl, $R^f$ is hydrogen or an amino protecting group, $R^h$ is hydrogen or a carboxy protecting group or esters or salts thereof.

3. A pharmaceutical composition comprising a therapeutically effective amount of a compound of the formula

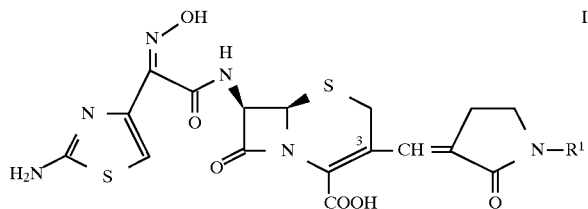

wherein
R¹ is a group selected from 2-, 3- and 4-hydroxyphenyl, 3-nitrophenyl, and 3-fluoro-4-hydroxyphenyl;
as well as readily hydrolyzable esters thereof, pharmaceutically acceptable salts of said compounds and hydrates of the compounds of formula I and of their esters and salts, and a therapeutically acceptable carrier.

4. A method for treating bacterial infections in a mammal comprising administering to said mammal a compound of the formula

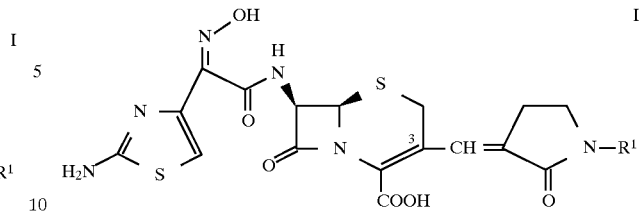

wherein
R¹ is a group selected from 2-, 3- and 4-hydroxyphenyl, 3-nitrophenyl, and 3-fluoro4-hydroxyphenyl;
as well as readily hydrolyzable esters thereof, pharmaceutically acceptable salts of said compounds and hydrates of the compounds of formula I and of their esters and salts, and a therapeutically acceptable carrier.

5. The composition of claim 3, wherein the compound of formula I is (6R,7R)-7-[(Z)-2-(2-Amino-thiazol-4-yl)-2-hydroxyimino-acetylamino]-3-[(E)-1-(4-hydroxy-phenyl)-2-oxo-pyrrolidin-3-ylidenemethyl]-8-oxo-5-thia-1-aza-bicyclo[4.2.0]oct-2-ene-2-carboxylic acid.

6. The composition of claim 3, wherein the compound of formula I is (6R,7R)-7-[(Z)-2-(2-Amino-thiazol-4-yl)-2-hydroxyimino-acetylamino]-3-[(E)-1-(3-nitro-phenyl)-2-oxo-pyrrolidin-3-ylidenemethyl]-8-oxo-5-thia-1-aza-bicyclo[4.2.0]oct-2-ene-2-carboxylic acid.

7. The composition of claim 3, wherein the compound of formula I is (6R,7R)-7-[(Z)-2-(2-Amino-thiazol-4-yl)-2-hydroxyimino-acetylamino]-3-[(E)-1-(3fluoro-4-hydroxyphenyl)-2-oxo-pyrrolidin-3-ylidenemethyl]-8-oxo-5-thia-1-aza-bicyclo[4.2.0]oct-2ene-2-carboxylic acid.

8. The method of claim 4, wherein the compound of formula I is (6R,7R)-7-[(Z)-2-(2-Amino-thiazol-4-yl)-2-hydroxyimino-acetylamino]-3-[(E)-1-(4-hydroxy-phenyl)-2-oxo-pyrrolidin-3-ylidenemethyl]-8-oxo-5-thia-1-aza-bicyclo[4.2.0]oct-2-ene-2-carboxylic acid.

9. The method of claim 4, wherein the compound of formula I is (6R,7R)-7-[(Z)-2-(2-Amino-thiazol-4-yl)-2-hydroxyimino-acetylamino]-3-[(E)-1-(3-nitro-phenyl)-2-oxo-pyrrolidin-3-ylidenemethyl]-8-oxo-5-thia-1-aza-bicyclo[4.2.0]oct-2-ene-2-carboxylic acid.

10. The method of claim 4, wherein the compound of formula I is (6R,7R)-7-[(Z)-2-(2-Amino-thiazol-4-yl)-2-hydroxyimino-acetylamino]-3-[(E)-1(3fluoro-4-hydroxyphenyl)-2-oxo-pyrrolidin-3-ylidenemethyl]-8-oxo-5-thia-1-aza-bicyclo[4.2.0]oct-2ene-2-carboxylic acid.

* * * * *